US012600756B2

(12) United States Patent
Eveleth et al.

(10) Patent No.: US 12,600,756 B2
(45) Date of Patent: Apr. 14, 2026

(54) RECOMBINANT MODIFIED FIBROBLAST GROWTH FACTORS AND THERAPEUTIC USES THEREOF

(71) Applicant: Trefoil Therapeutics, Inc., San Diego, CA (US)

(72) Inventors: David Eveleth, San Diego, CA (US); Jennifer Jenkins-Eveleth, San Diego, CA (US); Amuthakannan Subramaniam, San Diego, CA (US); Ralph Bradshaw, Encinitas, CA (US)

(73) Assignee: TREFOIL THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 17/939,238

(22) Filed: Sep. 7, 2022

(65) Prior Publication Data

US 2023/0130851 A1     Apr. 27, 2023

Related U.S. Application Data

(62) Division of application No. 16/611,182, filed as application No. PCT/US2018/031189 on May 4, 2018, now Pat. No. 11,479,591.

(60) Provisional application No. 62/584,624, filed on Nov. 10, 2017, provisional application No. 62/502,540, filed on May 5, 2017, provisional application No. 62/502,529, filed on May 5, 2017.

(51) Int. Cl.
| | |
|---|---|
| *C07K 14/50* | (2006.01) |
| *A61K 9/00* | (2006.01) |
| *A61K 38/00* | (2006.01) |
| *A61K 38/18* | (2006.01) |
| *A61P 27/02* | (2006.01) |
| *C12N 15/86* | (2006.01) |

(52) U.S. Cl.
CPC .......... *C07K 14/501* (2013.01); *A61K 9/0048* (2013.01); *A61P 27/02* (2018.01); *C12N 15/86* (2013.01); *A61K 38/00* (2013.01); *A61K 38/1825* (2013.01)

(58) Field of Classification Search
None
See application file for complete search history.

(56) References Cited

U.S. PATENT DOCUMENTS

| | | | |
|---|---|---|---|
| 4,022,758 | A | 5/1977 | Andersson et al. |
| 5,033,252 | A | 7/1991 | Carter |
| 5,052,558 | A | 10/1991 | Carter |
| 5,124,154 | A | 6/1992 | Babcock et al. |
| 5,223,483 | A | 6/1993 | Thomas et al. |
| 5,312,911 | A | 5/1994 | Thomas et al. |
| 5,323,907 | A | 6/1994 | Kalvelage |
| 5,409,897 | A | 4/1995 | Thomas et al. |
| 5,510,329 | A | 4/1996 | Belkin et al. |
| 5,552,528 | A | 9/1996 | Burgess et al. |
| 5,624,893 | A | 4/1997 | Yanni |
| 6,642,026 | B2 | 11/2003 | Stegmann et al. |
| 6,780,837 | B1 | 8/2004 | Lavail et al. |
| 7,595,296 | B1 | 9/2009 | Blaber et al. |
| 7,659,379 | B1 | 2/2010 | Blaber et al. |
| 7,696,171 | B1 | 4/2010 | Blaber et al. |
| 7,767,656 | B2 | 8/2010 | Shoichet et al. |
| 7,776,825 | B1 | 8/2010 | Blaber et al. |
| 7,790,682 | B1 | 9/2010 | Blaber et al. |
| 8,119,776 | B1 | 2/2012 | Blaber et al. |
| 8,153,770 | B1 | 4/2012 | Blaber et al. |
| 8,153,771 | B1 | 4/2012 | Blaber et al. |
| 8,461,111 | B2 | 6/2013 | Blaber et al. |
| 11,103,553 | B2 | 8/2021 | Eveleth et al. |
| 2004/0071787 | A1 | 4/2004 | Maciag et al. |
| 2005/0227929 | A1 | 10/2005 | Masferrer |
| 2006/0217310 | A1* | 9/2006 | Chiu ..................... C07D 307/34 |
| | | | 435/325 |
| 2008/0242607 | A1 | 10/2008 | DeFrees |
| 2009/0136445 | A1 | 5/2009 | Wong et al. |
| 2010/0254900 | A1 | 10/2010 | Campbell et al. |
| 2010/0298220 | A1 | 11/2010 | Blaber et al. |
| 2011/0224404 | A1 | 9/2011 | Blaber et al. |
| 2011/0263504 | A1* | 10/2011 | Cerami ................... A61P 39/00 |
| | | | 435/320.1 |
| 2013/0116171 | A1 | 5/2013 | Jonker et al. |
| 2013/0130983 | A1 | 5/2013 | Blaber et al. |
| 2014/0004575 | A1 | 1/2014 | Ito et al. |
| 2014/0045751 | A1 | 2/2014 | Blaber |
| 2014/0178450 | A1 | 6/2014 | Christman et al. |

(Continued)

FOREIGN PATENT DOCUMENTS

| | | |
|---|---|---|
| CN | 1890371 A | 1/2007 |
| CN | 100334114 C | 8/2007 |

(Continued)

OTHER PUBLICATIONS

Moed et al., Arch Dermatol. 2001;137:1357-1360.*
Patterson et al., J Am Acad Dermatol 2016;74:143-70.*
Kamil et al., Ocul Surf. Jan. 2021; 19: 290-306. doi:10.1016/j.jtos.2020.10.006.*
Chauhan et al., Environmental Toxicology and Pharmacology 26 (2008) 113-122.*
Arnau et al. Current strategies for the use of affinity tags and tag removal for the purification of recombinant proteins. Protein Expr Purif. 48(1):1-13 (2006).
Dannowski et al. Lipid-mediated gene transfer of acidic fibroblast growth factor into human corneal endothelial cells. Exp Eye Res. 80(1):93-101 (2005).

(Continued)

*Primary Examiner* — Marianne P Allen
(74) *Attorney, Agent, or Firm* — WILSON SONSINI GOODRICH & ROSATI

(57) ABSTRACT

Described herein are modified fibroblast growth factor (FGF) polypeptides, pharmaceutical compositions and medicaments that include such modified FGF polypeptides, and methods of using such modified FGF polypeptides to treat or prevent conditions that benefit from administration of FGFs.

19 Claims, 12 Drawing Sheets

Specification includes a Sequence Listing.

(56) References Cited

U.S. PATENT DOCUMENTS

| | | | | |
|---|---|---|---|---|
| 2015/0099701 A1* | 4/2015 | Lee | C07K 14/501 | |
| | | | 530/399 | |
| 2015/0104494 A1* | 4/2015 | Oliver | A61K 38/1825 | |
| | | | 424/443 | |
| 2015/0111821 A1 | 4/2015 | Suh et al. | | |
| 2015/0224064 A1 | 8/2015 | Günther et al. | | |
| 2015/0253308 A1* | 9/2015 | Hill | G01N 33/5082 | |
| | | | 435/29 | |
| 2016/0137690 A1 | 5/2016 | Pizarro et al. | | |
| 2016/0237133 A1 | 8/2016 | Suh et al. | | |
| 2016/0263190 A1 | 9/2016 | Eveleth et al. | | |
| 2017/0362323 A1 | 12/2017 | Niwa et al. | | |
| 2018/0228869 A1 | 8/2018 | Evans et al. | | |
| 2020/0157164 A1 | 5/2020 | Fang et al. | | |
| 2020/0190158 A1 | 6/2020 | Eveleth et al. | | |
| 2021/0009650 A1 | 1/2021 | Eveleth et al. | | |
| 2021/0338777 A1 | 11/2021 | Eveleth et al. | | |
| 2021/0353714 A1 | 11/2021 | Graham et al. | | |
| 2024/0024421 A1 | 1/2024 | Eveleth | | |
| 2025/0066440 A1 | 2/2025 | Eveleth | | |

FOREIGN PATENT DOCUMENTS

| | | |
|---|---|---|
| CN | 103945871 A | 7/2014 |
| EP | 0791576 A2 | 8/1997 |
| GB | 2223496 A | 4/1990 |
| JP | 2004517607 A | 6/2004 |
| JP | 2007535306 A | 12/2007 |
| JP | 2014534172 A | 12/2014 |
| KR | 20140069250 A | 6/2014 |
| WO | WO-9917800 A1 | 4/1999 |
| WO | WO-9955861 A2 | 11/1999 |
| WO | WO-0138357 A2 | 5/2001 |
| WO | WO-0172957 A2 | 10/2001 |
| WO | WO-0214471 A2 | 2/2002 |
| WO | WO-2006105315 A2 | 10/2006 |
| WO | WO-2007124082 A2 | 11/2007 |
| WO | WO-2013049247 A1 | 4/2013 |
| WO | WO-2015048188 A2 | 4/2015 |
| WO | WO-2015061361 A1 | 4/2015 |
| WO | WO-2015198175 A1 | 12/2015 |
| WO | WO-2016172153 A2 | 10/2016 |
| WO | WO-2016172156 A2 | 10/2016 |
| WO | WO-2017026156 A1 | 2/2017 |
| WO | WO-2017147293 A1 | 8/2017 |
| WO | WO-2017172525 A2 | 10/2017 |
| WO | WO-2018204847 A2 | 11/2018 |
| WO | WO-2021263134 A1 | 12/2021 |
| WO | WO-2023019218 A1 | 2/2023 |
| WO | WO-2023043743 A1 | 3/2023 |

OTHER PUBLICATIONS

Frankel et al. Characterization of diphtheria fusion proteins targeted to the human interleukin-3 receptor. Protein Engineering 13(8):575-581 (2000).

Muller et al., Spliceosomal peptide P140 for immunotherapy of systemic lupus erythematosus: results of an early phase II clinical trial. Arthritis Rheum. 58(12):3873-83 (2008).

Pakula et al. Genetic Analysis of Protein Stability and Function. Annu. Rev. Genet. 23:289-310 (1989).

Tokuriki et al. Stability effects of mutations and protein evolvability. Curr. Opin. Struc. Biol. 19:596-604 (2009).

Trufanov et al. Corneal degenerations. Vestnik Ophthalmologiya 5(part 2):282-288 (English Abstract). Available at https://doi.org/10.17116/oftalma2018134051282 (2018).

U.S. Appl. No. 16/089,698 Office Action dated Mar. 14, 2023.

U.S. Appl. No. 17/378,557 Office Action dated Apr. 25, 2023.

U.S. Appl. No. 17/378,557 Office Action dated Sep. 29, 2023.

Anshu et al. Endothelial keratoplasty: a revolution in evolution. Surv Ophthalmol 57(3):236-252 (2012).

Ashena et al. Autoimmune Dry Eye without Significant Ocular Surface Co-Morbidities and Mental Health. Vision(Basel) 4(4):43 (2020).

Becker et al. Safety Assessment of Glycerin as Used in Cosmetics. Int J Toxicol. 38(3 suppl):6S-22S (2019).

Bradshaw et al. The preparation, properties, and reactivation of the mixed disulfide derivative of egg white lysozyme and L-cystine. J Biol Chem 242:3789-98 (1967).

Brown et al. Synthesis of stromal glycosaminoglycans in response to injury. J Cell Biochem 59(1):57-68 (1995).

Brych et al. Structure and stability effects of mutations designed to increase the primary sequence symmetry within the core region of a β-trefoil. Protein Science 10:2587-2599 (2001).

Burstein. Growth factor effects on corneal wound healing. J Ocul Pharmacol 3(3):263-277 (1987).

Caruelle et al. Immunological study of acidic fibroblast growth factor (aFGF) distribution in the eye. J Cell Biochem 39(2):117-128 (1989).

Culajay et al. Thermodynamic Characterization of Mutants of Human Fibroblast Growth Factor 1 with an Increased Physiological Half-Life. Biochemistry 39(24):7153-7158 (2000).

Dannowski et al. Lipid-mediated gene transfer of acidic fibroblast growth factor into human corneal endothelial cells. Exp Eye Res 80:93-101 (2005).

Dubey et al. Redesigning symmetry-related "mini-core" regions of FGF-1 to increase primary structure symmetry: thermodynamic and functional consequences of structural symmetry. Protein Sci 14(9):2315-2323 (2005).

Dubey et al. Spackling the crack: stabilizing human fibroblast growth factor-1 by targeting the N and C terminus beta-strand interactions. J Mol Biol 371(1):256-268 (2007).

Elhalis et al. Fuchs endothelial corneal dystrophy. Ocul Surf 8(4):173-184 (2010).

Engelmann et al. Growth of Human Corneal Endothelial Cells in a Serum-reduced Medium. Cornea 14(1):62-70 (1995).

Eveleth et al., An engineered human fibroblast growth factor-1 derivative, TTHX1114, ameliorates short-term corneal nitrogen mustard injury in rabbit organ cultures. Invest Ophthalmol Vis Sci. 59(11):4720-4730 (2018).

Garcia et al. Development of a reliable non-union model in mice. J Surg Res 147(1):84-91 (2008).

Gospodarowicz et al. Stimulation of corneal endothelial cell pro-liferations in vitro by fibroblast and epidermal growth factors. Exp Eye Res 25:75-89 (1977).

Grant et al. Effects of epidermal growth factor, fibroblast growth factor, and transforming growth factor-beta on corneal cell chemotaxis. Invest Ophthalmol Vis Sci 33(12):3292-3301 (1992).

He et al. Revisited microanatomy of the corneal endothelial periphery: new evidence for continuous centripetal migration of endothelial cells in humans. Stem Cells 30(11):2523-2534 (2012).

Johnstone et al. Factors affecting bovine corneal endothelial cell density in vitro. Br J Ophthalmol 80(3):256-262 (1996).

Kathuria et al. Categorization of Marketed Artificial Tear Formulations Based on Their Ingredients: A Rational Approach for Their Use. J Clin Med. 10(6):1289 (2021).

Kaye et al. The Fine Structure of the Rabbit Cornea and the Uptake and Transport of Colloidal Particles by the Cornea in Vivo. The Journal of Cell Biology 12:457-479 (1962).

Keenan et al. Trends in the indications for corneal graft surgery in the United Kingdom: 1999 through 2009. Arch Ophthalmol 130(5):621-628 (2012).

Kim et al. Application of FGF-2 to modulate herpetic stromal keratitis. Curr Eye Res 31(12):1021-1028 (2006).

Klintworth. Corneal dystrophies. Orphanet Journal of Rare Diseases 4:7 (38 pgs) (2009).

Landshman et al. Regeneration of cat corneal endothelium induced in vivo by fibroblast growth factor. Exp Eye Res 45:805-811 (1987).

Lee et al. A Logical OR Redundancy within the Asx-Pro-Asx-Gly Type I β-Turn Motif. JMB 377:1251-1264 (2008).

Lee et al. FGF-2-induced wound healing in corneal endothelial cells requires Cdc42 activation and Rho inactivation through the phosphatidylinositol 3-kinase pathway. Invest Ophthalmol Vis Sci 47(4):1376-1386 (2006).

Lee et al. Structural basis of conserved cysteine in the fibroblast growth factor family: evidence for a vestigial half-cystine. J Mol Biol 393(1):128-139 (2009).

(56)                  References Cited

OTHER PUBLICATIONS

Li et al. Eye banking and the changing trends in contemporary corneal surgery. Int Ophthalmol Clin 50(3):101-112 (2010).

Lin et al. Dry eye disease: A review of diagnostic approaches and treatments. Saudi J Ophthalmol. 28(3):173-18 (2014).

Lovicu et al. Expression of FGF-1 and FGF-2 mRNA during lens morphogenesis, differentiation and growth. Cur Eye Res 16(3):222-230 (1997).

Lozano et al. 1H NMR structural characterization of a nonmitogenic, vasodilatory, ischemia-protector and neuromodulatory acidic fibroblast growth factor. Biochemistry 39:4982-4993 (2000).

Mcgowan et al. Stem cell markers in the human posterior limbus and corneal endothelium of unwounded and wounded corneas. Mol Vis 13:1984-2000 (2007).

Meduri et al. Effect of basic fibroblast growth factor in transgenic mice: corneal epithelial healing process after excimer laser photoablation. Ophthalmologica 223(2):139-144 (2009).

Meduri et al. Effect of basic fibroblast growth factor on corneal epithelial healing after photorefractive keratectomy. J Refract Surg 28(3):220-223 (2012).

Mellin et al. Acidic fibroblast growth factor accelerates dermal wound healing in diabetic mice. J Invest Dermatol 104:850-855 (1995).

Mimura et al. Comparison of rabbit corneal endothelial cell precursors in the central and peripheral cornea. Invest Ophthalmol Vis Sci 46(10):3645-3648 (2005).

Miyakawa et al. The C-terminal region of fibroblast growth factor-1 is crucial for its biological activity and high level protein expression in mammalian cells. Growth Factors 16:191-200 (1999).

Nikol et al. Therapeutic Angiogenesis With Intramuscular NV1FGF Improves Amputation-free Survival in Patients With Critical Limb Ischemia. Mol Ther 16(5):972-978 (2008).

Noji et al. Expression pattern of acidic and basic fibroblast growth factor genes in adult rat eyes. Biochem Biophys Res Commu 168(1):343-349 (1990).

Okumura et al. Effect of the Rho Kinase Inhibitor Y-27632 on Corneal Endothelial Wound Healing. Invest Ophthalmol Vis Sci 56(10):6067-6074 (2015).

Okumura et al. Enhancement of corneal endothelium wound healing by Rho-associated kinase (ROCK) inhibitor eye drops. Br J Ophthalmol 95(7):1006-1009 (2011).

Olsen et al. Insights into the molecular basis for fibroblast growth factor receptor autoinhibition and ligand-binding promiscuity. PNAS USA 101(4):935-940 (2004).

Ortega et al. Conversion of cysteine to serine residues alters the activity, stability, and heparin dependence of acidic fibroblast growth factor. J Biol Chem 266:5842-5846 (1991).

Patel. Graft survival and endothelial outcomes in the new era of endothelial keratoplasty. Exp Eye Res 95(1):40-47 (2012).

PCT/US2014/057302 International Search Report and Written Opinion dated Apr. 6, 2015.

PCT/US2018/031189 International Search Report and Written Opinion dated Jul. 3, 2018.

PCT/US2021/039139 International Search Report and Written Opinion dated Oct. 26, 2021.

PCT/US2022/043378 International Invitation to Pay Additional Fees dated Oct. 27, 2022.

PCT/US2022/043378 International Search Report and Written Opinion dated Feb. 1, 2023.

PCT/US2022/074858 International Invitation to Pay Additional Fees dated Oct. 11, 2022.

PCT/US2022/074858 International Search Report and Written Opinion dated Jan. 11, 2023.

Prechel et al. Heparin-induced thrombocytopenia: an update. Semin Thromb Hemost 38:483-496 (2012).

Price et al. Descemet's membrane endothelial keratoplasty surgery: update on the evidence and hurdles to acceptance. Cur Opin Ophthalmol 24(4):329-335 (2013).

Ramos et al. FGF-1 reverts epithelial-mesenchymal transition induced by TGF-{beta}1 through MAPK/ERK kinase pathway. Am J Physiol Lung Cell Mol Physiol 299:L222-L231 (2010).

Rieck et al. Human recombinant bFGF stimulates corneal endothelial wound healing in rabbits. Curr Eye Res 11(12):1161-1172 (1992).

Sauer et al., Separation of truncated basic fibroblast growth factor from the full-length protein by hydrophobic interaction chromatography. Separation and Purification Technology 254:117564 [1-9] (2021).

Schmedt et al. Molecular bases of corneal endothelial dystrophies. Exp Eye Res 95(1):24-34 (2012).

Schulz et al. Acidic and basic FGF in ocular media and lens: implications for lens polarity and growth patterns. Development 118(1):117-126 (1993).

Thalmann-Goetsch et al. Comparative study on the effects of different growth factors on migration of bovine corneal endothelial cells during wound healing. Acta Ophthalmol Scand 75(5):490-495 (1997).

Themistou et al. Facile synthesis of thiol-functionalized amphiphilic polylactide-methacrylic diblock copolymers. Polym Chem 5: 1405 (2014).

Tikhonovich et al. The role of inflammation in the development of proliferative vitreoretinopathy. Clinical Medicine 93(7):14-20 (2015) (English Abstract).

U.S. Appl. No. 15/024,824 Office Action dated Apr. 11, 2019.

U.S. Appl. No. 15/024,824 Office Action dated Apr. 13, 2018.

U.S. Appl. No. 15/024,824 Office Action dated Dec. 19, 2019.

U.S. Appl. No. 15/024,824 Office Action dated Jul. 31, 2020.

U.S. Appl. No. 15/024,824 Office Action dated Mar. 23, 2021.

U.S. Appl. No. 15/024,824 Office Action dated May 24, 2017.

U.S. Appl. No. 15/024,824 Office Action dated Oct. 25, 2017.

U.S. Appl. No. 15/024,824 Office Action dated Oct. 9, 2018.

U.S. Appl. No. 16/089,698 Office Action dated May 25, 2022.

Whikehart et al. Evidence suggesting the existence of stem cells for the human corneal endothelium. Mol Vis 11:816-824 (2005).

Williams et al. Thiol modification of silicon-substituted hydroxyapatite nanocrystals facilitates fluorescent labelling and visualisation of cellular internalisation. J Mater Chem B 1:4370 (2013).

Wilson et al. Epidermal growth factor, transforming growth factor alpha, transforming growth factor beta, acidic fibroblast growth factor, basic fibroblast growth factor, and interleukin-1 proteins in the cornea. Exp Eye Res 59:53-72 (1994).

Woost et al. Effect of growth factors with dexamethasone on healing of rabbit corneal stromal incisions. Exp Eye Res 40(1):47-60 (1985).

Xia et al. Mutation Choice to Eliminate Buried Free Cysteines in Protein Therapeutics. J Pharm Sci 104:566-576 (2015).

Xiong et al. Fractionation of proteins by heparin chromatography. Methods Mol Biol 424(1):213-221 (2008).

Xu et al. Diversification of the structural determinants of fibroblast growth factor-heparin interactions: implications for binding specificity J Biol Chem 287(47):40061-40673 (2012).

Yamagami et al. Distribution of precursors in human corneal stromal cells and endothelial cells. Ophthalmology 114(3):433-439 (2007).

Yu et al. Progenitors for the corneal endothelium and trabecular meshwork: a potential source for personalized stem cell therapy in corneal endothelial diseases and glaucoma. J Biomed Biotechnol 2011:412743 (13 pgs.) (2011).

Zakrsewska et al. Increased protein stability of FGF1 can compensate for its reduced affinity for heparin. J Biol Chem 284:25388-25403 (2009).

Zakrzewska et al. Design of fully active FGF-1 variants with increased stability. Protein Eng Des Sel 17(8):603-611 (2004).

Zakrzewska et al. FGF-1: from biology through engineering to potential medical applications. Crit Rev Clin Lab Sci. 45(1):91-135 (2008).

Higashibata. The Elements of High Expression of Heterologous Proteins with *E. coli* as a Host, Bio Topics. Biotechnology Basic Course Biotechnology 91(2):96-100 (2013).

Hirel et al. Extent of N-terminal methionine excision from *Escherichia coli* proteins is governed by the side-chain length of the penultimate amino acid. PNAS USA 86(21):8247-51 (1989).

(56)　　　　　References Cited

OTHER PUBLICATIONS

Western Honyoshi. Bioengineering Basic Lecture Biograph, a heterologous high expression with the host as a host. Biotechnology 91(2):96-100 (2013).

Azher et al. Herpes simplex keratitis: challenges in diagnosis and clinical management. Clin Ophthalmol 11:185-191 (2017).

Baird et al. The fibroblast growth factor family. Cancer Cells 3:239-243 (1991).

Benmohamed et al. Decreased reactivation of a herpes simplex virus type 1 (HSV-1) latency-associated transcript (LAT) mutant using the in vivo mouse UV-B model of induced reactivation. J Neurovirol 21(5):508-17 (2015).

Burgess et al. The heparin-binding (fibroblast) growth factor family of proteins. Annu Rev. Biochem. 58:575-606 (1989).

Cheng et al. Spinal Cord Repair with Acidic Fibroblast Growth Factor as a Treatment for a Patient with Chronic Paraplegia. Spine 29(14):E284-E288 (2004).

Dhanushkodi et al., Healing of Ocular Herpetic Disease Following Treatment with an Engineered FGF-1 as Associated with Increased Corneal Anti-Inflammatory M2 Macrophages. Frontiers in Immunology 12(673763) 1-12 (2021).

Fredj-Reygrobellet et al. Effects of aFGF and bFGF on wound healing in rabbit corneas. Curr Eye Res 6(10):1205-1209 (1987).

Ganesan et al. Chemical Warfare Agents. Journal of Pharmacy and Bioallied Sciences 2.3: 166-178 (2010).

Heiligenhaus et al. Improvement of HSV-1 Necrotizing Keratitis with Amniotic Membrane Transplantation Invest Ophthalmol Vis Sci 42(9):1969-1974 (2001).

Jiang et al. Coated microneedles for drug delivery to the eye. Invest Ophthalmol Vis Sci 48(9):4038-4043 (2007).

Joyce et al. Relationship among oxidative stress, DNA damage, and proliferative capacity in human corneal endothelium. Invest Ophthalmol Vis Sci 50:2116-2122 (2009).

Kanavi et al. Chronic and delayed mustard gas keratopathy: a histopathologic and immunohistochemical study. Eur. J Ophthalmol. 20(5):839-43 (2010).

Kay et al. Corneal endothelial modulation: a factor released by leukocytes induces basic fibroblast growth factor that modulates cell shape and collagen. Invest Ophthalmol Vis Sci 34(3):663-72 (1993).

Koevary. Pharmacokinetics of topical ocular drug delivery: potential uses for the treatment of diseases of the posterior segement and beyond. Curr. Drug Metab. 4(3):213-222 (2003).

Lee et al. Common and distinct pathways for cellular activities in FGF-2 signaling induced by IL-1beta in corneal endothelial cells. Invest Ophthalmol Vis Sci 50(5):2067-2076(2009).

Lee et al. Review on the systemic delivery of insulin via the ocular route. Int. J. Pharm. 233(1-2):1-18 (2002).

Lin. Functional recovery of chronic complete idiopathic transverse myelitis after administration of neurotrophic factors. Spinal Cord 44:254-257 (2006).

Mckeehan et al. The heparan sulfate-fibroblast growth factor family: diversity of structure and function. Prog. Nucleic Acid Res. Mol. Biol. 59:135-176 (1998).

Mori et al., Direct binding of integrin avP3 to FGFI plays a role in FGFI signaling. J Biol Chem 283(26):18066-18075 (2008).

Ornitz el al. Receptor specificity of the fibroblast growth factor family. J Biol Chem 271(25):15292-15297 (1996).

Reuss et al. Fibroblast growth factors and their receptors in the central nervous system. Cell Tissue Res. 313:139-157 (2003).

Rosano et al. Recombinant protein expression in *Escherichia coli*: advances and challenges. Frontiers in Microbiology 5:172 (2014).

Tewari-Singh et al. Cutaneous exposure to vesicant phosgene oxime: Acute effects on the skin and systemic toxicity. Toxicol Appl Pharmacol. 317:25-32 (2017).

Tewari-Singh et al. Mustard vesicating agent-induced toxicity in the skin tissue and silibinin as a potential countermeasure. Ann N Y Acad Sci. 1374(1):184-92 (2016).

Tsuji et al. Preparation of 3-acetoacetylaminobenzo[b]furan derivatives with cysteinyl leukotriene receptor 2 antagonistic activity. Org. Biomol. Chem. 1:3139-3141 (2003).

U.S. Appl. No. 16/611,182 Office Action dated Dec. 17, 2021.

U.S. Appl. No. 16/611,182 Office Action dated Feb. 9, 2021.

U.S. Appl. No. 16/611,182 Office Action dated Jul. 21, 2021.

Xia et al. Pharmacokinetic properties of 2nd-generation fibroblast growth factor-1 mutants for therapeutic application. PLoS one 7(11):e48210 (12 pgs) (2012).

Yamaji et al., A novel fibroblast growth factor-I (FGFI) mutant that acts as an FGF antagonist. PLoS one 5(4):e10273 (2010).

Zhang et al. Receptor specificity of the fibroblast growth factor family. The complete mammalian FGF family. J Biol Chem 281(23):15694-15700 (2006).

Adachi, K. et al., Expression of Functional Soluble Human a-Globin Chains of Hemoglobin in Bacteria. Protein Expr Purif 20(1):37-44 (2000).

Atamas, Sergei P, et al., Cytokine Regulation Of Pulmonary Fibrosis In Scleroderma. Cytokine & Growth Factor Reviews 14(6):537-550 (2003).

Doucet, Christelle, et al., Interleukin (IL) 4 And IL-13 Act On Human Lung Fibroblasts. Implication In Asthma. Journal of Clinical Investigation 101(10):2129-2139 (1998).

Endo, S. et al. The additional methionine residue at the N-terminus of bacterially expressed human interleukin-2 affects the interaction between the N- and C-termini. Biochemistry 40(4):914-9 (2001) (Abstract only).

Fertin, Marie, et al., Serum MMP-8: A Novel Indicator Of Left Ventricular Remodeling And Cardiac Outcome In Patients After Acute Myocardial Infarction. PLoS One 8(8):e71280, 6 Pages (2013).

Kelly, Margaret, et al., Re-Evaluation Of Fibrogenic Cytokines In Lung Fibrosis. Current Pharmaceutical Design 9(1):39-49 (2003).

Letterio, John J, et al., Regulation Of Immune Responses By TGF-beta. Annual Review of Immunology 16:137-161 (1998).

Liao, You-Di et al., Removal of N-terminal methionine from recombinant proteins by engineered *E. coli* methionine aminopeptidase. Protein Sci 13(7):1802-10 (2004).

Liao, You-Di et al., The structural integrity exerted by N-terminal pyroglutamate is crucial for the cytotoxicity of frog ribonuclease from Rana pipiens. Nucleic Acids Res. 31(18):5247-55 (2003).

Staples, R, et al., Gastrointestinal Irritant Effect Of Glycerin As Compared With Sorbitol And Propylene Glycol In Rats And Dogs. Journal of Pharmaceutical Sciences 56(3):398-400 (1967).

Zhu, Zhou, et al., Pulmonary Expression Of Interleukin-13 Causes Inflammation, Mucus Hypersecretion, Subepithelial Fibrosis, Physiologic Abnormalities, And Eotaxin Production. Journal of Clinical Investigation 103(6):779-788 (1999).

U.S. Appl. No. 18/069,585 Office Action dated Aug. 12, 2025.

* cited by examiner

TTHX1114 protects against NM

FIG. 6

Histopathological grading

Paraformaldehyde fixed, paraffin embedded, H&E stain

| Epidermal Layer | Stromal Layer |
|---|---|
| Total Epidermal Differentiation | Stroma |
| 1 Normal 3 layer, good differentiation<br>2 Disruption in differentiation<br>3 Single layer only<br>4 Single layer, partial coverage<br>5 No epidermis present | 1 No disruption/vacoules present<br>2 Vacuoles around some keratocytes<br>3 Vacuoles around most keratocytes<br>4 Generalized disruption to stroma |
| Basal Layer | Keratocytes |
| 1 Columnar formation proper orientation<br>2 Columnar and rounded with some orientation<br>3 Rounded, erratic orientation<br>4 Rounded, erratic orientation, partial coverage<br>5 No BL present | 1 Increased number of keratocytes<br>2 Present, in normal alignment to EPI<br>3 Abnormal number, shape (mild)<br>4 Abnormal number, shape (moderate)<br>5 Loss of keratocytes |
| Epithelial Intracellular Adhesion (EIA) |  |
| 1 No breaks in EIA<br>2 Mild breaks in EIA<br>3 Moderate breaks in EIA<br>4 No EIA – cells separated<br>5 No epithelium present |  |

FGF-1 levels reduced by nitrogen mustard

Naive

EdU incorporation by epithelial layer in peripheral cornea over 24hrs

SEQUENCE LISTING

```
Sequence total quantity: 207
SEQ ID NO: 1              moltype = AA  length = 140
FEATURE                   Location/Qualifiers
source                    1..140
                          mol_type = protein
                          organism = Homo sapiens
SEQUENCE: 1
FNLPPGNYKK PKLLYCSNGG HFLRILPDGT VDGTRDRSDQ HIQLQLSAES VGEVYIKSTE   60
TGQYLAMDTD GLLYGSQTPN EECLFLERLE ENHYNTYISK KHAEKNWFVG LKKNGSCKRG  120
PRTHYGQKAI LFLPLPVSSD                                              140

SEQ ID NO: 2              moltype = AA  length = 141
FEATURE                   Location/Qualifiers
REGION                    1..141
                          note = Description of Artificial Sequence: Synthetic
                           polypeptide
source                    1..141
                          mol_type = protein
                          organism = synthetic construct
SEQUENCE: 2
MFNLPPGNYK KPKLLYSSNG GHFLRILPDG TVDGTRDRSD QHIQLQLSAE SVGEVYIKST   60
ETGQYLCMDT DGLLYGSQTP NEECLFLERL EENHYNTYIS KKHAEKNWFV GLKKNGSVKR  120
GPRTHYGQKA ILFLPLPVSS D                                            141

SEQ ID NO: 3              moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 3
MAEGEITTFT ALTEK                                                    15

SEQ ID NO: 4              moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 4
ALTEK                                                               5

SEQ ID NO: 5              moltype = AA  length = 4
FEATURE                   Location/Qualifiers
REGION                    1..4
                          note = Description of Artificial Sequence: Synthetic peptide
source                    1..4
                          mol_type = protein
                          organism = synthetic construct
SEQUENCE: 5
LTEK                                                                4

SEQ ID NO: 6              moltype =    length =
SEQUENCE: 6
000

SEQ ID NO: 7              moltype =    length =
SEQUENCE: 7
000

SEQ ID NO: 8              moltype =    length =
SEQUENCE: 8
000

SEQ ID NO: 9              moltype = AA  length = 146
FEATURE                   Location/Qualifiers
REGION                    1..146
                          note = Description of Artificial Sequence: Synthetic
                           polypeptide
source                    1..146
                          mol_type = protein
                          organism = synthetic construct
SEQUENCE: 9
MALTEKFNLP PGNYKKPKLL YCSNGGHFLR ILPDGTVDGT RDRSDQHIQL QLSAESVGEV   60
YIKSTETGQY LAMDTDGLLY GSQTPNEECL FLERLEENHY NTYISKKHAE KNWFVGLKKN  120
GSCKRGPRTH YGQKAILFLP LPVSSD                                       146
```

```
SEQ ID NO: 10              moltype = AA  length = 145
FEATURE                   Location/Qualifiers
REGION                    1..145
                          note = Description of Artificial Sequence: Synthetic
                           polypeptide
source                    1..145
                          mol_type = protein
                          organism = synthetic construct
SEQUENCE: 10
MLTEKFNLPP GNYKKPKLLY CSNGGHFLRI LPDGTVDGTR DRSDQHIQLQ LSAESVGEVY  60
IKSTETGQYL AMDTDGLLYG SQTPNEECLF LERLEENHYN TYISKKHAEK NWFVGLKKNG  120
SCKRGPRTHY GQKAILFLPL PVSSD                                        145

SEQ ID NO: 11              moltype = AA  length = 144
FEATURE                   Location/Qualifiers
REGION                    1..144
                          note = Description of Artificial Sequence: Synthetic
                           polypeptide
source                    1..144
                          mol_type = protein
                          organism = synthetic construct
SEQUENCE: 11
MTEKFNLPPG NYKKPKLLYC SNGGHFLRIL PDGTVDGTRD RSDQHIQLQL SAESVGEVYI  60
KSTETGQYLA MDTDGLLYGS QTPNEECLFL ERLEENHYNT YISKKHAEKN WFVGLKKNGS  120
CKRGPRTHYG QKAILFLPLP VSSD                                         144

SEQ ID NO: 12              moltype = AA  length = 143
FEATURE                   Location/Qualifiers
REGION                    1..143
                          note = Description of Artificial Sequence: Synthetic
                           polypeptide
source                    1..143
                          mol_type = protein
                          organism = synthetic construct
SEQUENCE: 12
MEKFNLPPGN YKKPKLLYCS NGGHFLRILP DGTVDGTRDR SDQHIQLQLS AESVGEVYIK  60
STETGQYLAM DTDGLLYGSQ TPNEECLFLE RLEENHYNTY ISKKHAEKNW FVGLKKNGSC  120
KRGPRTHYGQ KAILFLPLPV SSD                                          143

SEQ ID NO: 13              moltype = AA  length = 142
FEATURE                   Location/Qualifiers
REGION                    1..142
                          note = Description of Artificial Sequence: Synthetic
                           polypeptide
source                    1..142
                          mol_type = protein
                          organism = synthetic construct
SEQUENCE: 13
MKFNLPPGNY KKPKLLYCSN GGHFLRILPD GTVDGTRDRS DQHIQLQLSA ESVGEVYIKS  60
TETGQYLAMD TDGLLYGSQT PNEECLFLER LEENHYNTYI SKKHAEKNWF VGLKKNGSCK  120
RGPRTHYGQK AILFLPLPVS SD                                           142

SEQ ID NO: 14              moltype = AA  length = 146
FEATURE                   Location/Qualifiers
REGION                    1..146
                          note = Description of Artificial Sequence: Synthetic
                           polypeptide
source                    1..146
                          mol_type = protein
                          organism = synthetic construct
SEQUENCE: 14
MALTEKFNLP PGNYKKPKLL YSSNGGHFLR ILPDGTVDGT RDRSDQHIQL QLSAESVGEV  60
YIKSTETGQY LCMDTDGLLY GSQTPNEECL FLERLEENHY NTYISKKHAE KNWFVGLKKN  120
GSVKRGPRTH YGQKAILFLP LPVSSD                                       146

SEQ ID NO: 15              moltype = AA  length = 145
FEATURE                   Location/Qualifiers
REGION                    1..145
                          note = Description of Artificial Sequence: Synthetic
                           polypeptide
source                    1..145
                          mol_type = protein
                          organism = synthetic construct
SEQUENCE: 15
MLTEKFNLPP GNYKKPKLLY SSNGGHFLRI LPDGTVDGTR DRSDQHIQLQ LSAESVGEVY  60
IKSTETGQYL CMDTDGLLYG SQTPNEECLF LERLEENHYN TYISKKHAEK NWFVGLKKNG  120
SVKRGPRTHY GQKAILFLPL PVSSD                                        145
```

```
SEQ ID NO: 16              moltype = AA   length = 144
FEATURE                    Location/Qualifiers
REGION                     1..144
                           note = Description of Artificial Sequence: Synthetic
                            polypeptide
source                     1..144
                           mol_type = protein
                           organism = synthetic construct
SEQUENCE: 16
MTEKFNLPPG NYKKPKLLYS SNGGHFLRIL PDGTVDGTRD RSDQHIQLQL SAESVGEVYI  60
KSTETGQYLC MDTDGLLYGS QTPNEECLFL ERLEENHYNT YISKKHAEKN WFVGLKKNGS  120
VKRGPRTHYG QKAILFLPLP VSSD                                         144

SEQ ID NO: 17              moltype = AA   length = 143
FEATURE                    Location/Qualifiers
REGION                     1..143
                           note = Description of Artificial Sequence: Synthetic
                            polypeptide
source                     1..143
                           mol_type = protein
                           organism = synthetic construct
SEQUENCE: 17
MEKFNLPPGN YKKPKLLYSS NGGHFLRILP DGTVDGTRDR SDQHIQLQLS AESVGEVYIK  60
STETGQYLCM DTDGLLYGSQ TPNEECLFLE RLEENHYNTY ISKKHAEKNW FVGLKKNGSV  120
KRGPRTHYGQ KAILFLPLPV SSD                                          143

SEQ ID NO: 18              moltype = AA   length = 142
FEATURE                    Location/Qualifiers
REGION                     1..142
                           note = Description of Artificial Sequence: Synthetic
                            polypeptide
source                     1..142
                           mol_type = protein
                           organism = synthetic construct
SEQUENCE: 18
MKFNLPPGNY KKPKLLYSSN GGHFLRILPD GTVDGTRDRS DQHIQLQLSA ESVGEVYIKS  60
TETGQYLCMD TDGLLYGSQT PNEECLFLER LEENHYNTYI SKKHAEKNWF VGLKKNGSVK  120
RGPRTHYGQK AILFLPLPVS SD                                           142

SEQ ID NO: 19              moltype = AA   length = 145
FEATURE                    Location/Qualifiers
REGION                     1..145
                           note = Description of Artificial Sequence: Synthetic
                            polypeptide
source                     1..145
                           mol_type = protein
                           organism = synthetic construct
SEQUENCE: 19
ALTEKFNLPP GNYKKPKLLY CSNGGHFLRI LPDGTVDGTR DRSDQHIQLQ LSAESVGEVY  60
IKSTETGQYL AMDTDGLLYG SQTPNEECLF LERLEENHYN TYISKKHAEK NWFVGLKKNG  120
SCKRGPRTHY GQKAILFLPL PVSSD                                        145

SEQ ID NO: 20              moltype = AA   length = 144
FEATURE                    Location/Qualifiers
REGION                     1..144
                           note = Description of Artificial Sequence: Synthetic
                            polypeptide
source                     1..144
                           mol_type = protein
                           organism = synthetic construct
SEQUENCE: 20
LTEKFNLPPG NYKKPKLLYC SNGGHFLRIL PDGTVDGTRD RSDQHIQLQL SAESVGEVYI  60
KSTETGQYLA MDTDGLLYGS QTPNEECLFL ERLEENHYNT YISKKHAEKN WFVGLKKNGS  120
CKRGPRTHYG QKAILFLPLP VSSD                                         144

SEQ ID NO: 21              moltype = AA   length = 143
FEATURE                    Location/Qualifiers
REGION                     1..143
                           note = Description of Artificial Sequence: Synthetic
                            polypeptide
source                     1..143
                           mol_type = protein
                           organism = synthetic construct
SEQUENCE: 21
TEKFNLPPGN YKKPKLLYCS NGGHFLRILP DGTVDGTRDR SDQHIQLQLS AESVGEVYIK  60
STETGQYLAM DTDGLLYGSQ TPNEECLFLE RLEENHYNTY ISKKHAEKNW FVGLKKNGSC  120
KRGPRTHYGQ KAILFLPLPV SSD                                          143

SEQ ID NO: 22              moltype = AA   length = 142
```

-continued

```
FEATURE              Location/Qualifiers
REGION               1..142
                     note = Description of Artificial Sequence: Synthetic
                      polypeptide
source               1..142
                     mol_type = protein
                     organism = synthetic construct
SEQUENCE: 22
EKFNLPPGNY KKPKLLYCSN GGHFLRILPD GTVDGTRDRS DQHIQLQLSA ESVGEVYIKS  60
TETGQYLAMD TDGLLYGSQT PNEECLFLER LEENHYNTYI SKKHAEKNWF VGLKKNGSCK  120
RGPRTHYGQK AILFLPLPVS SD                                          142

SEQ ID NO: 23        moltype = AA  length = 141
FEATURE              Location/Qualifiers
REGION               1..141
                     note = Description of Artificial Sequence: Synthetic
                      polypeptide
source               1..141
                     mol_type = protein
                     organism = synthetic construct
SEQUENCE: 23
KFNLPPGNYK KPKLLYCSNG GHFLRILPDG TVDGTRDRSD QHIQLQLSAE SVGEVYIKST  60
ETGQYLAMDT DGLLYGSQTP NEECLFLERL EENHYNTYIS KKHAEKNWFV GLKKNGSCKR  120
GPRTHYGQKA ILFLPLPVSS D                                           141

SEQ ID NO: 24        moltype = AA  length = 145
FEATURE              Location/Qualifiers
REGION               1..145
                     note = Description of Artificial Sequence: Synthetic
                      polypeptide
source               1..145
                     mol_type = protein
                     organism = synthetic construct
SEQUENCE: 24
ALTEKFNLPP GNYKKPKLLY SSNGGHFLRI LPDGTVDGTR DRSDQHIQLQ LSAESVGEVY  60
IKSTETGQYL CMDTDGLLYG SQTPNEECLF LERLEENHYN TYISKKHAEK NWFVGLKKNG  120
SVKRGPRTHY GQKAILFLPL PVSSD                                       145

SEQ ID NO: 25        moltype = AA  length = 144
FEATURE              Location/Qualifiers
REGION               1..144
                     note = Description of Artificial Sequence: Synthetic
                      polypeptide
source               1..144
                     mol_type = protein
                     organism = synthetic construct
SEQUENCE: 25
LTEKFNLPPG NYKKPKLLYS SNGGHFLRIL PDGTVDGTRD RSDQHIQLQL SAESVGEVYI  60
KSTETGQYLC MDTDGLLYGS QTPNEECLFL ERLEENHYNT YISKKHAEKN WFVGLKKNGS  120
VKRGPRTHYG QKAILFLPLP VSSD                                        144

SEQ ID NO: 26        moltype = AA  length = 143
FEATURE              Location/Qualifiers
REGION               1..143
                     note = Description of Artificial Sequence: Synthetic
                      polypeptide
source               1..143
                     mol_type = protein
                     organism = synthetic construct
SEQUENCE: 26
TEKFNLPPGN YKKPKLLYSS NGGHFLRILP DGTVDGTRDR SDQHIQLQLS AESVGEVYIK  60
STETGQYLCM DTDGLLYGSQ TPNEECLFLE RLEENHYNTY ISKKHAEKNW FVGLKKNGSV  120
KRGPRTHYGQ KAILFLPLPV SSD                                         143

SEQ ID NO: 27        moltype = AA  length = 142
FEATURE              Location/Qualifiers
REGION               1..142
                     note = Description of Artificial Sequence: Synthetic
                      polypeptide
source               1..142
                     mol_type = protein
                     organism = synthetic construct
SEQUENCE: 27
EKFNLPPGNY KKPKLLYSSN GGHFLRILPD GTVDGTRDRS DQHIQLQLSA ESVGEVYIKS  60
TETGQYLCMD TDGLLYGSQT PNEECLFLER LEENHYNTYI SKKHAEKNWF VGLKKNGSVK  120
RGPRTHYGQK AILFLPLPVS SD                                          142

SEQ ID NO: 28        moltype = AA  length = 141
FEATURE              Location/Qualifiers
```

```
REGION                  1..141
                        note = Description of Artificial Sequence: Synthetic
                         polypeptide
source                  1..141
                        mol_type = protein
                        organism = synthetic construct
SEQUENCE: 28
KFNLPPGNYK KPKLLYSSNG GHFLRILPDG TVDGTRDRSD QHIQLQLSAE SVGEVYIKST  60
ETGQYLCMDT DGLLYGSQTP NEECLFLERL EENHYNTYIS KKHAEKNWFV GLKKNGSVKR  120
GPRTHYGQKA ILFLPLPVSS D                                            141

SEQ ID NO: 29           moltype = AA  length = 139
FEATURE                 Location/Qualifiers
REGION                  1..139
                        note = Description of Artificial Sequence: Synthetic
                         polypeptide
source                  1..139
                        mol_type = protein
                        organism = synthetic construct
SEQUENCE: 29
NLPPGNYKKP KLLYCSNGGH FLRILPDGTV DGTRDRSDQH IQLQLSAESV GEVYIKSTET  60
GQYLAMDTDG LLYGSQTPNE ECLFLERLEE NHYNTYISKK HAEKNWFVGL KKNGSCKRGP  120
RTHYGQKAIL FLPLPVSSD                                               139

SEQ ID NO: 30           moltype = AA  length = 138
FEATURE                 Location/Qualifiers
REGION                  1..138
                        note = Description of Artificial Sequence: Synthetic
                         polypeptide
source                  1..138
                        mol_type = protein
                        organism = synthetic construct
SEQUENCE: 30
LPPGNYKKPK LLYCSNGGHF LRILPDGTVD GTRDRSDQHI QLQLSAESVG EVYIKSTETG  60
QYLAMDTDGL LYGSQTPNEE CLFLERLEEN HYNTYISKKH AEKNWFVGLK KNGSCKRGPR  120
THYGQKAILF LPLPVSSD                                                138

SEQ ID NO: 31           moltype = AA  length = 137
FEATURE                 Location/Qualifiers
REGION                  1..137
                        note = Description of Artificial Sequence: Synthetic
                         polypeptide
source                  1..137
                        mol_type = protein
                        organism = synthetic construct
SEQUENCE: 31
PPGNYKKPKL LYCSNGGHFL RILPDGTVDG TRDRSDQHIQ LQLSAESVGE VYIKSTETGQ  60
YLAMDTDGLL YGSQTPNEEC LFLERLEENH YNTYISKKHA EKNWFVGLKK NGSCKRGPRT  120
HYGQKAILFL PLPVSSD                                                 137

SEQ ID NO: 32           moltype = AA  length = 136
FEATURE                 Location/Qualifiers
REGION                  1..136
                        note = Description of Artificial Sequence: Synthetic
                         polypeptide
source                  1..136
                        mol_type = protein
                        organism = synthetic construct
SEQUENCE: 32
PGNYKKPKLL YCSNGGHFLR ILPDGTVDGT RDRSDQHIQL QLSAESVGEV YIKSTETGQY  60
LAMDTDGLLY GSQTPNEECL FLERLEENHY NTYISKKHAE KNWFVGLKKN GSCKRGPRTH  120
YGQKAILFLP LPVSSD                                                  136

SEQ ID NO: 33           moltype = AA  length = 139
FEATURE                 Location/Qualifiers
REGION                  1..139
                        note = Description of Artificial Sequence: Synthetic
                         polypeptide
source                  1..139
                        mol_type = protein
                        organism = synthetic construct
SEQUENCE: 33
NLPPGNYKKP KLLYSSNGGH FLRILPDGTV DGTRDRSDQH IQLQLSAESV GEVYIKSTET  60
GQYLCMDTDG LLYGSQTPNE ECLFLERLEE NHYNTYISKK HAEKNWFVGL KKNGSVKRGP  120
RTHYGQKAIL FLPLPVSSD                                               139

SEQ ID NO: 34           moltype = AA  length = 138
FEATURE                 Location/Qualifiers
REGION                  1..138
```

```
                          note = Description of Artificial Sequence: Synthetic
                           polypeptide
source                    1..138
                          mol_type = protein
                          organism = synthetic construct
SEQUENCE: 34
LPPGNYKKPK LLYSSNGGHF LRILPDGTVD GTRDRSDQHI QLQLSAESVG EVYIKSTETG 60
QYLCMDTDGL LYGSQTPNEE CLFLERLEEN HYNTYISKKH AEKNWFVGLK KNGSVKRGPR 120
THYGQKAILF LPLPVSSD                                              138

SEQ ID NO: 35            moltype = AA  length = 137
FEATURE                  Location/Qualifiers
REGION                   1..137
                          note = Description of Artificial Sequence: Synthetic
                           polypeptide
source                    1..137
                          mol_type = protein
                          organism = synthetic construct
SEQUENCE: 35
PPGNYKKPKL LYSSNGGHFL RILPDGTVDG TRDRSDQHIQ LQLSAESVGE VYIKSTETGQ 60
YLCMDTDGLL YGSQTPNEEC LFLERLEENH YNTYISKKHA EKNWFVGLKK NGSVKRGPRT 120
HYGQKAILFL PLPVSSD                                               137

SEQ ID NO: 36            moltype = AA  length = 136
FEATURE                  Location/Qualifiers
REGION                   1..136
                          note = Description of Artificial Sequence: Synthetic
                           polypeptide
source                    1..136
                          mol_type = protein
                          organism = synthetic construct
SEQUENCE: 36
PGNYKKPKLL YSSNGGHFLR ILPDGTVDGT RDRSDQHIQL QLSAESVGEV YIKSTETGQY 60
LCMDTDGLLY GSQTPNEECL FLERLEENHY NTYISKKHAE KNWFVGLKKN GSVKRGPRTH 120
YGQKAILFLP LPVSSD                                                136

SEQ ID NO: 37            moltype = AA  length = 140
FEATURE                  Location/Qualifiers
REGION                   1..140
                          note = Description of Artificial Sequence: Synthetic
                           polypeptide
source                    1..140
                          mol_type = protein
                          organism = synthetic construct
SEQUENCE: 37
MNLPPGNYKK PKLLYCSNGG HFLRILPDGT VDGTRDRSDQ HIQLQLSAES VGEVYIKSTE 60
TGQYLAMDTD GLLYGSQTPN EECLFLERLE ENHYNTYISK KHAEKNWFVG LKKNGSCKRG 120
PRTHYGQKAI LFLPLPVSSD                                            140

SEQ ID NO: 38            moltype = AA  length = 139
FEATURE                  Location/Qualifiers
REGION                   1..139
                          note = Description of Artificial Sequence: Synthetic
                           polypeptide
source                    1..139
                          mol_type = protein
                          organism = synthetic construct
SEQUENCE: 38
MLPPGNYKKP KLLYCSNGGH FLRILPDGTV DGTRDRSDQH IQLQLSAESV GEVYIKSTET 60
GQYLAMDTDG LLYGSQTPNE ECLFLERLEE NHYNTYISKK HAEKNWFVGL KKNGSCKRGP 120
RTHYGQKAIL FLPLPVSSD                                             139

SEQ ID NO: 39            moltype = AA  length = 138
FEATURE                  Location/Qualifiers
REGION                   1..138
                          note = Description of Artificial Sequence: Synthetic
                           polypeptide
source                    1..138
                          mol_type = protein
                          organism = synthetic construct
SEQUENCE: 39
MPPGNYKKPK LLYCSNGGHF LRILPDGTVD GTRDRSDQHI QLQLSAESVG EVYIKSTETG 60
QYLAMDTDGL LYGSQTPNEE CLFLERLEEN HYNTYISKKH AEKNWFVGLK KNGSCKRGPR 120
THYGQKAILF LPLPVSSD                                              138

SEQ ID NO: 40            moltype = AA  length = 137
FEATURE                  Location/Qualifiers
REGION                   1..137
                          note = Description of Artificial Sequence: Synthetic
```

```
                          polypeptide
source                    1..137
                          mol_type = protein
                          organism = synthetic construct
SEQUENCE: 40
MPGNYKKPKL LYCSNGGHFL RILPDGTVDG TRDRSDQHIQ LQLSAESVGE VYIKSTETGQ  60
YLAMDTDGLL YGSQTPNEEC LFLERLEENH YNTYISKKHA EKNWFVGLKK NGSCKRGPRT  120
HYGQKAILFL PLPVSSD                                                 137

SEQ ID NO: 41             moltype = AA  length = 140
FEATURE                   Location/Qualifiers
REGION                    1..140
                          note = Description of Artificial Sequence: Synthetic
                          polypeptide
source                    1..140
                          mol_type = protein
                          organism = synthetic construct
SEQUENCE: 41
MNLPPGNYKK PKLLYSSNGG HFLRILPDGT VDGTRDRSDQ HIQLQLSAES VGEVYIKSTE  60
TGQYLCMDTD GLLYGSQTPN EECLFLERLE ENHYNTYISK KHAEKNWFVG LKKNGSVKRG  120
PRTHYGQKAI LFLPLPVSSD                                              140

SEQ ID NO: 42             moltype = AA  length = 139
FEATURE                   Location/Qualifiers
REGION                    1..139
                          note = Description of Artificial Sequence: Synthetic
                          polypeptide
source                    1..139
                          mol_type = protein
                          organism = synthetic construct
SEQUENCE: 42
MLPPGNYKKP KLLYSSNGGH FLRILPDGTV DGTRDRSDQH IQLQLSAESV GEVYIKSTET  60
GQYLCMDTDG LLYGSQTPNE ECLFLERLEE NHYNTYISKK HAEKNWFVGL KKNGSVKRGP  120
RTHYGQKAIL FLPLPVSSD                                               139

SEQ ID NO: 43             moltype = AA  length = 138
FEATURE                   Location/Qualifiers
REGION                    1..138
                          note = Description of Artificial Sequence: Synthetic
                          polypeptide
source                    1..138
                          mol_type = protein
                          organism = synthetic construct
SEQUENCE: 43
MPPGNYKKPK LLYSSNGGHF LRILPDGTVD GTRDRSDQHI QLQLSAESVG EVYIKSTETG  60
QYLCMDTDGL LYGSQTPNEE CLFLERLEEN HYNTYISKKH AEKNWFVGLK KNGSVKRGPR  120
THYGQKAILF LPLPVSSD                                                138

SEQ ID NO: 44             moltype = AA  length = 137
FEATURE                   Location/Qualifiers
REGION                    1..137
                          note = Description of Artificial Sequence: Synthetic
                          polypeptide
source                    1..137
                          mol_type = protein
                          organism = synthetic construct
SEQUENCE: 44
MPGNYKKPKL LYSSNGGHFL RILPDGTVDG TRDRSDQHIQ LQLSAESVGE VYIKSTETGQ  60
YLCMDTDGLL YGSQTPNEEC LFLERLEENH YNTYISKKHA EKNWFVGLKK NGSVKRGPRT  120
HYGQKAILFL PLPVSSD                                                 137

SEQ ID NO: 45             moltype = AA  length = 145
FEATURE                   Location/Qualifiers
REGION                    1..145
                          note = Description of Artificial Sequence: Synthetic
                          polypeptide
source                    1..145
                          mol_type = protein
                          organism = synthetic construct
SEQUENCE: 45
MALTEKNLPP GNYKKPKLLY CSNGGHFLRI LPDGTVDGTR DRSDQHIQLQ LSAESVGEVY  60
IKSTETGQYL AMDTDGLLYG SQTPNEECLF LERLEENHYN TYISKKHAEK NWFVGLKKNG  120
SCKRGPRTHY GQKAILFLPL PVSSD                                        145

SEQ ID NO: 46             moltype = AA  length = 144
FEATURE                   Location/Qualifiers
REGION                    1..144
                          note = Description of Artificial Sequence: Synthetic
                          polypeptide
```

```
source                  1..144
                        mol_type = protein
                        organism = synthetic construct
SEQUENCE: 46
MALTEKLPPG NYKKPKLLYS SNGGHFLRIL PDGTVDGTRD RSDQHIQLQL SAESVGEVYI  60
KSTETGQYLC MDTDGLLYGS QTPNEECLFL ERLEENHYNT YISKKHAEKN WFVGLKKNGS  120
VKRGPRTHYG QKAILFLPLP VSSD                                          144

SEQ ID NO: 47           moltype = AA  length = 144
FEATURE                 Location/Qualifiers
REGION                  1..144
                        note = Description of Artificial Sequence: Synthetic
                         polypeptide
source                  1..144
                        mol_type = protein
                        organism = synthetic construct
SEQUENCE: 47
MALTEKPPGG NYKKPKLLYC SNGGHFLRIL PDGTVDGTRD RSDQHIQLQL SAESVGEVYI  60
KSTETGQYLA MDTDGLLYGS QTPNEECLFL ERLEENHYNT YISKKHAEKN WFVGLKKNGS  120
CKRGPRTHYG QKAILFLPLP VSSD                                          144

SEQ ID NO: 48           moltype = AA  length = 142
FEATURE                 Location/Qualifiers
REGION                  1..142
                        note = Description of Artificial Sequence: Synthetic
                         polypeptide
source                  1..142
                        mol_type = protein
                        organism = synthetic construct
SEQUENCE: 48
MALTEKPGNY KKPKLLYCSN GGHFLRILPD GTVDGTRDRS DQHIQLQLSA ESVGEVYIKS  60
TETGQYLAMD TDGLLYGSQT PNEECLFLER LEENHYNTYI SKKHAEKNWF VGLKKNGSCK  120
RGPRTHYGQK AILFLPLPVS SD                                            142

SEQ ID NO: 49           moltype = AA  length = 145
FEATURE                 Location/Qualifiers
REGION                  1..145
                        note = Description of Artificial Sequence: Synthetic
                         polypeptide
source                  1..145
                        mol_type = protein
                        organism = synthetic construct
SEQUENCE: 49
MLTEKFNLPP GNYKKPKLLY CSNGGHFLRI LPDGTVDGTR DRSDQHIQLQ LSAESVGEVY  60
IKSTETGQYL AMDTDGLLYG SQTPNEECLF LERLEENHYN TYISKKHAEK NWFVGLKKNG  120
SCKRGPRTHY GQKAILFLPL PVSSD                                         145

SEQ ID NO: 50           moltype = AA  length = 144
FEATURE                 Location/Qualifiers
REGION                  1..144
                        note = Description of Artificial Sequence: Synthetic
                         polypeptide
source                  1..144
                        mol_type = protein
                        organism = synthetic construct
SEQUENCE: 50
MLTEKNLPPG NYKKPKLLYC SNGGHFLRIL PDGTVDGTRD RSDQHIQLQL SAESVGEVYI  60
KSTETGQYLA MDTDGLLYGS QTPNEECLFL ERLEENHYNT YISKKHAEKN WFVGLKKNGS  120
CKRGPRTHYG QKAILFLPLP VSSD                                          144

SEQ ID NO: 51           moltype = AA  length = 143
FEATURE                 Location/Qualifiers
REGION                  1..143
                        note = Description of Artificial Sequence: Synthetic
                         polypeptide
source                  1..143
                        mol_type = protein
                        organism = synthetic construct
SEQUENCE: 51
MLTEKLPPGN YKKPKLLYCS NGGHFLRILP DGTVDGTRDR SDQHIQLQLS AESVGEVYIK  60
STETGQYLAM DTDGLLYGSQ TPNEECLFLE RLEENHYNTY ISKKHAEKNW FVGLKKNGSC  120
KRGPRTHYGQ KAILFLPLPV SSD                                           143

SEQ ID NO: 52           moltype = AA  length = 142
FEATURE                 Location/Qualifiers
REGION                  1..142
                        note = Description of Artificial Sequence: Synthetic
                         polypeptide
source                  1..142
```

```
                             mol_type = protein
                             organism = synthetic construct
SEQUENCE: 52
MLTEKPPGNY KKPKLLYCSN GGHFLRILPD GTVDGTRDRS DQHIQLQLSA ESVGEVYIKS  60
TETGQYLAMD TDGLLYGSQT PNEECLFLER LEENHYNTYI SKKHAEKNWF VGLKKNGSCK  120
RGPRTHYGQK AILFLPLPVS SD                                          142

SEQ ID NO: 53           moltype = AA   length = 141
FEATURE                 Location/Qualifiers
REGION                  1..141
                        note = Description of Artificial Sequence: Synthetic
                         polypeptide
source                  1..141
                        mol_type = protein
                        organism = synthetic construct
SEQUENCE: 53
MLTEKPPGNYK KPKLLYCSNG GHFLRILPDG TVDGTRDRSD QHIQLQLSAE SVGEVYIKST  60
ETGQYLAMDT DGLLYGSQTP NEECLFLERL EENHYNTYIS KKHAEKNWFV GLKKNGSCKR  120
GPRTHYGQKA ILFLPLPVSS D                                           141

SEQ ID NO: 54           moltype = AA   length = 144
FEATURE                 Location/Qualifiers
REGION                  1..144
                        note = Description of Artificial Sequence: Synthetic
                         polypeptide
source                  1..144
                        mol_type = protein
                        organism = synthetic construct
SEQUENCE: 54
MTEKFNLPPG NYKKPKLLYC SNGGHFLRIL PDGTVDGTRD RSDQHIQLQL SAESVGEVYI  60
KSTETGQYLA MDTDGLLYGS QTPNEECLFL ERLEENHYNT YISKKHAEKN WFVGLKKNGS  120
CKRGPRTHYG QKAILFLPLP VSSD                                        144

SEQ ID NO: 55           moltype = AA   length = 143
FEATURE                 Location/Qualifiers
REGION                  1..143
                        note = Description of Artificial Sequence: Synthetic
                         polypeptide
source                  1..143
                        mol_type = protein
                        organism = synthetic construct
SEQUENCE: 55
MTEKNLPPGN YKKPKLLYCS NGGHFLRILP DGTVDGTRDR SDQHIQLQLS AESVGEVYIK  60
STETGQYLAM DTDGLLYGSQ TPNEECLFLE RLEENHYNTY ISKKHAEKNW FVGLKKNGSC  120
KRGPRTHYGQ KAILFLPLPV SSD                                         143

SEQ ID NO: 56           moltype = AA   length = 142
FEATURE                 Location/Qualifiers
REGION                  1..142
                        note = Description of Artificial Sequence: Synthetic
                         polypeptide
source                  1..142
                        mol_type = protein
                        organism = synthetic construct
SEQUENCE: 56
MTEKLPPGNY KKPKLLYCSN GGHFLRILPD GTVDGTRDRS DQHIQLQLSA ESVGEVYIKS  60
TETGQYLAMD TDGLLYGSQT PNEECLFLER LEENHYNTYI SKKHAEKNWF VGLKKNGSCK  120
RGPRTHYGQK AILFLPLPVS SD                                          142

SEQ ID NO: 57           moltype = AA   length = 141
FEATURE                 Location/Qualifiers
REGION                  1..141
                        note = Description of Artificial Sequence: Synthetic
                         polypeptide
source                  1..141
                        mol_type = protein
                        organism = synthetic construct
SEQUENCE: 57
MTEKPPGNYK KPKLLYCSNG GHFLRILPDG TVDGTRDRSD QHIQLQLSAE SVGEVYIKST  60
ETGQYLAMDT DGLLYGSQTP NEECLFLERL EENHYNTYIS KKHAEKNWFV GLKKNGSCKR  120
GPRTHYGQKA ILFLPLPVSS D                                           141

SEQ ID NO: 58           moltype = AA   length = 140
FEATURE                 Location/Qualifiers
REGION                  1..140
                        note = Description of Artificial Sequence: Synthetic
                         polypeptide
source                  1..140
                        mol_type = protein
```

```
organism = synthetic construct
SEQUENCE: 58
MTEKPGNYKK PKLLYCSNGG HFLRILPDGT VDGTRDRSDQ HIQLQLSAES VGEVYIKSTE  60
TGQYLAMDTD GLLYGSQTPN EECLFLERLE ENHYNTYISK KHAEKNWFVG LKKNGSCKRG  120
PRTHYGQKAI LFLPLPVSSD                                             140

SEQ ID NO: 59          moltype = AA  length = 143
FEATURE                Location/Qualifiers
REGION                 1..143
                       note = Description of Artificial Sequence: Synthetic
                        polypeptide
source                 1..143
                       mol_type = protein
                       organism = synthetic construct
SEQUENCE: 59
MEKFNLPPGN YKKPKLLYCS NGGHFLRILP DGTVDGTRDR SDQHIQLQLS AESVGEVYIK  60
STETGQYLAM DTDGLLYGSQ TPNEECLFLE RLEENHYNTY ISKKHAEKNW FVGLKKNGSC  120
KRGPRTHYGQ KAILFLPLPV SSD                                         143

SEQ ID NO: 60          moltype = AA  length = 142
FEATURE                Location/Qualifiers
REGION                 1..142
                       note = Description of Artificial Sequence: Synthetic
                        polypeptide
source                 1..142
                       mol_type = protein
                       organism = synthetic construct
SEQUENCE: 60
MEKNLPPGNY KKPKLLYCSN GGHFLRILPD GTVDGTRDRS DQHIQLQLSA ESVGEVYIKS  60
TETGQYLAMD TDGLLYGSQT PNEECLFLER LEENHYNTYI SKKHAEKNWF VGLKKNGSCK  120
RGPRTHYGQK AILFLPLPVS SD                                          142

SEQ ID NO: 61          moltype = AA  length = 141
FEATURE                Location/Qualifiers
REGION                 1..141
                       note = Description of Artificial Sequence: Synthetic
                        polypeptide
source                 1..141
                       mol_type = protein
                       organism = synthetic construct
SEQUENCE: 61
MEKLPPGNYK KPKLLYCSNG GHFLRILPDG TVDGTRDRSD QHIQLQLSAE SVGEVYIKST  60
ETGQYLAMDT DGLLYGSQTP NEECLFLERL EENHYNTYIS KKHAEKNWFV GLKKNGSCKR  120
GPRTHYGQKA ILFLPLPVSS D                                           141

SEQ ID NO: 62          moltype = AA  length = 140
FEATURE                Location/Qualifiers
REGION                 1..140
                       note = Description of Artificial Sequence: Synthetic
                        polypeptide
source                 1..140
                       mol_type = protein
                       organism = synthetic construct
SEQUENCE: 62
MEKPPGNYKK PKLLYCSNGG HFLRILPDGT VDGTRDRSDQ HIQLQLSAES VGEVYIKSTE  60
TGQYLAMDTD GLLYGSQTPN EECLFLERLE ENHYNTYISK KHAEKNWFVG LKKNGSCKRG  120
PRTHYGQKAI LFLPLPVSSD                                             140

SEQ ID NO: 63          moltype = AA  length = 139
FEATURE                Location/Qualifiers
REGION                 1..139
                       note = Description of Artificial Sequence: Synthetic
                        polypeptide
source                 1..139
                       mol_type = protein
                       organism = synthetic construct
SEQUENCE: 63
MEKPGNYKKP KLLYCSNGGH FLRILPDGTV DGTRDRSDQH IQLQLSAESV GEVYIKSTET  60
GQYLAMDTDG LLYGSQTPNE ECLFLERLEE NHYNTYISKK HAEKNWFVGL KKNGSCKRGP  120
RTHYGQKAIL FLPLPVSSD                                              139

SEQ ID NO: 64          moltype = AA  length = 142
FEATURE                Location/Qualifiers
REGION                 1..142
                       note = Description of Artificial Sequence: Synthetic
                        polypeptide
source                 1..142
                       mol_type = protein
                       organism = synthetic construct
```

```
SEQUENCE: 64
MKFNLPPGNY KKPKLLYCSN GGHFLRILPD GTVDGTRDRS DQHIQLQLSA ESVGEVYIKS   60
TETGQYLAMD TDGLLYGSQT PNEECLFLER LEENHYNTYI SKKHAEKNWF VGLKKNGSCK  120
RGPRTHYGQK AILFLPLPVS SD                                           142

SEQ ID NO: 65           moltype = AA  length = 141
FEATURE                 Location/Qualifiers
REGION                  1..141
                        note = Description of Artificial Sequence: Synthetic
                         polypeptide
source                  1..141
                        mol_type = protein
                        organism = synthetic construct
SEQUENCE: 65
MKNLPPGNYK KPKLLYCSNG GHFLRILPDG TVDGTRDRSD QHIQLQLSAE SVGEVYIKST   60
ETGQYLAMDT DGLLYGSQTP NEECLFLERL EENHYNTYIS KKHAEKNWFV GLKKNGSCKR  120
GPRTHYGQKA ILFLPLPVSS D                                            141

SEQ ID NO: 66           moltype = AA  length = 140
FEATURE                 Location/Qualifiers
REGION                  1..140
                        note = Description of Artificial Sequence: Synthetic
                         polypeptide
source                  1..140
                        mol_type = protein
                        organism = synthetic construct
SEQUENCE: 66
MKLPPGNYKK PKLLYCSNGG HFLRILPDGT VDGTRDRSDQ HIQLQLSAES VGEVYIKSTE   60
TGQYLAMDTD GLLYGSQTPN EECLFLERLE ENHYNTYISK KHAEKNWFVG LKKNGSCKRG  120
PRTHYGQKAI LFLPLPVSSD                                              140

SEQ ID NO: 67           moltype = AA  length = 139
FEATURE                 Location/Qualifiers
REGION                  1..139
                        note = Description of Artificial Sequence: Synthetic
                         polypeptide
source                  1..139
                        mol_type = protein
                        organism = synthetic construct
SEQUENCE: 67
MKPPGNYKKP KLLYCSNGGH FLRILPDGTV DGTRDRSDQH IQLQLSAESV GEVYIKSTET   60
GQYLAMDTDG LLYGSQTPNE ECLFLERLEE NHYNTYISKK HAEKNWFVGL KKNGSCKRGP  120
RTHYGQKAIL FLPLPVSSD                                               139

SEQ ID NO: 68           moltype = AA  length = 138
FEATURE                 Location/Qualifiers
REGION                  1..138
                        note = Description of Artificial Sequence: Synthetic
                         polypeptide
source                  1..138
                        mol_type = protein
                        organism = synthetic construct
SEQUENCE: 68
MKPGNYKKPK LLYCSNGGHF LRILPDGTVD GTRDRSDQHI QLQLSAESVG EVYIKSTETG   60
QYLAMDTDGL LYGSQTPNEE CLFLERLEEN HYNTYISKKH AEKNWFVGLK KNGSCKRGPR  120
THYGQKAILF LPLPVSSD                                                138

SEQ ID NO: 69           moltype = AA  length = 144
FEATURE                 Location/Qualifiers
REGION                  1..144
                        note = Description of Artificial Sequence: Synthetic
                         polypeptide
source                  1..144
                        mol_type = protein
                        organism = synthetic construct
SEQUENCE: 69
ALTEKNLPPG NYKKPKLLYC SNGGHFLRIL PDGTVDGTRD RSDQHIQLQL SAESVGEVYI   60
KSTETGQYLA MDTDGLLYGS QTPNEECLFL ERLEENHYNT YISKKHAEKN WFVGLKKNGS  120
CKRGPRTHYG QKAILFLPLP VSSD                                         144

SEQ ID NO: 70           moltype = AA  length = 143
FEATURE                 Location/Qualifiers
REGION                  1..143
                        note = Description of Artificial Sequence: Synthetic
                         polypeptide
source                  1..143
                        mol_type = protein
                        organism = synthetic construct
SEQUENCE: 70
```

-continued

```
ALTEKLPPGN YKKPKLLYCS NGGHFLRILP DGTVDGTRDR SDQHIQLQLS AESVGEVYIK  60
STETGQYLAM DTDGLLYGSQ TPNEECLFLE RLEENHYNTY ISKKHAEKNW FVGLKKNGSC  120
KRGPRTHYGQ KAILFLPLPV SSD                                          143

SEQ ID NO: 71             moltype = AA  length = 142
FEATURE                   Location/Qualifiers
REGION                    1..142
                          note = Description of Artificial Sequence: Synthetic
                           polypeptide
source                    1..142
                          mol_type = protein
                          organism = synthetic construct
SEQUENCE: 71
ALTEKPPGNY KKPKLLYCSN GGHFLRILPD GTVDGTRDRS DQHIQLQLSA ESVGEVYIKS  60
TETGQYLAMD TDGLLYGSQT PNEECLFLER LEENHYNTYI SKKHAEKNWF VGLKKNGSCK  120
RGPRTHYGQK AILFLPLPVS SD                                           142

SEQ ID NO: 72             moltype = AA  length = 141
FEATURE                   Location/Qualifiers
REGION                    1..141
                          note = Description of Artificial Sequence: Synthetic
                           polypeptide
source                    1..141
                          mol_type = protein
                          organism = synthetic construct
SEQUENCE: 72
ALTEKPGNYK KPKLLYCSNG GHFLRILPDG TVDGTRDRSD QHIQLQLSAE SVGEVYIKST  60
ETGQYLAMDT DGLLYGSQTP NEECLFLERL EENHYNTYIS KKHAEKNWFV GLKKNGSCKR  120
GPRTHYGQKA ILFLPLPVSS D                                            141

SEQ ID NO: 73             moltype = AA  length = 144
FEATURE                   Location/Qualifiers
REGION                    1..144
                          note = Description of Artificial Sequence: Synthetic
                           polypeptide
source                    1..144
                          mol_type = protein
                          organism = synthetic construct
SEQUENCE: 73
LTEKFNLPPG NYKKPKLLYC SNGGHFLRIL PDGTVDGTRD RSDQHIQLQL SAESVGEVYI  60
KSTETGQYLA MDTDGLLYGS QTPNEECLFL ERLEENHYNT YISKKHAEKN WFVGLKKNGS  120
CKRGPRTHYG QKAILFLPLP VSSD                                         144

SEQ ID NO: 74             moltype = AA  length = 143
FEATURE                   Location/Qualifiers
REGION                    1..143
                          note = Description of Artificial Sequence: Synthetic
                           polypeptide
source                    1..143
                          mol_type = protein
                          organism = synthetic construct
SEQUENCE: 74
LTEKNLPPGN YKKPKLLYCS NGGHFLRILP DGTVDGTRDR SDQHIQLQLS AESVGEVYIK  60
STETGQYLAM DTDGLLYGSQ TPNEECLFLE RLEENHYNTY ISKKHAEKNW FVGLKKNGSC  120
KRGPRTHYGQ KAILFLPLPV SSD                                          143

SEQ ID NO: 75             moltype = AA  length = 142
FEATURE                   Location/Qualifiers
REGION                    1..142
                          note = Description of Artificial Sequence: Synthetic
                           polypeptide
source                    1..142
                          mol_type = protein
                          organism = synthetic construct
SEQUENCE: 75
LTEKLPPGNY KKPKLLYCSN GGHFLRILPD GTVDGTRDRS DQHIQLQLSA ESVGEVYIKS  60
TETGQYLAMD TDGLLYGSQT PNEECLFLER LEENHYNTYI SKKHAEKNWF VGLKKNGSCK  120
RGPRTHYGQK AILFLPLPVS SD                                           142

SEQ ID NO: 76             moltype = AA  length = 141
FEATURE                   Location/Qualifiers
REGION                    1..141
                          note = Description of Artificial Sequence: Synthetic
                           polypeptide
source                    1..141
                          mol_type = protein
                          organism = synthetic construct
SEQUENCE: 76
LTEKPPGNYK KPKLLYCSNG GHFLRILPDG TVDGTRDRSD QHIQLQLSAE SVGEVYIKST  60
```

```
ETGQYLAMDT DGLLYGSQTP NEECLFLERL EENHYNTYIS KKHAEKNWFV GLKKNGSCKR   120
GPRTHYGQKA ILFLPLPVSS D                                            141

SEQ ID NO: 77            moltype = AA  length = 140
FEATURE                  Location/Qualifiers
REGION                   1..140
                         note = Description of Artificial Sequence: Synthetic
                          polypeptide
source                   1..140
                         mol_type = protein
                         organism = synthetic construct
SEQUENCE: 77
LTEKPGNYKK PKLLYCSNGG HFLRILPDGT VDGTRDRSDQ HIQLQLSAES VGEVYIKSTE   60
TGQYLAMDTD GLLYGSQTPN EECLFLERLE ENHYNTYISK KHAEKNWFVG LKKNGSCKRG   120
PRTHYGQKAI LFLPLPVSSD                                              140

SEQ ID NO: 78            moltype = AA  length = 143
FEATURE                  Location/Qualifiers
REGION                   1..143
                         note = Description of Artificial Sequence: Synthetic
                          polypeptide
source                   1..143
                         mol_type = protein
                         organism = synthetic construct
SEQUENCE: 78
TEKFNLPPGN YKKPKLLYCS NGGHFLRILP DGTVDGTRDR SDQHIQLQLS AESVGEVYIK   60
STETGQYLAM DTDGLLYGSQ TPNEECLFLE RLEENHYNTY ISKKHAEKNW FVGLKKNGSC   120
KRGPRTHYGQ KAILFLPLPV SSD                                          143

SEQ ID NO: 79            moltype = AA  length = 142
FEATURE                  Location/Qualifiers
REGION                   1..142
                         note = Description of Artificial Sequence: Synthetic
                          polypeptide
source                   1..142
                         mol_type = protein
                         organism = synthetic construct
SEQUENCE: 79
TEKNLPPGNY KKPKLLYCSN GGHFLRILPD GTVDGTRDRS DQHIQLQLSA ESVGEVYIKS   60
TETGQYLAMD TDGLLYGSQT PNEECLFLER LEENHYNTYI SKKHAEKNWF VGLKKNGSCK   120
RGPRTHYGQK AILFLPLPVS SD                                           142

SEQ ID NO: 80            moltype = AA  length = 141
FEATURE                  Location/Qualifiers
REGION                   1..141
                         note = Description of Artificial Sequence: Synthetic
                          polypeptide
source                   1..141
                         mol_type = protein
                         organism = synthetic construct
SEQUENCE: 80
TEKLPPGNYK KPKLLYCSNG GHFLRILPDG TVDGTRDRSD QHIQLQLSAE SVGEVYIKST   60
ETGQYLAMDT DGLLYGSQTP NEECLFLERL EENHYNTYIS KKHAEKNWFV GLKKNGSCKR   120
GPRTHYGQKA ILFLPLPVSS D                                            141

SEQ ID NO: 81            moltype = AA  length = 140
FEATURE                  Location/Qualifiers
REGION                   1..140
                         note = Description of Artificial Sequence: Synthetic
                          polypeptide
source                   1..140
                         mol_type = protein
                         organism = synthetic construct
SEQUENCE: 81
TEKPPGNYKK PKLLYCSNGG HFLRILPDGT VDGTRDRSDQ HIQLQLSAES VGEVYIKSTE   60
TGQYLAMDTD GLLYGSQTPN EECLFLERLE ENHYNTYISK KHAEKNWFVG LKKNGSCKRG   120
PRTHYGQKAI LFLPLPVSSD                                              140

SEQ ID NO: 82            moltype = AA  length = 139
FEATURE                  Location/Qualifiers
REGION                   1..139
                         note = Description of Artificial Sequence: Synthetic
                          polypeptide
source                   1..139
                         mol_type = protein
                         organism = synthetic construct
SEQUENCE: 82
TEKPGNYKKP KLLYCSNGGH FLRILPDGTV DGTRDRSDQH IQLQLSAESV GEVYIKSTET   60
GQYLAMDTDG LLYGSQTPNE ECLFLERLEE NHYNTYISKK HAEKNWFVGL KKNGSCKRGP   120
```

-continued

```
RTHYGQKAIL FLPLPVSSD                                                   139

SEQ ID NO: 83            moltype = AA  length = 142
FEATURE                  Location/Qualifiers
REGION                   1..142
                         note = Description of Artificial Sequence: Synthetic
                          polypeptide
source                   1..142
                         mol_type = protein
                         organism = synthetic construct
SEQUENCE: 83
EKFNLPPGNY KKPKLLYCSN GGHFLRILPD GTVDGTRDRS DQHIQLQLSA ESVGEVYIKS  60
TETGQYLAMD TDGLLYGSQT PNEECLFLER LEENHYNTYI SKKHAEKNWF VGLKKNGSCK  120
RGPRTHYGQK AILFLPLPVS SD                                            142

SEQ ID NO: 84            moltype = AA  length = 141
FEATURE                  Location/Qualifiers
REGION                   1..141
                         note = Description of Artificial Sequence: Synthetic
                          polypeptide
source                   1..141
                         mol_type = protein
                         organism = synthetic construct
SEQUENCE: 84
EKNLPPGNYK KPKLLYCSNG GHFLRILPDG TVDGTRDRSD QHIQLQLSAE SVGEVYIKST  60
ETGQYLAMDT DGLLYGSQTP NEECLFLERL EENHYNTYIS KKHAEKNWFV GLKKNGSCKR  120
GPRTHYGQKA ILFLPLPVSS D                                             141

SEQ ID NO: 85            moltype = AA  length = 140
FEATURE                  Location/Qualifiers
REGION                   1..140
                         note = Description of Artificial Sequence: Synthetic
                          polypeptide
source                   1..140
                         mol_type = protein
                         organism = synthetic construct
SEQUENCE: 85
EKLPPGNYKK PKLLYCSNGG HFLRILPDGT VDGTRDRSDQ HIQLQLSAES VGEVYIKSTE  60
TGQYLAMDTD GLLYGSQTPN EECLFLERLE ENHYNTYISK KHAEKNWFVG LKKNGSCKRG  120
PRTHYGQKAI LFLPLPVSSD                                               140

SEQ ID NO: 86            moltype = AA  length = 139
FEATURE                  Location/Qualifiers
REGION                   1..139
                         note = Description of Artificial Sequence: Synthetic
                          polypeptide
source                   1..139
                         mol_type = protein
                         organism = synthetic construct
SEQUENCE: 86
EKPPGNYKKP KLLYCSNGGH FLRILPDGTV DGTRDRSDQH IQLQLSAESV GEVYIKSTET  60
GQYLAMDTDG LLYGSQTPNE ECLFLERLEE NHYNTYISKK HAEKNWFVGL KKNGSCKRGP  120
RTHYGQKAIL FLPLPVSSD                                                139

SEQ ID NO: 87            moltype = AA  length = 138
FEATURE                  Location/Qualifiers
REGION                   1..138
                         note = Description of Artificial Sequence: Synthetic
                          polypeptide
source                   1..138
                         mol_type = protein
                         organism = synthetic construct
SEQUENCE: 87
EKPGNYKKPK LLYCSNGGHF LRILPDGTVD GTRDRSDQHI QLQLSAESVG EVYIKSTETG  60
QYLAMDTDGL LYGSQTPNEE CLFLERLEEN HYNTYISKKH AEKNWFVGLK NGSCKRGPR  120
THYGQKAILF LPLPVSSD                                                 138

SEQ ID NO: 88            moltype = AA  length = 141
FEATURE                  Location/Qualifiers
REGION                   1..141
                         note = Description of Artificial Sequence: Synthetic
                          polypeptide
source                   1..141
                         mol_type = protein
                         organism = synthetic construct
SEQUENCE: 88
KFNLPPGNYK KPKLLYCSNG GHFLRILPDG TVDGTRDRSD QHIQLQLSAE SVGEVYIKST  60
ETGQYLAMDT DGLLYGSQTP NEECLFLERL EENHYNTYIS KKHAEKNWFV GLKKNGSCKR  120
GPRTHYGQKA ILFLPLPVSS D                                             141
```

-continued

```
SEQ ID NO: 89           moltype = AA  length = 140
FEATURE                 Location/Qualifiers
REGION                  1..140
                        note = Description of Artificial Sequence: Synthetic
                        polypeptide
source                  1..140
                        mol_type = protein
                        organism = synthetic construct
SEQUENCE: 89
KNLPPGNYKK PKLLYCSNGG HFLRILPDGT VDGTRDRSDQ HIQLQLSAES VGEVYIKSTE  60
TGQYLAMDTD GLLYGSQTPN EECLFLERLE ENHYNTYISK KHAEKNWFVG LKKNGSCKRG  120
PRTHYGQKAI LFLPLPVSSD                                             140

SEQ ID NO: 90           moltype = AA  length = 139
FEATURE                 Location/Qualifiers
REGION                  1..139
                        note = Description of Artificial Sequence: Synthetic
                        polypeptide
source                  1..139
                        mol_type = protein
                        organism = synthetic construct
SEQUENCE: 90
KLPPGNYKKP KLLYCSNGGH FLRILPDGTV DGTRDRSDQH IQLQLSAESV GEVYIKSTET  60
GQYLAMDTDG LLYGSQTPNE ECLFLERLEE NHYNTYISKK HAEKNWFVGL KKNGSCKRGP  120
RTHYGQKAIL FLPLPVSSD                                              139

SEQ ID NO: 91           moltype = AA  length = 138
FEATURE                 Location/Qualifiers
REGION                  1..138
                        note = Description of Artificial Sequence: Synthetic
                        polypeptide
source                  1..138
                        mol_type = protein
                        organism = synthetic construct
SEQUENCE: 91
KPPGNYKKPK LLYCSNGGHF LRILPDGTVD GTRDRSDQHI QLQLSAESVG EVYIKSTETG  60
QYLAMDTDGL LYGSQTPNEE CLFLERLEEN HYNTYISKKH AEKNWFVGLK KNGSCKRGPR  120
THYGQKAILF LPLPVSSD                                               138

SEQ ID NO: 92           moltype = AA  length = 137
FEATURE                 Location/Qualifiers
REGION                  1..137
                        note = Description of Artificial Sequence: Synthetic
                        polypeptide
source                  1..137
                        mol_type = protein
                        organism = synthetic construct
SEQUENCE: 92
KPGNYKKPKL LYCSNGGHFL RILPDGTVDG TRDRSDQHIQ LQLSAESVGE VYIKSTETGQ  60
YLAMDTDGLL YGSQTPNEEC LFLERLEENH YNTYISKKHA EKNWFVGLKK NGSCKRGPRT  120
HYGQKAILFL PLPVSSD                                                137

SEQ ID NO: 93           moltype = AA  length = 144
FEATURE                 Location/Qualifiers
REGION                  1..144
                        note = Description of Artificial Sequence: Synthetic
                        polypeptide
source                  1..144
                        mol_type = protein
                        organism = synthetic construct
SEQUENCE: 93
ALTEKNLPPG NYKKPKLLYS SNGGHFLRIL PDGTVDGTRD RSDQHIQLQL SAESVGEVYI  60
KSTETGQYLC MDTDGLLYGS QTPNEECLFL ERLEENHYNT YISKKHAEKN WFVGLKKNGS  120
VKRGPRTHYG QKAILFLPLP VSSD                                        144

SEQ ID NO: 94           moltype = AA  length = 143
FEATURE                 Location/Qualifiers
REGION                  1..143
                        note = Description of Artificial Sequence: Synthetic
                        polypeptide
source                  1..143
                        mol_type = protein
                        organism = synthetic construct
SEQUENCE: 94
ALTEKLPPGN YKKPKLLYSS NGGHFLRILP DGTVDGTRDR SDQHIQLQLS AESVGEVYIK  60
STETGQYLCM DTDGLLYGSQ TPNEECLFLE RLEENHYNTY ISKKHAEKNW FVGLKKNGSV  120
KRGPRTHYGQ KAILFLPLPV SSD                                         143
```

-continued

```
SEQ ID NO: 95            moltype =    length =
SEQUENCE: 95
000

SEQ ID NO: 96            moltype = AA   length = 142
FEATURE                  Location/Qualifiers
REGION                   1..142
                         note = Description of Artificial Sequence: Synthetic
                          polypeptide
source                   1..142
                         mol_type = protein
                         organism = synthetic construct
SEQUENCE: 96
ALTEKPPGNY KKPKLLYSSN GGHFLRILPD GTVDGTRDRS DQHIQLQLSA ESVGEVYIKS   60
TETGQYLCMD TDGLLYGSQT PNEECLFLER LEENHYNTYI SKKHAEKNWF VGLKKNGSVK  120
RGPRTHYGQK AILFLPLPVS SD                                           142

SEQ ID NO: 97            moltype = AA   length = 141
FEATURE                  Location/Qualifiers
REGION                   1..141
                         note = Description of Artificial Sequence: Synthetic
                          polypeptide
source                   1..141
                         mol_type = protein
                         organism = synthetic construct
SEQUENCE: 97
ALTEKPGNYK KPKLLYSSNG GHFLRILPDG TVDGTRDRSD QHIQLQLSAE SVGEVYIKST   60
ETGQYLCMDT DGLLYGSQTP NEECLFLERL EENHYNTYIS KKHAEKNWFV GLKKNGSVKR  120
GPRTHYGQKA ILFLPLPVSS D                                            141

SEQ ID NO: 98            moltype = AA   length = 144
FEATURE                  Location/Qualifiers
REGION                   1..144
                         note = Description of Artificial Sequence: Synthetic
                          polypeptide
source                   1..144
                         mol_type = protein
                         organism = synthetic construct
SEQUENCE: 98
LTEKFNLPPG NYKKPKLLYS SNGGHFLRIL PDGTVDGTRD RSDQHIQLQL SAESVGEVYI   60
KSTETGQYLC MDTDGLLYGS QTPNEECLFL ERLEENHYNT YISKKHAEKN WFVGLKKNGS  120
VKRGPRTHYG QKAILFLPLP VSSD                                         144

SEQ ID NO: 99            moltype = AA   length = 143
FEATURE                  Location/Qualifiers
REGION                   1..143
                         note = Description of Artificial Sequence: Synthetic
                          polypeptide
source                   1..143
                         mol_type = protein
                         organism = synthetic construct
SEQUENCE: 99
LTEKNLPPGN YKKPKLLYSS NGGHFLRILP DGTVDGTRDR SDQHIQLQLS AESVGEVYIK   60
STETGQYLCM DTDGLLYGSQ TPNEECLFLE RLEENHYNTY ISKKHAEKNW FVGLKKNGSV  120
KRGPRTHYGQ KAILFLPLPV SSD                                          143

SEQ ID NO: 100           moltype = AA   length = 142
FEATURE                  Location/Qualifiers
REGION                   1..142
                         note = Description of Artificial Sequence: Synthetic
                          polypeptide
source                   1..142
                         mol_type = protein
                         organism = synthetic construct
SEQUENCE: 100
LTEKLPGNY KKPKLLYSSN GGHFLRILPD GTVDGTRDRS DQHIQLQLSA ESVGEVYIKS    60
TETGQYLCMD TDGLLYGSQT PNEECLFLER LEENHYNTYI SKKHAEKNWF VGLKKNGSVK  120
RGPRTHYGQK AILFLPLPVS SD                                           142

SEQ ID NO: 101           moltype = AA   length = 141
FEATURE                  Location/Qualifiers
REGION                   1..141
                         note = Description of Artificial Sequence: Synthetic
                          polypeptide
source                   1..141
                         mol_type = protein
                         organism = synthetic construct
SEQUENCE: 101
LTEKPPGNYK KPKLLYSSNG GHFLRILPDG TVDGTRDRSD QHIQLQLSAE SVGEVYIKST   60
```

```
ETGQYLCMDT DGLLYGSQTP NEECLFLERL EENHYNTYIS KKHAEKNWFV GLKKNGSVKR   120
GPRTHYGQKA ILFLPLPVSS D                                              141

SEQ ID NO: 102         moltype = AA  length = 140
FEATURE                Location/Qualifiers
REGION                 1..140
                       note = Description of Artificial Sequence: Synthetic
                        polypeptide
source                 1..140
                       mol_type = protein
                       organism = synthetic construct
SEQUENCE: 102
LTEKPGNYKK PKLLYSSNGG HFLRILPDGT VDGTRDRSDQ HIQLQLSAES VGEVYIKSTE   60
TGQYLCMDTD GLLYGSQTPN EECLFLERLE ENHYNTYISK KHAEKNWFVG LKKNGSVKRG   120
PRTHYGQKAI LFLPLPVSSD                                               140

SEQ ID NO: 103         moltype = AA  length = 143
FEATURE                Location/Qualifiers
REGION                 1..143
                       note = Description of Artificial Sequence: Synthetic
                        polypeptide
source                 1..143
                       mol_type = protein
                       organism = synthetic construct
SEQUENCE: 103
TEKFNLPPGN YKKPKLLYSS NGGHFLRILP DGTVDGTRDR SDQHIQLQLS AESVGEVYIK   60
STETGQYLCM DTDGLLYGSQ TPNEECLFLE RLEENHYNTY ISKKHAEKNW FVGLKKNGSV   120
KRGPRTHYGQ KAILFLPLPV SSD                                           143

SEQ ID NO: 104         moltype = AA  length = 142
FEATURE                Location/Qualifiers
REGION                 1..142
                       note = Description of Artificial Sequence: Synthetic
                        polypeptide
source                 1..142
                       mol_type = protein
                       organism = synthetic construct
SEQUENCE: 104
TEKNLPPGNY KKPKLLYSSN GGHFLRILPD GTVDGTRDRS DQHIQLQLSA ESVGEVYIKS   60
TETGQYLCMD TDGLLYGSQT PNEECLFLER LEENHYNTYI SKKHAEKNWF VGLKKNGSVK   120
RGPRTHYGQK AILFLPLPVS SD                                            142

SEQ ID NO: 105         moltype = AA  length = 141
FEATURE                Location/Qualifiers
REGION                 1..141
                       note = Description of Artificial Sequence: Synthetic
                        polypeptide
source                 1..141
                       mol_type = protein
                       organism = synthetic construct
SEQUENCE: 105
TEKLPPGNYK KPKLLYSSNG GHFLRILPDG TVDGTRDRSD QHIQLQLSAE SVGEVYIKST   60
ETGQYLCMDT DGLLYGSQTP NEECLFLERL EENHYNTYIS KKHAEKNWFV GLKKNGSVKR   120
GPRTHYGQKA ILFLPLPVSS D                                             141

SEQ ID NO: 106         moltype = AA  length = 140
FEATURE                Location/Qualifiers
REGION                 1..140
                       note = Description of Artificial Sequence: Synthetic
                        polypeptide
source                 1..140
                       mol_type = protein
                       organism = synthetic construct
SEQUENCE: 106
TEKPPGNYKK PKLLYSSNGG HFLRILPDGT VDGTRDRSDQ HIQLQLSAES VGEVYIKSTE   60
TGQYLCMDTD GLLYGSQTPN EECLFLERLE ENHYNTYISK KHAEKNWFVG LKKNGSVKRG   120
PRTHYGQKAI LFLPLPVSSD                                               140

SEQ ID NO: 107         moltype = AA  length = 139
FEATURE                Location/Qualifiers
REGION                 1..139
                       note = Description of Artificial Sequence: Synthetic
                        polypeptide
source                 1..139
                       mol_type = protein
                       organism = synthetic construct
SEQUENCE: 107
TEKPGNYKKP KLLYSSNGGH FLRILPDGTV DGTRDRSDQH IQLQLSAESV GEVYIKSTET   60
GQYLCMDTDG LLYGSQTPNE ECLFLERLEE NHYNTYISKK HAEKNWFVGL KKNGSVKRGP   120
```

```
RTHYGQKAIL FLPLPVSSD                                             139

SEQ ID NO: 108        moltype = AA  length = 142
FEATURE               Location/Qualifiers
REGION                1..142
                      note = Description of Artificial Sequence: Synthetic
                       polypeptide
source                1..142
                      mol_type = protein
                      organism = synthetic construct
SEQUENCE: 108
EKFNLPPGNY KKPKLLYSSN GGHFLRILPD GTVDGTRDRS DQHIQLQLSA ESVGEVYIKS  60
TETGQYLCMD TDGLLYGSQT PNEECLFLER LEENHYNTYI SKKHAEKNWF VGLKKNGSVK  120
RGPRTHYGQK AILFLPLPVS SD                                          142

SEQ ID NO: 109        moltype = AA  length = 141
FEATURE               Location/Qualifiers
REGION                1..141
                      note = Description of Artificial Sequence: Synthetic
                       polypeptide
source                1..141
                      mol_type = protein
                      organism = synthetic construct
SEQUENCE: 109
EKNLPPGNYK KPKLLYSSNG GHFLRILPDG TVDGTRDRSD QHIQLQLSAE SVGEVYIKST  60
ETGQYLCMDT DGLLYGSQTP NEECLFLERL EENHYNTYIS KKHAEKNWFV GLKKNGSVKR  120
GPRTHYGQKA ILFLPLPVSS D                                           141

SEQ ID NO: 110        moltype = AA  length = 140
FEATURE               Location/Qualifiers
REGION                1..140
                      note = Description of Artificial Sequence: Synthetic
                       polypeptide
source                1..140
                      mol_type = protein
                      organism = synthetic construct
SEQUENCE: 110
EKLPPGNYKK PKLLYSSNGG HFLRILPDGT VDGTRDRSDQ HIQLQLSAES VGEVYIKSTE  60
TGQYLCMDTD GLLYGSQTPN EECLFLERLE ENHYNTYISK KHAEKNWFVG LKKNGSVKRG  120
PRTHYGQKAI LFLPLPVSSD                                             140

SEQ ID NO: 111        moltype = AA  length = 139
FEATURE               Location/Qualifiers
REGION                1..139
                      note = Description of Artificial Sequence: Synthetic
                       polypeptide
source                1..139
                      mol_type = protein
                      organism = synthetic construct
SEQUENCE: 111
EKPPGNYKKP KLLYSSNGGH FLRILPDGTV DGTRDRSDQH IQLQLSAESV GEVYIKSTET  60
GQYLCMDTDG LLYGSQTPNE ECLFLERLEE NHYNTYISKK HAEKNWFVGL KKNGSVKRGP  120
RTHYGQKAIL FLPLPVSSD                                             139

SEQ ID NO: 112        moltype = AA  length = 138
FEATURE               Location/Qualifiers
REGION                1..138
                      note = Description of Artificial Sequence: Synthetic
                       polypeptide
source                1..138
                      mol_type = protein
                      organism = synthetic construct
SEQUENCE: 112
EKPGNYKKPK LLYSSNGGHF LRILPDGTVD GTRDRSDQHI QLQLSAESVG EVYIKSTETG  60
QYLCMDTDGL LYGSQTPNEE CLFLERLEEN HYNTYISKKH AEKNWFVGLK KNGSVKRGPR  120
THYGQKAILF LPLPVSSD                                              138

SEQ ID NO: 113        moltype = AA  length = 141
FEATURE               Location/Qualifiers
REGION                1..141
                      note = Description of Artificial Sequence: Synthetic
                       polypeptide
source                1..141
                      mol_type = protein
                      organism = synthetic construct
SEQUENCE: 113
KFNLPPGNYK KPKLLYSSNG GHFLRILPDG TVDGTRDRSD QHIQLQLSAE SVGEVYIKST  60
ETGQYLCMDT DGLLYGSQTP NEECLFLERL EENHYNTYIS KKHAEKNWFV GLKKNGSVKR  120
GPRTHYGQKA ILFLPLPVSS D                                           141
```

```
SEQ ID NO: 114            moltype = AA  length = 140
FEATURE                  Location/Qualifiers
REGION                   1..140
                         note = Description of Artificial Sequence: Synthetic
                          polypeptide
source                   1..140
                         mol_type = protein
                         organism = synthetic construct
SEQUENCE: 114
KNLPPGNYKK PKLLYSSNGG HFLRILPDGT VDGTRDRSDQ HIQLQLSAES VGEVYIKSTE  60
TGQYLCMDTD GLLYGSQTPN EECLFLERLE ENHYNTYISK KHAEKNWFVG LKKNGSVKRG  120
PRTHYGQKAI LFLPLPVSSD                                              140

SEQ ID NO: 115            moltype = AA  length = 139
FEATURE                  Location/Qualifiers
REGION                   1..139
                         note = Description of Artificial Sequence: Synthetic
                          polypeptide
source                   1..139
                         mol_type = protein
                         organism = synthetic construct
SEQUENCE: 115
KLPPGNYKKP KLLYSSNGGH FLRILPDGTV DGTRDRSDQH IQLQLSAESV GEVYIKSTET  60
GQYLCMDTDG LLYGSQTPNE ECLFLERLEE NHYNTYISKK HAEKNWFVGL KKNGSVKRGP  120
RTHYGQKAIL FLPLPVSSD                                               139

SEQ ID NO: 116            moltype = AA  length = 138
FEATURE                  Location/Qualifiers
REGION                   1..138
                         note = Description of Artificial Sequence: Synthetic
                          polypeptide
source                   1..138
                         mol_type = protein
                         organism = synthetic construct
SEQUENCE: 116
KPPGNYKKPK LLYSSNGGHF LRILPDGTVD GTRDRSDQHI QLQLSAESVG EVYIKSTETG  60
QYLCMDTDGL LYGSQTPNEE CLFLERLEEN HYNTYISKKH AEKNWFVGLK KNGSVKRGPR  120
THYGQKAILF LPLPVSSD                                                138

SEQ ID NO: 117            moltype = AA  length = 137
FEATURE                  Location/Qualifiers
REGION                   1..137
                         note = Description of Artificial Sequence: Synthetic
                          polypeptide
source                   1..137
                         mol_type = protein
                         organism = synthetic construct
SEQUENCE: 117
KPGNYKKPKL LYSSNGGHFL RILPDGTVDG TRDRSDQHIQ LQLSAESVGE VYIKSTETGQ  60
YLCMDTDGLL YGSQTPNEEC LFLERLEENH YNTYISKKHA EKNWFVGLKK NGSVKRGPRT  120
HYGQKAILFL PLPVSSD                                                 137

SEQ ID NO: 118            moltype = AA  length = 146
FEATURE                  Location/Qualifiers
REGION                   1..146
                         note = Description of Artificial Sequence: Synthetic
                          polypeptide
source                   1..146
                         mol_type = protein
                         organism = synthetic construct
SEQUENCE: 118
MALTEKFNLP PGNYKKPKLL YSSNGGHFLR ILPDGTVDGT RDRSDQHIQL QLSAESVGEV  60
YIKSTETGQY LCMDTDGLLY GSQTPNEECL FLERLEENHY NTYISKKHAE KNWFVGLKKN  120
GSVKRGPRTH YGQKAILFLP LPVSSD                                       146

SEQ ID NO: 119            moltype = AA  length = 144
FEATURE                  Location/Qualifiers
REGION                   1..144
                         note = Description of Artificial Sequence: Synthetic
                          polypeptide
source                   1..144
                         mol_type = protein
                         organism = synthetic construct
SEQUENCE: 119
MALTEKLPPG NYKKPKLLYS SNGGHFLRIL PDGTVDGTRD RSDQHIQLQL SAESVGEVYI  60
KSTETGQYLC MDTDGLLYGS QTPNEECLFL ERLEENHYNT YISKKHAEKN WFVGLKKNGS  120
VKRGPRTHYG QKAILFLPLP VSSD                                         144
```

-continued

```
SEQ ID NO: 120          moltype = AA   length = 143
FEATURE                 Location/Qualifiers
REGION                  1..143
                        note = Description of Artificial Sequence: Synthetic
                         polypeptide
source                  1..143
                        mol_type = protein
                        organism = synthetic construct
SEQUENCE: 120
MALTEKPPGN YKKPKLLYSS NGGHFLRILP DGTVDGTRDR SDQHIQLQLS AESVGEVYIK  60
STETGQYLCM DTDGLLYGSQ TPNEECLFLE RLEENHYNTY ISKKHAEKNW FVGLKKNGSV  120
KRGPRTHYGQ KAILFLPLPV SSD                                          143

SEQ ID NO: 121          moltype = AA   length = 142
FEATURE                 Location/Qualifiers
REGION                  1..142
                        note = Description of Artificial Sequence: Synthetic
                         polypeptide
source                  1..142
                        mol_type = protein
                        organism = synthetic construct
SEQUENCE: 121
MALTEKPGNY KKPKLLYSSN GGHFLRILPD GTVDGTRDRS DQHIQLQLSA ESVGEVYIKS  60
TETGQYLCMD TDGLLYGSQT PNEECLFLER LEENHYNTYI SKKHAEKNWF VGLKKNGSVK  120
RGPRTHYGQK AILFLPLPVS SD                                           142

SEQ ID NO: 122          moltype = AA   length = 145
FEATURE                 Location/Qualifiers
REGION                  1..145
                        note = Description of Artificial Sequence: Synthetic
                         polypeptide
source                  1..145
                        mol_type = protein
                        organism = synthetic construct
SEQUENCE: 122
MLTEKFNLPP GNYKKPKLLY SSNGGHFLRI LPDGTVDGTR DRSDQHIQLQ LSAESVGEVY  60
IKSTETGQYL CMDTDGLLYG SQTPNEECLF LERLEENHYN TYISKKHAEK NWFVGLKKNG  120
SVKRGPRTHY GQKAILFLPL PVSSD                                        145

SEQ ID NO: 123          moltype = AA   length = 144
FEATURE                 Location/Qualifiers
REGION                  1..144
                        note = Description of Artificial Sequence: Synthetic
                         polypeptide
source                  1..144
                        mol_type = protein
                        organism = synthetic construct
SEQUENCE: 123
MLTEKNLPPG NYKKPKLLYS SNGGHFLRIL PDGTVDGTRD RSDQHIQLQL SAESVGEVYI  60
KSTETGQYLC MDTDGLLYGS QTPNEECLFL ERLEENHYNT YISKKHAEKN WFVGLKKNGS  120
VKRGPRTHYG QKAILFLPLP VSSD                                         144

SEQ ID NO: 124          moltype = AA   length = 143
FEATURE                 Location/Qualifiers
REGION                  1..143
                        note = Description of Artificial Sequence: Synthetic
                         polypeptide
source                  1..143
                        mol_type = protein
                        organism = synthetic construct
SEQUENCE: 124
MLTEKLPPGN YKKPKLLYSS NGGHFLRILP DGTVDGTRDR SDQHIQLQLS AESVGEVYIK  60
STETGQYLCM DTDGLLYGSQ TPNEECLFLE RLEENHYNTY ISKKHAEKNW FVGLKKNGSV  120
KRGPRTHYGQ KAILFLPLPV SSD                                          143

SEQ ID NO: 125          moltype = AA   length = 142
FEATURE                 Location/Qualifiers
REGION                  1..142
                        note = Description of Artificial Sequence: Synthetic
                         polypeptide
source                  1..142
                        mol_type = protein
                        organism = synthetic construct
SEQUENCE: 125
MLTEKPPGNY KKPKLLYSSN GGHFLRILPD GTVDGTRDRS DQHIQLQLSA ESVGEVYIKS  60
TETGQYLCMD TDGLLYGSQT PNEECLFLER LEENHYNTYI SKKHAEKNWF VGLKKNGSVK  120
RGPRTHYGQK AILFLPLPVS SD                                           142

SEQ ID NO: 126          moltype = AA   length = 141
```

```
FEATURE                 Location/Qualifiers
REGION                  1..141
                        note = Description of Artificial Sequence: Synthetic
                         polypeptide
source                  1..141
                        mol_type = protein
                        organism = synthetic construct
SEQUENCE: 126
MLTEKPGNYK KPKLLYSSNG GHFLRILPDG TVDGTRDRSD QHIQLQLSAE SVGEVYIKST  60
ETGQYLCMDT DGLLYGSQTP NEECLFLERL EENHYNTYIS KKHAEKNWFV GLKKNGSVKR  120
GPRTHYGQKA ILFLPLPVSS D                                            141

SEQ ID NO: 127          moltype = AA  length = 144
FEATURE                 Location/Qualifiers
REGION                  1..144
                        note = Description of Artificial Sequence: Synthetic
                         polypeptide
source                  1..144
                        mol_type = protein
                        organism = synthetic construct
SEQUENCE: 127
MTEKFNLPPG NYKKPKLLYS SNGGHFLRIL PDGTVDGTRD RSDQHIQLQL SAESVGEVYI  60
KSTETGQYLC MDTDGLLYGS QTPNEECLFL ERLEENHYNT YISKKHAEKN WFVGLKKNGS  120
VKRGPRTHYG QKAILFLPLP VSSD                                         144

SEQ ID NO: 128          moltype = AA  length = 143
FEATURE                 Location/Qualifiers
REGION                  1..143
                        note = Description of Artificial Sequence: Synthetic
                         polypeptide
source                  1..143
                        mol_type = protein
                        organism = synthetic construct
SEQUENCE: 128
MTEKNLPPGN YKKPKLLYSS NGGHFLRILP DGTVDGTRDR SDQHIQLQLS AESVGEVYIK  60
STETGQYLCM DTDGLLYGSQ TPNEECLFLE RLEENHYNTY ISKKHAEKNW FVGLKKNGSV  120
KRGPRTHYGQ KAILFLPLPV SSD                                          143

SEQ ID NO: 129          moltype = AA  length = 142
FEATURE                 Location/Qualifiers
REGION                  1..142
                        note = Description of Artificial Sequence: Synthetic
                         polypeptide
source                  1..142
                        mol_type = protein
                        organism = synthetic construct
SEQUENCE: 129
MTEKLPPGNY KKPKLLYSSN GGHFLRILPD GTVDGTRDRS DQHIQLQLSA ESVGEVYIKS  60
TETGQYLCMD TDGLLYGSQT PNEECLFLER LEENHYNTYI SKKHAEKNWF VGLKKNGSVK  120
RGPRTHYGQK AILFLPLPVS SD                                           142

SEQ ID NO: 130          moltype = AA  length = 141
FEATURE                 Location/Qualifiers
REGION                  1..141
                        note = Description of Artificial Sequence: Synthetic
                         polypeptide
source                  1..141
                        mol_type = protein
                        organism = synthetic construct
SEQUENCE: 130
MTEKPPGNYK KPKLLYSSNG GHFLRILPDG TVDGTRDRSD QHIQLQLSAE SVGEVYIKST  60
ETGQYLCMDT DGLLYGSQTP NEECLFLERL EENHYNTYIS KKHAEKNWFV GLKKNGSVKR  120
GPRTHYGQKA ILFLPLPVSS D                                            141

SEQ ID NO: 131          moltype = AA  length = 140
FEATURE                 Location/Qualifiers
REGION                  1..140
                        note = Description of Artificial Sequence: Synthetic
                         polypeptide
source                  1..140
                        mol_type = protein
                        organism = synthetic construct
SEQUENCE: 131
MTEKPGNYKK PKLLYSSNGG HFLRILPDGT VDGTRDRSDQ HIQLQLSAES VGEVYIKSTE  60
TGQYLCMDTD GLLYGSQTPN EECLFLERLE ENHYNTYISK KHAEKNWFVG LKKNGSVKRG  120
PRTHYGQKAI LFLPLPVSSD                                              140

SEQ ID NO: 132          moltype = AA  length = 143
FEATURE                 Location/Qualifiers
```

-continued

```
REGION                    1..143
                          note = Description of Artificial Sequence: Synthetic
                           polypeptide
source                    1..143
                          mol_type = protein
                          organism = synthetic construct
SEQUENCE: 132
MEKFNLPPGN YKKPKLLYSS NGGHFLRILP DGTVDGTRDR SDQHIQLQLS AESVGEVYIK  60
STETGQYLCM DTDGLLYGSQ TPNEECLFLE RLEENHYNTY ISKKHAEKNW FVGLKKNGSV  120
KRGPRTHYGQ KAILFLPLPV SSD                                          143

SEQ ID NO: 133            moltype = AA  length = 142
FEATURE                   Location/Qualifiers
REGION                    1..142
                          note = Description of Artificial Sequence: Synthetic
                           polypeptide
source                    1..142
                          mol_type = protein
                          organism = synthetic construct
SEQUENCE: 133
MEKNLPPGNY KKPKLLYSSN GGHFLRILPD GTVDGTRDRS DQHIQLQLSA ESVGEVYIKS  60
TETGQYLCMD TDGLLYGSQT PNEECLFLER LEENHYNTYI SKKHAEKNWF VGLKKNGSVK  120
RGPRTHYGQK AILFLPLPVS SD                                           142

SEQ ID NO: 134            moltype = AA  length = 141
FEATURE                   Location/Qualifiers
REGION                    1..141
                          note = Description of Artificial Sequence: Synthetic
                           polypeptide
source                    1..141
                          mol_type = protein
                          organism = synthetic construct
SEQUENCE: 134
MEKLPPGNYK KPKLLYSSNG GHFLRILPDG TVDGTRDRSD QHIQLQLSAE SVGEVYIKST  60
ETGQYLCMDT DGLLYGSQTP NEECLFLERL EENHYNTYIS KKHAEKNWFV GLKKNGSVKR  120
GPRTHYGQKA ILFLPLPVSS D                                            141

SEQ ID NO: 135            moltype = AA  length = 140
FEATURE                   Location/Qualifiers
REGION                    1..140
                          note = Description of Artificial Sequence: Synthetic
                           polypeptide
source                    1..140
                          mol_type = protein
                          organism = synthetic construct
SEQUENCE: 135
MEKPPGNYKK PKLLYSSNGG HFLRILPDGT VDGTRDRSDQ HIQLQLSAES VGEVYIKSTE  60
TGQYLCMDTD GLLYGSQTPN EECLFLERLE ENHYNTYISK KHAEKNWFVG LKKNGSVKRG  120
PRTHYGQKAI LFLPLPVSSD                                              140

SEQ ID NO: 136            moltype = AA  length = 139
FEATURE                   Location/Qualifiers
REGION                    1..139
                          note = Description of Artificial Sequence: Synthetic
                           polypeptide
source                    1..139
                          mol_type = protein
                          organism = synthetic construct
SEQUENCE: 136
MEKPGNYKKP KLLYSSNGGH FLRILPDGTV DGTRDRSDQH IQLQLSAESV GEVYIKSTET  60
GQYLCMDTDG LLYGSQTPNE ECLFLERLEE NHYNTYISKK HAEKNWFVGL KKNGSVKRGP  120
RTHYGQKAIL FLPLPVSSD                                               139

SEQ ID NO: 137            moltype = AA  length = 142
FEATURE                   Location/Qualifiers
REGION                    1..142
                          note = Description of Artificial Sequence: Synthetic
                           polypeptide
source                    1..142
                          mol_type = protein
                          organism = synthetic construct
SEQUENCE: 137
MKFNLPPGNY KKPKLLYSSN GGHFLRILPD GTVDGTRDRS DQHIQLQLSA ESVGEVYIKS  60
TETGQYLCMD TDGLLYGSQT PNEECLFLER LEENHYNTYI SKKHAEKNWF VGLKKNGSVK  120
RGPRTHYGQK AILFLPLPVS SD                                           142

SEQ ID NO: 138            moltype = AA  length = 141
FEATURE                   Location/Qualifiers
REGION                    1..141
```

```
                               note = Description of Artificial Sequence: Synthetic
                                polypeptide
source                         1..141
                               mol_type = protein
                               organism = synthetic construct
SEQUENCE: 138
MKNLPPGNYK KPKLLYSSNG GHFLRILPDG TVDGTRDRSD QHIQLQLSAE SVGEVYIKST   60
ETGQYLCMDT DGLLYGSQTP NEECLFLERL EENHYNTYIS KKHAEKNWFV GLKKNGSVKR  120
GPRTHYGQKA ILFLPLPVSS D                                            141

SEQ ID NO: 139          moltype = AA   length = 140
FEATURE                 Location/Qualifiers
REGION                  1..140
                        note = Description of Artificial Sequence: Synthetic
                         polypeptide
source                  1..140
                        mol_type = protein
                        organism = synthetic construct
SEQUENCE: 139
MKLPPGNYKK PKLLYSSNGG HFLRILPDGT VDGTRDRSDQ HIQLQLSAES VGEVYIKSTE   60
TGQYLCMDTD GLLYGSQTPN EECLFLERLE ENHYNTYISK KHAEKNWFVG LKKNGSVKRG  120
PRTHYGQKAI LFLPLPVSSD                                              140

SEQ ID NO: 140          moltype = AA   length = 139
FEATURE                 Location/Qualifiers
REGION                  1..139
                        note = Description of Artificial Sequence: Synthetic
                         polypeptide
source                  1..139
                        mol_type = protein
                        organism = synthetic construct
SEQUENCE: 140
MKPPGNYKKP KLLYSSNGGH FLRILPDGTV DGTRDRSDQH IQLQLSAESV GEVYIKSTET   60
GQYLCMDTDG LLYGSQTPNE ECLFLERLEE NHYNTYISKK HAEKNWFVGL KKNGSVKRGP  120
RTHYGQKAIL FLPLPVSSD                                               139

SEQ ID NO: 141          moltype = AA   length = 138
FEATURE                 Location/Qualifiers
REGION                  1..138
                        note = Description of Artificial Sequence: Synthetic
                         polypeptide
source                  1..138
                        mol_type = protein
                        organism = synthetic construct
SEQUENCE: 141
MKPGNYKKPK LLYSSNGGHF LRILPDGTVD GTRDRSDQHI QLQLSAESVG EVYIKSTETG   60
QYLCMDTDGL LYGSQTPNEE CLFLERLEEN HYNTYISKKH AEKNWFVGLK KNGSVKRGPR  120
THYGQKAILF LPLPVSSD                                                138

SEQ ID NO: 142          moltype = AA   length = 140
FEATURE                 Location/Qualifiers
REGION                  1..140
                        note = Description of Artificial Sequence: Synthetic
                         polypeptide
MOD_RES                 67
                        note = Any amino acid
source                  1..140
                        mol_type = protein
                        organism = synthetic construct
SEQUENCE: 142
FNLPPGNYKK PKLLYCSNGG HFLRILPDGT VDGTRDRSDQ HIQLQLSAES VGEVYIKSTE   60
TGQYLAXDTD GLLYGSQTPN EECLFLERLE ENHYNTYISK KHAEKNWFVG LKKNGSCKRG  120
PRTHYGQKAI LFLPLPVSSD                                              140

SEQ ID NO: 143          moltype = AA   length = 139
FEATURE                 Location/Qualifiers
REGION                  1..139
                        note = Description of Artificial Sequence: Synthetic
                         polypeptide
MOD_RES                 66
                        note = Any amino acid
source                  1..139
                        mol_type = protein
                        organism = synthetic construct
SEQUENCE: 143
NLPPGNYKKP KLLYCSNGGH FLRILPDGTV DGTRDRSDQH IQLQLSAESV GEVYIKSTET   60
GQYLAXDTDG LLYGSQTPNE ECLFLERLEE NHYNTYISKK HAEKNWFVGL KKNGSCKRGP  120
RTHYGQKAIL FLPLPVSSD                                               139
```

-continued

```
SEQ ID NO: 144           moltype = AA   length = 137
FEATURE                  Location/Qualifiers
REGION                   1..137
                         note = Description of Artificial Sequence: Synthetic
                          polypeptide
MOD_RES                  64
                         note = Any amino acid
source                   1..137
                         mol_type = protein
                         organism = synthetic construct
SEQUENCE: 144
PPGNYKKPKL LYCSNGGHFL RILPDGTVDG TRDRSDQHIQ LQLSAESVGE VYIKSTETGQ  60
YLAXDTDGLL YGSQTPNEEC LFLERLEENH YNTYISKKHA EKNWFVGLKK NGSCKRGPRT  120
HYGQKAILFL PLPVSSD                                                137

SEQ ID NO: 145           moltype = AA   length = 136
FEATURE                  Location/Qualifiers
REGION                   1..136
                         note = Description of Artificial Sequence: Synthetic
                          polypeptide
MOD_RES                  63
                         note = Any amino acid
source                   1..136
                         mol_type = protein
                         organism = synthetic construct
SEQUENCE: 145
PGNYKKPKLL YCSNGGHFLR ILPDGTVDGT RDRSDQHIQL QLSAESVGEV YIKSTETGQY  60
LAXDTDGLLY GSQTPNEECL FLERLEENHY NTYISKKHAE KNWFVGLKKN GSCKRGPRTH  120
YGQKAILFLP LPVSSD                                                 136

SEQ ID NO: 146           moltype = AA   length = 140
FEATURE                  Location/Qualifiers
REGION                   1..140
                         note = Description of Artificial Sequence: Synthetic
                          polypeptide
MOD_RES                  67
                         note = Any amino acid
source                   1..140
                         mol_type = protein
                         organism = synthetic construct
SEQUENCE: 146
FNLPPGNYKK PKLLYSSNGG HFLRILPDGT VDGTRDRSDQ HIQLQLSAES VGEVYIKSTE  60
TGQYLCXDTD GLLYGSQTPN EECLFLERLE ENHYNTYISK KHAEKNWFVG LKKNGSVKRG  120
PRTHYGQKAI LFLPLPVSSD                                             140

SEQ ID NO: 147           moltype = AA   length = 139
FEATURE                  Location/Qualifiers
REGION                   1..139
                         note = Description of Artificial Sequence: Synthetic
                          polypeptide
MOD_RES                  66
                         note = Any amino acid
source                   1..139
                         mol_type = protein
                         organism = synthetic construct
SEQUENCE: 147
NLPPGNYKKP KLLYSSNGGH FLRILPDGTV DGTRDRSDQH IQLQLSAESV GEVYIKSTET  60
GQYLCXDTDG LLYGSQTPNE ECLFLERLEE NHYNTYISKK HAEKNWFVGL KKNGSVKRGP  120
RTHYGQKAIL FLPLPVSSD                                              139

SEQ ID NO: 148           moltype = AA   length = 137
FEATURE                  Location/Qualifiers
REGION                   1..137
                         note = Description of Artificial Sequence: Synthetic
                          polypeptide
MOD_RES                  64
                         note = Any amino acid
source                   1..137
                         mol_type = protein
                         organism = synthetic construct
SEQUENCE: 148
PPGNYKKPKL LYSSNGGHFL RILPDGTVDG TRDRSDQHIQ LQLSAESVGE VYIKSTETGQ  60
YLCXDTDGLL YGSQTPNEEC LFLERLEENH YNTYISKKHA EKNWFVGLKK NGSVKRGPRT  120
HYGQKAILFL PLPVSSD                                                137

SEQ ID NO: 149           moltype = AA   length = 136
FEATURE                  Location/Qualifiers
REGION                   1..136
                         note = Description of Artificial Sequence: Synthetic
```

```
                            polypeptide
MOD_RES                     63
                            note = Any amino acid
source                      1..136
                            mol_type = protein
                            organism = synthetic construct
SEQUENCE: 149
PGNYKKPKLL YSSNGGHFLR ILPDGTVDGT RDRSDQHIQL QLSAESVGEV YIKSTETGQY  60
LCXDTDGLLY GSQTPNEECL FLERLEENHY NTYISKKHAE KNWFVGLKKN GSVKRGPRTH  120
YGQKAILFLP LPVSSD                                                  136

SEQ ID NO: 150              moltype = AA  length = 144
FEATURE                     Location/Qualifiers
REGION                      1..144
                            note = Description of Artificial Sequence: Synthetic
                             polypeptide
MOD_RES                     71
                            note = Any amino acid
source                      1..144
                            mol_type = protein
                            organism = synthetic construct
SEQUENCE: 150
ALTEKNLPPG NYKKPKLLYC SNGGHFLRIL PDGTVDGTRD RSDQHIQLQL SAESVGEVYI  60
KSTETGQYLA XDTDGLLYGS QTPNEECLFL ERLEENHYNT YISKKHAEKN WFVGLKKNGS  120
CKRGPRTHYG QKAILFLPLP VSSD                                         144

SEQ ID NO: 151              moltype = AA  length = 143
FEATURE                     Location/Qualifiers
REGION                      1..143
                            note = Description of Artificial Sequence: Synthetic
                             polypeptide
MOD_RES                     70
                            note = Any amino acid
source                      1..143
                            mol_type = protein
                            organism = synthetic construct
SEQUENCE: 151
ALTEKLPPGN YKKPKLLYSS NGGHFLRILP DGTVDGTRDR SDQHIQLQLS AESVGEVYIK  60
STETGQYLCX DTDGLLYGSQ TPNEECLFLE RLEENHYNTY ISKKHAEKNW FVGLKKNGSV  120
KRGPRTHYGQ KAILFLPLPV SSD                                          143

SEQ ID NO: 152              moltype = AA  length = 143
FEATURE                     Location/Qualifiers
REGION                      1..143
                            note = Description of Artificial Sequence: Synthetic
                             polypeptide
MOD_RES                     70
                            note = Any amino acid
source                      1..143
                            mol_type = protein
                            organism = synthetic construct
SEQUENCE: 152
ALTEKPPGGN YKKPKLLYCS NGGHFLRILP DGTVDGTRDR SDQHIQLQLS AESVGEVYIK  60
STETGQYLAX DTDGLLYGSQ TPNEECLFLE RLEENHYNTY ISKKHAEKNW FVGLKKNGSC  120
KRGPRTHYGQ KAILFLPLPV SSD                                          143

SEQ ID NO: 153              moltype = AA  length = 141
FEATURE                     Location/Qualifiers
REGION                      1..141
                            note = Description of Artificial Sequence: Synthetic
                             polypeptide
MOD_RES                     68
                            note = Any amino acid
source                      1..141
                            mol_type = protein
                            organism = synthetic construct
SEQUENCE: 153
ALTEKPGNYK KPKLLYCSNG GHFLRILPDG TVDGTRDRSD QHIQLQLSAE SVGEVYIKST  60
ETGQYLAXDT DGLLYGSQTP NEECLFLERL EENHYNTYIS KKHAEKNWFV GLKKNGSCKR  120
GPRTHYGQKA ILFLPLPVSS D                                            141

SEQ ID NO: 154              moltype = AA  length = 144
FEATURE                     Location/Qualifiers
REGION                      1..144
                            note = Description of Artificial Sequence: Synthetic
                             polypeptide
MOD_RES                     71
                            note = Any amino acid
source                      1..144
```

-continued

```
                           mol_type = protein
                           organism = synthetic construct
SEQUENCE: 154
LTEKFNLPPG NYKKPKLLYC SNGGHFLRIL PDGTVDGTRD RSDQHIQLQL SAESVGEVYI  60
KSTETGQYLA XDTDGLLYGS QTPNEECLFL ERLEENHYNT YISKKHAEKN WFVGLKKNGS  120
CKRGPRTHYG QKAILFLPLP VSSD                                         144

SEQ ID NO: 155           moltype = AA   length = 143
FEATURE                  Location/Qualifiers
REGION                   1..143
                         note = Description of Artificial Sequence: Synthetic
                          polypeptide
MOD_RES                  70
                         note = Any amino acid
source                   1..143
                         mol_type = protein
                         organism = synthetic construct
SEQUENCE: 155
LTEKNLPPGN YKKPKLLYCS NGGHFLRILP DGTVDGTRDR SDQHIQLQLS AESVGEVYIK  60
STETGQYLAX DTDGLLYGSQ TPNEECLFLE RLEENHYNTY ISKKHAEKNW FVGLKKNGSC  120
KRGPRTHYGQ KAILFLPLPV SSD                                          143

SEQ ID NO: 156           moltype = AA   length = 142
FEATURE                  Location/Qualifiers
REGION                   1..142
                         note = Description of Artificial Sequence: Synthetic
                          polypeptide
MOD_RES                  69
                         note = Any amino acid
source                   1..142
                         mol_type = protein
                         organism = synthetic construct
SEQUENCE: 156
LTEKLPPGNY KKPKLLYCSN GGHFLRILPD GTVDGTRDRS DQHIQLQLSA ESVGEVYIKS  60
TETGQYLAXD TDGLLYGSQT PNEECLFLER LEENHYNTYI SKKHAEKNWF VGLKKNGSCK  120
RGPRTHYGQK AILFLPLPVS SD                                           142

SEQ ID NO: 157           moltype = AA   length = 141
FEATURE                  Location/Qualifiers
REGION                   1..141
                         note = Description of Artificial Sequence: Synthetic
                          polypeptide
MOD_RES                  68
                         note = Any amino acid
source                   1..141
                         mol_type = protein
                         organism = synthetic construct
SEQUENCE: 157
LTEKPPGNYK KPKLLYCSNG GHFLRILPDG TVDGTRDRSD QHIQLQLSAE SVGEVYIKST  60
ETGQYLAXDT DGLLYGSQTP NEECLFLERL EENHYNTYIS KKHAEKNWFV GLKKNGSCKR  120
GPRTHYGQKA ILFLPLPVSS D                                            141

SEQ ID NO: 158           moltype = AA   length = 140
FEATURE                  Location/Qualifiers
REGION                   1..140
                         note = Description of Artificial Sequence: Synthetic
                          polypeptide
MOD_RES                  67
                         note = Any amino acid
source                   1..140
                         mol_type = protein
                         organism = synthetic construct
SEQUENCE: 158
LTEKPGNYKK PKLLYCSNGG HFLRILPDGT VDGTRDRSDQ HIQLQLSAES VGEVYIKSTE  60
TGQYLAXDTD GLLYGSQTPN EECLFLERLE ENHYNTYISK KHAEKNWFVG LKKNGSCKRG  120
PRTHYGQKAI LFLPLPVSSD                                              140

SEQ ID NO: 159           moltype = AA   length = 143
FEATURE                  Location/Qualifiers
REGION                   1..143
                         note = Description of Artificial Sequence: Synthetic
                          polypeptide
MOD_RES                  70
                         note = Any amino acid
source                   1..143
                         mol_type = protein
                         organism = synthetic construct
SEQUENCE: 159
TEKFNLPPGN YKKPKLLYCS NGGHFLRILP DGTVDGTRDR SDQHIQLQLS AESVGEVYIK  60
```

```
STETGQYLAX DTDGLLYGSQ TPNEECLFLE RLEENHYNTY ISKKHAEKNW FVGLKKNGSC  120
KRGPRTHYGQ KAILFLPLPV SSD                                            143

SEQ ID NO: 160            moltype = AA  length = 142
FEATURE                   Location/Qualifiers
REGION                    1..142
                          note = Description of Artificial Sequence: Synthetic
                           polypeptide
MOD_RES                   69
                          note = Any amino acid
source                    1..142
                          mol_type = protein
                          organism = synthetic construct
SEQUENCE: 160
TEKNLPPGNY KKPKLLYCSN GGHFLRILPD GTVDGTRDRS DQHIQLQLSA ESVGEVYIKS  60
TETGQYLAXD TDGLLYGSQT PNEECLFLER LEENHYNTYI SKKHAEKNWF VGLKKNGSCK  120
RGPRTHYGQK AILFLPLPVS SD                                            142

SEQ ID NO: 161            moltype = AA  length = 141
FEATURE                   Location/Qualifiers
REGION                    1..141
                          note = Description of Artificial Sequence: Synthetic
                           polypeptide
MOD_RES                   68
                          note = Any amino acid
source                    1..141
                          mol_type = protein
                          organism = synthetic construct
SEQUENCE: 161
TEKLPPGNYK KPKLLYCSNG GHFLRILPDG TVDGTRDRSD QHIQLQLSAE SVGEVYIKST  60
ETGQYLAXDT DGLLYGSQTP NEECLFLERL EENHYNTYIS KKHAEKNWFV GLKKNGSCKR  120
GPRTHYGQKA ILFLPLPVSS D                                             141

SEQ ID NO: 162            moltype = AA  length = 140
FEATURE                   Location/Qualifiers
REGION                    1..140
                          note = Description of Artificial Sequence: Synthetic
                           polypeptide
MOD_RES                   67
                          note = Any amino acid
source                    1..140
                          mol_type = protein
                          organism = synthetic construct
SEQUENCE: 162
TEKPPGNYKK PKLLYCSNGG HFLRILPDGT VDGTRDRSDQ HIQLQLSAES VGEVYIKSTE  60
TGQYLAXDTD GLLYGSQTPN EECLFLERLE ENHYNTYISK KHAEKNWFVG LKKNGSCKRG  120
PRTHYGQKAI LFLPLPVSSD                                               140

SEQ ID NO: 163            moltype = AA  length = 139
FEATURE                   Location/Qualifiers
REGION                    1..139
                          note = Description of Artificial Sequence: Synthetic
                           polypeptide
MOD_RES                   66
                          note = Any amino acid
source                    1..139
                          mol_type = protein
                          organism = synthetic construct
SEQUENCE: 163
TEKPGNYKKP KLLYCSNGGH FLRILPDGTV DGTRDRSDQH IQLQLSAESV GEVYIKSTET  60
GQYLAXDTDG LLYGSQTPNE ECLFLERLEE NHYNTYISKK HAEKNWFVGL KKNGSCKRGP  120
RTHYGQKAIL FLPLPVSSD                                                139

SEQ ID NO: 164            moltype = AA  length = 142
FEATURE                   Location/Qualifiers
REGION                    1..142
                          note = Description of Artificial Sequence: Synthetic
                           polypeptide
MOD_RES                   69
                          note = Any amino acid
source                    1..142
                          mol_type = protein
                          organism = synthetic construct
SEQUENCE: 164
EKFNLPPGNY KKPKLLYCSN GGHFLRILPD GTVDGTRDRS DQHIQLQLSA ESVGEVYIKS  60
TETGQYLAXD TDGLLYGSQT PNEECLFLER LEENHYNTYI SKKHAEKNWF VGLKKNGSCK  120
RGPRTHYGQK AILFLPLPVS SD                                            142

SEQ ID NO: 165            moltype = AA  length = 141
```

-continued

```
FEATURE              Location/Qualifiers
REGION               1..141
                     note = Description of Artificial Sequence: Synthetic
                      polypeptide
MOD_RES              68
                     note = Any amino acid
source               1..141
                     mol_type = protein
                     organism = synthetic construct
SEQUENCE: 165
EKNLPPGNYK KPKLLYCSNG GHFLRILPDG TVDGTRDRSD QHIQLQLSAE SVGEVYIKST  60
ETGQYLAXDT DGLLYGSQTP NEECLFLERL EENHYNTYIS KKHAEKNWFV GLKKNGSCKR  120
GPRTHYGQKA ILFLPLPVSS D                                            141

SEQ ID NO: 166          moltype = AA   length = 140
FEATURE              Location/Qualifiers
REGION               1..140
                     note = Description of Artificial Sequence: Synthetic
                      polypeptide
MOD_RES              67
                     note = Any amino acid
source               1..140
                     mol_type = protein
                     organism = synthetic construct
SEQUENCE: 166
EKLPPGNYKK PKLLYCSNGG HFLRILPDGT VDGTRDRSDQ HIQLQLSAES VGEVYIKSTE  60
TGQYLAXDTD GLLYGSQTPN EECLFLERLE ENHYNTYISK KHAEKNWFVG LKKNGSCKRG  120
PRTHYGQKAI LFLPLPVSSD                                              140

SEQ ID NO: 167          moltype = AA   length = 139
FEATURE              Location/Qualifiers
REGION               1..139
                     note = Description of Artificial Sequence: Synthetic
                      polypeptide
MOD_RES              66
                     note = Any amino acid
source               1..139
                     mol_type = protein
                     organism = synthetic construct
SEQUENCE: 167
EKPPGNYKKP KLLYCSNGGH FLRILPDGTV DGTRDRSDQH IQLQLSAESV GEVYIKSTET  60
GQYLAXDTDG LLYGSQTPNE ECLFLERLEE NHYNTYISKK HAEKNWFVGL KKNGSCKRGP  120
RTHYGQKAIL FLPLPVSSD                                               139

SEQ ID NO: 168          moltype = AA   length = 138
FEATURE              Location/Qualifiers
REGION               1..138
                     note = Description of Artificial Sequence: Synthetic
                      polypeptide
MOD_RES              65
                     note = Any amino acid
source               1..138
                     mol_type = protein
                     organism = synthetic construct
SEQUENCE: 168
EKPGNYKKPK LLYCSNGGHF LRILPDGTVD GTRDRSDQHI QLQLSAESVG EVYIKSTETG  60
QYLAXDTDGL LYGSQTPNEE CLFLERLEEN HYNTYISKKH AEKNWFVGLK KNGSCKRGPR  120
THYGQKAILF LPLPVSSD                                                138

SEQ ID NO: 169          moltype = AA   length = 141
FEATURE              Location/Qualifiers
REGION               1..141
                     note = Description of Artificial Sequence: Synthetic
                      polypeptide
MOD_RES              68
                     note = Any amino acid
source               1..141
                     mol_type = protein
                     organism = synthetic construct
SEQUENCE: 169
KFNLPPGNYK KPKLLYCSNG GHFLRILPDG TVDGTRDRSD QHIQLQLSAE SVGEVYIKST  60
ETGQYLAXDT DGLLYGSQTP NEECLFLERL EENHYNTYIS KKHAEKNWFV GLKKNGSCKR  120
GPRTHYGQKA ILFLPLPVSS D                                            141

SEQ ID NO: 170          moltype = AA   length = 140
FEATURE              Location/Qualifiers
REGION               1..140
                     note = Description of Artificial Sequence: Synthetic
                      polypeptide
```

```
MOD_RES                  67
                         note = Any amino acid
source                   1..140
                         mol_type = protein
                         organism = synthetic construct
SEQUENCE: 170
KNLPPGNYKK PKLLYCSNGG HFLRILPDGT VDGTRDRSDQ HIQLQLSAES VGEVYIKSTE  60
TGQYLAXDTD GLLYGSQTPN EECLFLERLE ENHYNTYISK KHAEKNWFVG LKKNGSCKRG  120
PRTHYGQKAI LFLPLPVSSD                                             140

SEQ ID NO: 171          moltype = AA   length = 139
FEATURE                 Location/Qualifiers
REGION                  1..139
                        note = Description of Artificial Sequence: Synthetic
                         polypeptide
MOD_RES                 66
                        note = Any amino acid
source                  1..139
                        mol_type = protein
                        organism = synthetic construct
SEQUENCE: 171
KLPPGNYKKP KLLYCSNGGH FLRILPDGTV DGTRDRSDQH IQLQLSAESV GEVYIKSTET  60
GQYLAXDTDG LLYGSQTPNE ECLFLERLEE NHYNTYISKK HAEKNWFVGL KKNGSCKRGP  120
RTHYGQKAIL FLPLPVSSD                                              139

SEQ ID NO: 172          moltype = AA   length = 138
FEATURE                 Location/Qualifiers
REGION                  1..138
                        note = Description of Artificial Sequence: Synthetic
                         polypeptide
MOD_RES                 65
                        note = Any amino acid
source                  1..138
                        mol_type = protein
                        organism = synthetic construct
SEQUENCE: 172
KPPGNYKKPK LLYCSNGGHF LRILPDGTVD GTRDRSDQHI QLQLSAESVG EVYIKSTETG  60
QYLAXDTDGL LYGSQTPNEE CLFLERLEEN HYNTYISKKH AEKNWFVGLK KNGSCKRGPR  120
THYGQKAILF LPLPVSSD                                               138

SEQ ID NO: 173          moltype = AA   length = 137
FEATURE                 Location/Qualifiers
REGION                  1..137
                        note = Description of Artificial Sequence: Synthetic
                         polypeptide
MOD_RES                 64
                        note = Any amino acid
source                  1..137
                        mol_type = protein
                        organism = synthetic construct
SEQUENCE: 173
KPGNYKKPKL LYCSNGGHFL RILPDGTVDG TRDRSDQHIQ LQLSAESVGE VYIKSTETGQ  60
YLAXDTDGLL YGSQTPNEEC LFLERLEENH YNTYISKKHA EKNWFVGLKK NGSCKRGPRT  120
HYGQKAILFL PLPVSSD                                                137

SEQ ID NO: 174          moltype = AA   length = 140
FEATURE                 Location/Qualifiers
REGION                  1..140
                        note = Description of Artificial Sequence: Synthetic
                         polypeptide
MOD_RES                 67
                        note = Any amino acid
source                  1..140
                        mol_type = protein
                        organism = synthetic construct
SEQUENCE: 174
FNLPPGNYKK PKLLYSSNGG HFLRILPDGT VDGTRDRSDQ HIQLQLSAES VGEVYIKSTE  60
TGQYLCXDTD GLLYGSQTPN EECLFLERLE ENHYNTYISK KHAEKNWFVG LKKNGSVKRG  120
PRTHYGQKAI LFLPLPVSSD                                             140

SEQ ID NO: 175          moltype = AA   length = 145
FEATURE                 Location/Qualifiers
REGION                  1..145
                        note = Description of Artificial Sequence: Synthetic
                         polypeptide
MOD_RES                 72
                        note = Any amino acid
source                  1..145
                        mol_type = protein
```

```
                            organism = synthetic construct
SEQUENCE: 175
ALTEKFNLPP GNYKKPKLLY SSNGGHFLRI LPDGTVDGTR DRSDQHIQLQ LSAESVGEVY  60
IKSTETGQYL CXDTDGLLYG SQTPNEECLF LERLEENHYN TYISKKHAEK NWFVGLKKNG  120
SVKRGPRTHY GQKAILFLPL PVSSD                                        145

SEQ ID NO: 176          moltype = AA  length = 144
FEATURE                 Location/Qualifiers
REGION                  1..144
                        note = Description of Artificial Sequence: Synthetic
                         polypeptide
MOD_RES                 71
                        note = Any amino acid
source                  1..144
                        mol_type = protein
                        organism = synthetic construct
SEQUENCE: 176
LTEKFNLPPG NYKKPKLLYS SNGGHFLRIL PDGTVDGTRD RSDQHIQLQL SAESVGEVYI  60
KSTETGQYLC XDTDGLLYGS QTPNEECLFL ERLEENHYNT YISKKHAEKN WFVGLKKNGS  120
VKRGPRTHYG QKAILFLPLP VSSD                                         144

SEQ ID NO: 177          moltype = AA  length = 143
FEATURE                 Location/Qualifiers
REGION                  1..143
                        note = Description of Artificial Sequence: Synthetic
                         polypeptide
MOD_RES                 70
                        note = Any amino acid
source                  1..143
                        mol_type = protein
                        organism = synthetic construct
SEQUENCE: 177
TEKFNLPPGN YKKPKLLYSS NGGHFLRILP DGTVDGTRDR SDQHIQLQLS AESVGEVYIK  60
STETGQYLCX DTDGLLYGSQ TPNEECLFLE RLEENHYNTY ISKKHAEKNW FVGLKKNGSV  120
KRGPRTHYGQ KAILFLPLPV SSD                                          143

SEQ ID NO: 178          moltype = AA  length = 142
FEATURE                 Location/Qualifiers
REGION                  1..142
                        note = Description of Artificial Sequence: Synthetic
                         polypeptide
MOD_RES                 69
                        note = Any amino acid
source                  1..142
                        mol_type = protein
                        organism = synthetic construct
SEQUENCE: 178
EKFNLPPGNY KKPKLLYSSN GGHFLRILPD GTVDGTRDRS DQHIQLQLSA ESVGEVYIKS  60
TETGQYLCXD TDGLLYGSQT PNEECLFLER LEENHYNTYI SKKHAEKNWF VGLKKNGSVK  120
RGPRTHYGQK AILFLPLPVS SD                                           142

SEQ ID NO: 179          moltype = AA  length = 141
FEATURE                 Location/Qualifiers
REGION                  1..141
                        note = Description of Artificial Sequence: Synthetic
                         polypeptide
MOD_RES                 68
                        note = Any amino acid
source                  1..141
                        mol_type = protein
                        organism = synthetic construct
SEQUENCE: 179
KFNLPPGNYK KPKLLYSSNG GHFLRILPDG TVDGTRDRSD QHIQLQLSAE SVGEVYIKST  60
ETGQYLCXDT DGLLYGSQTP NEECLFLERL EENHYNTYIS KKHAEKNWFV GLKKNGSVKR  120
GPRTHYGQKA ILFLPLPVSS D                                            141

SEQ ID NO: 180          moltype = AA  length = 141
FEATURE                 Location/Qualifiers
REGION                  1..141
                        note = Description of Artificial Sequence: Synthetic
                         polypeptide
MOD_RES                 68
                        note = Any amino acid
source                  1..141
                        mol_type = protein
                        organism = synthetic construct
SEQUENCE: 180
KFNLPPGNYK KPKLLYSSNG GHFLRILPDG TVDGTRDRSD QHIQLQLSAE SVGEVYIKST  60
ETGQYLCXDT DGLLYGSQTP NEECLFLERL EENHYNTYIS KKHAEKNWFV GLKKNGSVKR  120
```

-continued

```
GPRTHYGQKA ILFLPLPVSS D                                                        141

SEQ ID NO: 181          moltype = AA   length = 144
FEATURE                 Location/Qualifiers
REGION                  1..144
                        note = Description of Artificial Sequence: Synthetic
                         polypeptide
MOD_RES                 71
                        note = Any amino acid
source                  1..144
                        mol_type = protein
                        organism = synthetic construct
SEQUENCE: 181
ALTEKNLPPG NYKKPKLLYS SNGGHFLRIL PDGTVDGTRD RSDQHIQLQL SAESVGEVYI   60
KSTETGQYLC XDTDGLLYGS QTPNEECLFL ERLEENHYNT YISKKHAEKN WFVGLKKNGS   120
VKRGPRTHYG QKAILFLPLP VSSD                                          144

SEQ ID NO: 182          moltype = AA   length = 143
FEATURE                 Location/Qualifiers
REGION                  1..143
                        note = Description of Artificial Sequence: Synthetic
                         polypeptide
MOD_RES                 70
                        note = Any amino acid
source                  1..143
                        mol_type = protein
                        organism = synthetic construct
SEQUENCE: 182
ALTEKLPPGN YKKPKLLYSS NGGHFLRILP DGTVDGTRDR SDQHIQLQLS AESVGEVYIK   60
STETGQYLCX DTDGLLYGSQ TPNEECLFLE RLEENHYNTY ISKKHAEKNW FVGLKKNGSV   120
KRGPRTHYGQ KAILFLPLPV SSD                                           143

SEQ ID NO: 183          moltype = AA   length = 142
FEATURE                 Location/Qualifiers
REGION                  1..142
                        note = Description of Artificial Sequence: Synthetic
                         polypeptide
MOD_RES                 69
                        note = Any amino acid
source                  1..142
                        mol_type = protein
                        organism = synthetic construct
SEQUENCE: 183
ALTEKPPGNY KKPKLLYSSN GGHFLRILPD GTVDGTRDRS DQHIQLQLSA ESVGEVYIKS   60
TETGQYLCXD TDGLLYGSQT PNEECLFLER LEENHYNTYI SKKHAEKNWF VGLKKNGSVK   120
RGPRTHYGQK AILFLPLPVS SD                                            142

SEQ ID NO: 184          moltype = AA   length = 141
FEATURE                 Location/Qualifiers
REGION                  1..141
                        note = Description of Artificial Sequence: Synthetic
                         polypeptide
MOD_RES                 68
                        note = Any amino acid
source                  1..141
                        mol_type = protein
                        organism = synthetic construct
SEQUENCE: 184
ALTEKPGNYK KPKLLYSSNG GHFLRILPDG TVDGTRDRSD QHIQLQLSAE SVGEVYIKST   60
ETGQYLCXDT DGLLYGSQTP NEECLFLERL EENHYNTYIS KKHAEKNWFV GLKKNGSVKR   120
GPRTHYGQKA ILFLPLPVSS D                                             141

SEQ ID NO: 185          moltype = AA   length = 144
FEATURE                 Location/Qualifiers
REGION                  1..144
                        note = Description of Artificial Sequence: Synthetic
                         polypeptide
MOD_RES                 71
                        note = Any amino acid
source                  1..144
                        mol_type = protein
                        organism = synthetic construct
SEQUENCE: 185
LTEKFNLPPG NYKKPKLLYS SNGGHFLRIL PDGTVDGTRD RSDQHIQLQL SAESVGEVYI   60
KSTETGQYLC XDTDGLLYGS QTPNEECLFL ERLEENHYNT YISKKHAEKN WFVGLKKNGS   120
VKRGPRTHYG QKAILFLPLP VSSD                                          144

SEQ ID NO: 186          moltype = AA   length = 143
FEATURE                 Location/Qualifiers
```

-continued

```
REGION                    1..143
                          note = Description of Artificial Sequence: Synthetic
                           polypeptide
MOD_RES                   70
                          note = Any amino acid
source                    1..143
                          mol_type = protein
                          organism = synthetic construct
SEQUENCE: 186
LTEKNLPPGN YKKPKLLYSS NGGHFLRILP DGTVDGTRDR SDQHIQLQLS AESVGEVYIK  60
STETGQYLCX DTDGLLYGSQ TPNEECLFLE RLEENHYNTY ISKKHAEKNW FVGLKKNGSV  120
KRGPRTHYGQ KAILFLPLPV SSD                                          143

SEQ ID NO: 187            moltype = AA  length = 142
FEATURE                   Location/Qualifiers
REGION                    1..142
                          note = Description of Artificial Sequence: Synthetic
                           polypeptide
MOD_RES                   69
                          note = Any amino acid
source                    1..142
                          mol_type = protein
                          organism = synthetic construct
SEQUENCE: 187
LTEKLPPGNY KKPKLLYSSN GGHFLRILPD GTVDGTRDRS DQHIQLQLSA ESVGEVYIKS  60
TETGQYLCXD TDGLLYGSQT PNEECLFLER LEENHYNTYI SKKHAEKNWF VGLKKNGSVK  120
RGPRTHYGQK AILFLPLPVS SD                                           142

SEQ ID NO: 188            moltype = AA  length = 141
FEATURE                   Location/Qualifiers
REGION                    1..141
                          note = Description of Artificial Sequence: Synthetic
                           polypeptide
MOD_RES                   68
                          note = Any amino acid
source                    1..141
                          mol_type = protein
                          organism = synthetic construct
SEQUENCE: 188
LTEKPPGNYK KPKLLYSSNG GHFLRILPDG TVDGTRDRSD QHIQLQLSAE SVGEVYIKST  60
ETGQYLCXDT DGLLYGSQTP NEECLFLERL EENHYNTYIS KKHAEKNWFV GLKKNGSVKR  120
GPRTHYGQKA ILFLPLPVSS D                                            141

SEQ ID NO: 189            moltype = AA  length = 140
FEATURE                   Location/Qualifiers
REGION                    1..140
                          note = Description of Artificial Sequence: Synthetic
                           polypeptide
MOD_RES                   67
                          note = Any amino acid
source                    1..140
                          mol_type = protein
                          organism = synthetic construct
SEQUENCE: 189
LTEKPGNYKK PKLLYSSNGG HFLRILPDGT VDGTRDRSDQ HIQLQLSAES VGEVYIKSTE  60
TGQYLCXDTD GLLYGSQTPN EECLFLERLE ENHYNTYISK KHAEKNWFVG LKKNGSVKRG  120
PRTHYGQKAI LFLPLPVSSD                                              140

SEQ ID NO: 190            moltype = AA  length = 143
FEATURE                   Location/Qualifiers
REGION                    1..143
                          note = Description of Artificial Sequence: Synthetic
                           polypeptide
MOD_RES                   70
                          note = Any amino acid
source                    1..143
                          mol_type = protein
                          organism = synthetic construct
SEQUENCE: 190
TEKFNLPPGN YKKPKLLYSS NGGHFLRILP DGTVDGTRDR SDQHIQLQLS AESVGEVYIK  60
STETGQYLCX DTDGLLYGSQ TPNEECLFLE RLEENHYNTY ISKKHAEKNW FVGLKKNGSV  120
KRGPRTHYGQ KAILFLPLPV SSD                                          143

SEQ ID NO: 191            moltype = AA  length = 142
FEATURE                   Location/Qualifiers
REGION                    1..142
                          note = Description of Artificial Sequence: Synthetic
                           polypeptide
MOD_RES                   69
```

-continued

```
                            note = Any amino acid
source                      1..142
                            mol_type = protein
                            organism = synthetic construct
SEQUENCE: 191
TEKNLPPGNY KKPKLLYSSN GGHFLRILPD GTVDGTRDRS DQHIQLQLSA ESVGEVYIKS  60
TETGQYLCXD TDGLLYGSQT PNEECLFLER LEENHYNTYI SKKHAEKNWF VGLKKNGSVK  120
RGPRTHYGQK AILFLPLPVS SD                                          142

SEQ ID NO: 192           moltype = AA  length = 141
FEATURE                  Location/Qualifiers
REGION                   1..141
                         note = Description of Artificial Sequence: Synthetic
                          polypeptide
MOD_RES                  68
                         note = Any amino acid
source                   1..141
                         mol_type = protein
                         organism = synthetic construct
SEQUENCE: 192
TEKLPPGNYK KPKLLYSSNG GHFLRILPDG TVDGTRDRSD QHIQLQLSAE SVGEVYIKST  60
ETGQYLCXDT DGLLYGSQTP NEECLFLERL EENHYNTYIS KKHAEKNWFV GLKKNGSVKR  120
GPRTHYGQKA ILFLPLPVSS D                                           141

SEQ ID NO: 193           moltype = AA  length = 140
FEATURE                  Location/Qualifiers
REGION                   1..140
                         note = Description of Artificial Sequence: Synthetic
                          polypeptide
MOD_RES                  67
                         note = Any amino acid
source                   1..140
                         mol_type = protein
                         organism = synthetic construct
SEQUENCE: 193
TEKPPGNYKK PKLLYSSNGG HFLRILPDGT VDGTRDRSDQ HIQLQLSAES VGEVYIKSTE  60
TGQYLCXDTD GLLYGSQTPN EECLFLERLE ENHYNTYISK KHAEKNWFVG LKKNGSVKRG  120
PRTHYGQKAI LFLPLPVSSD                                             140

SEQ ID NO: 194           moltype = AA  length = 139
FEATURE                  Location/Qualifiers
REGION                   1..139
                         note = Description of Artificial Sequence: Synthetic
                          polypeptide
MOD_RES                  66
                         note = Any amino acid
source                   1..139
                         mol_type = protein
                         organism = synthetic construct
SEQUENCE: 194
TEKPGNYKKP KLLYSSNGGH FLRILPDGTV DGTRDRSDQH IQLQLSAESV GEVYIKSTET  60
GQYLCXDTDG LLYGSQTPNE ECLFLERLEE NHYNTYISKK HAEKNWFVGL KKNGSVKRGP  120
RTHYGQKAIL FLPLPVSSD                                              139

SEQ ID NO: 195           moltype = AA  length = 142
FEATURE                  Location/Qualifiers
REGION                   1..142
                         note = Description of Artificial Sequence: Synthetic
                          polypeptide
MOD_RES                  69
                         note = Any amino acid
source                   1..142
                         mol_type = protein
                         organism = synthetic construct
SEQUENCE: 195
EKFNLPPGNY KKPKLLYSSN GGHFLRILPD GTVDGTRDRS DQHIQLQLSA ESVGEVYIKS  60
TETGQYLCXD TDGLLYGSQT PNEECLFLER LEENHYNTYI SKKHAEKNWF VGLKKNGSVK  120
RGPRTHYGQK AILFLPLPVS SD                                          142

SEQ ID NO: 196           moltype = AA  length = 141
FEATURE                  Location/Qualifiers
REGION                   1..141
                         note = Description of Artificial Sequence: Synthetic
                          polypeptide
MOD_RES                  68
                         note = Any amino acid
source                   1..141
                         mol_type = protein
                         organism = synthetic construct
```

```
SEQUENCE: 196
EKNLPPGNYK KPKLLYSSNG GHFLRILPDG TVDGTRDRSD QHIQLQLSAE SVGEVYIKST   60
ETGQYLCXDT DGLLYGSQTP NEECLFLERL EENHYNTYIS KKHAEKNWFV GLKKNGSVKR  120
GPRTHYGQKA ILFLPLPVSS D                                           141

SEQ ID NO: 197          moltype = AA   length = 140
FEATURE                 Location/Qualifiers
REGION                  1..140
                        note = Description of Artificial Sequence: Synthetic
                         polypeptide
MOD_RES                 67
                        note = Any amino acid
source                  1..140
                        mol_type = protein
                        organism = synthetic construct
SEQUENCE: 197
EKLPPGNYKK PKLLYSSNGG HFLRILPDGT VDGTRDRSDQ HIQLQLSAES VGEVYIKSTE   60
TGQYLCXDTD GLLYGSQTPN EECLFLERLE ENHYNTYISK KHAEKNWFVG LKKNGSVKRG  120
PRTHYGQKAI LFLPLPVSSD                                              140

SEQ ID NO: 198          moltype = AA   length = 139
FEATURE                 Location/Qualifiers
REGION                  1..139
                        note = Description of Artificial Sequence: Synthetic
                         polypeptide
MOD_RES                 66
                        note = Any amino acid
source                  1..139
                        mol_type = protein
                        organism = synthetic construct
SEQUENCE: 198
EKPPGNYKKP KLLYSSNGGH FLRILPDGTV DGTRDRSDQH IQLQLSAESV GEVYIKSTET   60
GQYLCXDTDG LLYGSQTPNE ECLFLERLEE NHYNTYISKK HAEKNWFVGL KKNGSVKRGP  120
RTHYGQKAIL FLPLPVSSD                                               139

SEQ ID NO: 199          moltype = AA   length = 138
FEATURE                 Location/Qualifiers
REGION                  1..138
                        note = Description of Artificial Sequence: Synthetic
                         polypeptide
MOD_RES                 65
                        note = Any amino acid
source                  1..138
                        mol_type = protein
                        organism = synthetic construct
SEQUENCE: 199
EKPGNYKKPK LLYSSNGGHF LRILPDGTVD GTRDRSDQHI QLQLSAESVG EVYIKSTETG   60
QYLCXDTDGL LYGSQTPNEE CLFLERLEEN HYNTYISKKH AEKNWFVGLK KNGSVKRGPR  120
THYGQKAILF LPLPVSSD                                                138

SEQ ID NO: 200          moltype = AA   length = 141
FEATURE                 Location/Qualifiers
REGION                  1..141
                        note = Description of Artificial Sequence: Synthetic
                         polypeptide
MOD_RES                 68
                        note = Any amino acid
source                  1..141
                        mol_type = protein
                        organism = synthetic construct
SEQUENCE: 200
KFNLPPGNYK KPKLLYSSNG GHFLRILPDG TVDGTRDRSD QHIQLQLSAE SVGEVYIKST   60
ETGQYLCXDT DGLLYGSQTP NEECLFLERL EENHYNTYIS KKHAEKNWFV GLKKNGSVKR  120
GPRTHYGQKA ILFLPLPVSS D                                           141

SEQ ID NO: 201          moltype = AA   length = 140
FEATURE                 Location/Qualifiers
REGION                  1..140
                        note = Description of Artificial Sequence: Synthetic
                         polypeptide
MOD_RES                 67
                        note = Any amino acid
source                  1..140
                        mol_type = protein
                        organism = synthetic construct
SEQUENCE: 201
KNLPPGNYKK PKLLYSSNGG HFLRILPDGT VDGTRDRSDQ HIQLQLSAES VGEVYIKSTE   60
TGQYLCXDTD GLLYGSQTPN EECLFLERLE ENHYNTYISK KHAEKNWFVG LKKNGSVKRG  120
PRTHYGQKAI LFLPLPVSSD                                              140
```

-continued

```
SEQ ID NO: 202          moltype = AA   length = 139
FEATURE                 Location/Qualifiers
REGION                  1..139
                        note = Description of Artificial Sequence: Synthetic
                         polypeptide
MOD_RES                 66
                        note = Any amino acid
source                  1..139
                        mol_type = protein
                        organism = synthetic construct
SEQUENCE: 202
KLPPGNYKKP KLLYSSNGGH FLRILPDGTV DGTRDRSDQH IQLQLSAESV GEVYIKSTET   60
GQYLCXDTDG LLYGSQTPNE ECLFLERLEE NHYNTYISKK HAEKNWFVGL KKNGSVKRGP  120
RTHYGQKAIL FLPLPVSSD                                               139

SEQ ID NO: 203          moltype = AA   length = 138
FEATURE                 Location/Qualifiers
REGION                  1..138
                        note = Description of Artificial Sequence: Synthetic
                         polypeptide
MOD_RES                 65
                        note = Any amino acid
source                  1..138
                        mol_type = protein
                        organism = synthetic construct
SEQUENCE: 203
KPPGNYKKPK LLYSSNGGHF LRILPDGTVD GTRDRSDQHI QLQLSAESVG EVYIKSTETG   60
QYLCXDTDGL LYGSQTPNEE CLFLERLEEN HYNTYISKKH AEKNWFVGLK KNGSVKRGPR  120
THYGQKAILF LPLPVSSD                                                138

SEQ ID NO: 204          moltype = AA   length = 137
FEATURE                 Location/Qualifiers
REGION                  1..137
                        note = Description of Artificial Sequence: Synthetic
                         polypeptide
MOD_RES                 64
                        note = Any amino acid
source                  1..137
                        mol_type = protein
                        organism = synthetic construct
SEQUENCE: 204
KPGNYKKPKL LYSSNGGHFL RILPDGTVDG TRDRSDQHIQ LQLSAESVGE VYIKSTETGQ   60
YLCXDTDGLL YGSQTPNEEC LFLERLEENH YNTYISKKHA EKNWFVGLKK NGSVKRGPRT  120
HYGQKAILFL PLPVSSD                                                 137

SEQ ID NO: 205          moltype = AA   length = 140
FEATURE                 Location/Qualifiers
REGION                  1..140
                        note = Description of Artificial Sequence: Synthetic
                         polypeptide
source                  1..140
                        mol_type = protein
                        organism = synthetic construct
SEQUENCE: 205
FNLPPGNYKK PVLLYCSNGG HFLRILPDGT VDGTRDRSDQ HIQLQLSAES VGEVYIKSTE   60
TGQYLAMDTD GLLYGSQTPN EECLFLERLE ENHYNTYISK KHAEKNWFVG LKKNGSVKRG  120
PRTHYGQKAI LFLVLPVSSD                                              140

SEQ ID NO: 206          moltype = AA   length = 140
FEATURE                 Location/Qualifiers
REGION                  1..140
                        note = Description of Artificial Sequence: Synthetic
                         polypeptide
source                  1..140
                        mol_type = protein
                        organism = synthetic construct
SEQUENCE: 206
FNLPPGNYKK PKLLYSSNGG HFLRILPDGT VDGTRDRSDQ HIQLQLSAES VGEVYIKSTE   60
TGQYLCMDTD GLLYGSQTPN EECLFLERLE ENHYNTYISK KHAEKNWFVG LKKNGSVKRG  120
PRTHYGQKAI LFLPLPVSSD                                              140

SEQ ID NO: 207          moltype = AA   length = 145
FEATURE                 Location/Qualifiers
REGION                  1..145
                        note = Description of Artificial Sequence: Synthetic
                         polypeptide
source                  1..145
                        mol_type = protein
```

```
                                  -continued organism = synthetic construct
SEQUENCE: 207
MALTEKNLPP GNYKKPKLLY SSNGGHFLRI LPDGTVDGTR DRSDQHIQLQ LSAESVGEVY   60
IKSTETGQYL CMDTDGLLYG SQTPNEECLF LERLEENHYN TYISKKHAEK NWFVGLKKNG  120
SVKRGPRTHY GQKAILFLPL PVSSD                                       145
```

RECOMBINANT MODIFIED FIBROBLAST GROWTH FACTORS AND THERAPEUTIC USES THEREOF

CROSS-REFERENCE

This application is a Divisional of U.S. application Ser. No. 16/611,182, filed Nov. 5, 2019, which is a U.S. National Stage of International Application No. PCT/US2018/031189, filed May 4, 2018, which claims benefit of U.S. Provisional Patent Application No. 62/502,529 filed on May 5, 2017, U.S. Provisional Patent Application No. 62/502,540 filed on May 5, 2017, and U.S. Provisional Patent Application No. 62/584,624 filed on Nov. 10, 2017, the content of each of which is incorporated by reference herein in its entirety.

REFERENCE TO SEQUENCE LISTING SUBMITTED ELECTRONICALLY

This application incorporates by reference a Sequence Listing submitted with this application as a text file entitled "Trefoil 45341-705.401_SL.xml" created on Nov. 29, 2022 and having a size of 312,378 bytes.

FIELD OF THE INVENTION

Described herein are modified fibroblast growth factor (FGF) polypeptides, pharmaceutical compositions and medicaments that include such modified FGF polypeptides, and methods of using such modified FGF polypeptides to treat or prevent conditions that benefit from administration of FGFs.

BACKGROUND OF THE INVENTION

FGFs are large polypeptides widely expressed in developing and adult tissues (Baird et al., Cancer Cells, 3:239-243, 1991) and play roles in multiple physiological functions (McKeehan et al., Prog. Nucleic Acid Res. Mol. Biol. 59:135-176, 1998; Burgess, W. H. et al., Annu Rev. Biochem. 58:575-606 (1989). The FGF family includes at least twenty-two members (Reuss et al., Cell Tissue Res. 313:139-157 (2003)).

SUMMARY OF THE INVENTION

Provided herein in one embodiment is a recombinant modified FGF-1 polypeptide comprising the sequence set forth as SEQ ID NO: 1 with one or more mutations, wherein the polypeptide comprises an N-terminal methionine residue positioned upstream to the first residue of SEQ ID NO: 1. In some embodiments, the polypeptide further comprises an extension peptide positioned between the N-terminal methionine residue and the first residue of SEQ ID NO: 1. In some embodiments, the extension peptide comprises one or more amino acid residues of SEQ ID NO: 3. In some embodiments, the extension peptide comprises any one of the sequences set forth in SEQ ID NOS. 4-5. In some embodiments, the extension peptide comprises any one of the sequences of TEK, EK, or K. In some embodiments, the modified FGF-1 polypeptide is the mature form of the polypeptide. In some embodiments, the modified FGF-1 polypeptide comprises a sequence selected from SEQ ID NOS: 14-18.

One embodiment provides a recombinant modified FGF-1 polypeptide comprising the sequence set forth as SEQ ID NO: 1 with one or more mutations, wherein the polypeptide further comprises an extension peptide positioned upstream to the first residue of SEQ ID NO: 1. In some embodiments, the extension peptide comprises one or more amino acids of SEQ ID NO: 3. In some embodiments, the extension peptide comprises any one of the sequences set forth in SEQ ID NOS. 4-5. In some embodiments, the extension peptide comprises any one of the sequences of TEK, EK, or K. In some embodiments, the modified FGF-1 polypeptide is the mature form of the polypeptide. In some embodiments, the modified FGF-1 polypeptide comprises a sequence selected from SEQ ID NOS: 24-28.

One embodiment provides a recombinant modified FGF-1 polypeptide comprising the sequence set forth as SEQ ID NO: 1 with one or more mutations, wherein the polypeptide further comprises a truncation of one or more of the first five residues of SEQ ID NO: 1, and wherein the polypeptide comprises an extension peptide at the N-terminus of the polypeptide. In some embodiments, the modified FGF-1 polypeptide comprises a sequence selected from SEQ ID NOS: 93-117. In some embodiments, the polypeptide further comprises a methionine residue N-terminal to the extension peptide. In some embodiments, the modified FGF-1 polypeptide is the mature form of the polypeptide. In some embodiments, the modified FGF-1 polypeptide comprises a sequence selected from SEQ ID NOS: 118-141 and 207. In some embodiments, the modified FGF-1 polypeptide is expressed in a form that comprises 136 amino acids. In some embodiments, the modified FGF-1 polypeptide comprises at least 141 amino acids in its mature form.

One embodiment provides a recombinant modified FGF-1 polypeptide comprising a mutation at position 67 of SEQ ID NO: 1. In some embodiments, the polypeptide further comprises a truncation of one or more of the first five residues of SEQ ID NO: 1. In some embodiments, the modified FGF-1 polypeptide comprises a sequence selected from SEQ ID NOS: 146-149. In some embodiments, the polypeptide further comprises an extension peptide. In some embodiments, the extension peptide comprises one or more amino acid residues of SEQ ID NO: 3. In some embodiments, the extension peptide comprises any one of the sequences set forth in SEQ ID NOS. 4-5. In some embodiments, the extension peptide comprises any one of the sequences of TEK, EK, or K. In some embodiments, the modified FGF-1 polypeptide is the mature form of the polypeptide. In some embodiments, the modified FGF-1 polypeptide comprises a sequence selected from SEQ ID NOS: 174-204.

One embodiment provides a recombinant modified FGF-1 polypeptide comprising a sequence as set forth in SEQ ID NO: 2. In some embodiments, the modified FGF-1 polypeptide is the mature form of the polypeptide. In some embodiments, the modified FGF-1 polypeptide comprises one or more mutations selected from the group consisting of: Cys16Ser, Ala66Cys, and Cys117Val.

One embodiment provides a recombinant modified FGF-1 polypeptide, wherein the modified FGF-1 comprises one or more mutations of SEQ ID NO: 1, said mutation is selected from the group consisting of: Lys12Val, Cys16Ser, Ala66Cys, Cys117Val, and Pro134Val, and wherein the modified FGF-1 polypeptide further comprises at least one residue of the peptide ALTEK.

One embodiment provides a recombinant modified FGF-1 polypeptide, comprising the following mutations of SEQ ID NO: 1: Cys16Ser, Ala66Cys, and Cys117Val, wherein the modified FGF-1 polypeptide comprises a methionine residue positioned upstream to the first residue of SEQ ID NO: 1, and at least one residue of the peptide ALTEK located between the N-terminal methionine and position 1 of SEQ ID NO: 1. In some embodiments, the modified FGF-1 polypeptide is not expressed with an extension peptide and is produced by a method that does not involve a step of removing an extension peptide.

In one embodiment is provided a pharmaceutical composition comprising the recombinant polypeptide of any one of the embodiments described above. In some embodiments, the pharmaceutical composition further comprises a pharmaceutically acceptable carrier, excipient, or diluent. In some embodiments, the pharmaceutical composition is a liquid ophthalmic formulation. In some embodiments, the pharmaceutical formulation is administered topically, microneedle into the cornea, or intracamerally.

Provided herein in one embodiment is a method for producing a recombinant modified FGF-1 polypeptide, the method comprising: expressing the modified FGF-1 polypeptide in a host cell and maturing the expressed polypeptide in the cytoplasm of the host cell, wherein the modified FGF-1 polypeptide comprises one or more mutations of SEQ ID NO: 1, and is expressed with an N-terminal methionine residue positioned upstream to the first residue of SEQ ID NO: 1.

Provided herein in one embodiment is a method for producing a recombinant modified FGF-1 polypeptide, the method comprising: expressing the modified FGF-1 polypeptide in a host cell and maturing the expressed polypeptide in the cytoplasm of the host cell, wherein the modified FGF-1 polypeptide comprises one or more mutations of SEQ ID NO: 1, an extension peptide between the N-terminal residue and position 1 of SEQ ID NO: 1, and is expressed with an N-terminal methionine residue.

Provided herein in one embodiment is a method for producing a recombinant modified FGF-1 polypeptide, the method comprising: expressing the modified FGF-1 polypeptide in a host cell and maturing the expressed polypeptide in the cytoplasm of the host cell, wherein the modified FGF-1 polypeptide comprises one or more mutations of SEQ ID NO: 1, an extension peptide fragment, a truncation of one or more of the first five residues of SEQ ID NO:1, and wherein the polypeptide is expressed with an N-terminal methionine residue positioned upstream to the first residue of SEQ ID NO: 1. In some embodiments, the N-terminal methionine residue is retained during maturation of the polypeptide. In some embodiments, the N-terminal methionine residue is cleaved off of the polypeptide, by a cleavage enzyme, during maturation of the polypeptide. In some embodiments, the cleavage enzyme is methionine aminopeptidase (metAP). In some embodiments, the metAP is bacterial metAP, yeast metAP, or human metAP. In some embodiments, the cleavage enzyme is bacterial metAP. In some embodiments, the method comprises expressing a modified FGF-1 polypeptide comprising a sequence as set forth in SEQ ID NO: 14 or SEQ ID NO: 16. In some embodiments, the method comprises expressing a modified FGF-1 polypeptide comprising a sequence as set forth in SEQ ID NO: 2. In some embodiments, SEQ ID NO: 2 is the sequence of the polypeptide after maturation in the cytoplasm of the host cell.

One embodiment provides a method for producing a recombinant modified FGF-1 polypeptide, the method comprising: expressing the modified FGF-1 polypeptide in a host cell and maturing the expressed polypeptide in the cytoplasm of the host cell, wherein the modified FGF-1 polypeptide comprises a mutation at position 67 of SEQ ID NO: 1. In some embodiments, the modified FGF-1 polypeptide further comprises an extension peptide fragment, and a truncation of one or more of the first five residues of SEQ ID NO: 1, and wherein the polypeptide is expressed with an N-terminal methionine residue positioned upstream to the first residue of SEQ ID NO: 1. In some embodiments, the method comprises cleavage of the N-terminal methionine residue using cyanogen bromide.

One embodiment provides a method for producing a recombinant modified FGF-1 polypeptide according to any one of the above described embodiments, the method comprising: expressing the modified FGF-1 polypeptide in a host cell, binding the expressed polypeptide to an affinity material via an affinity tag; cleaving the affinity tag to release the polypeptide, and eluting the polypeptide from the affinity material using an agent. In some embodiments, the affinity tag comprises poly-histidine, poly-lysine, poly-aspartic acid, or poly-glutamic acid. In some embodiments, the agent comprises methanol, 2-propanol, or another alcohol, dimethyl sulfoxide (DMSO), dimethylformamide (DMF), acetone, or another organic solvent. In some embodiments, the affinity material is a resin framework. In some embodiments, the affinity material is an ion exchange resin. In some embodiments, the polypeptide is expressed in the cytoplasm of the host cell and is not secreted into the periplasmic space. In some embodiments, the host cell is microbial. In some embodiments, the microbial expression system is selected from the group consisting of an *E. coli* expression system, a *Caulobacter* crescent expression system, and a *Proteus mirabilis* expression system. In some embodiments, the microbial expression system is an *E. coli* expression system.

One embodiment provides a method of treating or preventing an ocular disease, disorder or condition in a mammal comprising administering to the mammal a modified FGF-1 according to this disclosure or a pharmaceutical composition according to this disclosure. In some embodiments, the ocular disease, disorder or condition is a disease, disorder, or condition of the cornea or ocular surface. In some embodiments, the ocular disease, disorder or condition is a disease, disorder, or condition of the corneal endothelium. In some embodiments, the disease, disorder, or condition of the corneal endothelium is Fuch's dystrophy, bullous keratopathy, congenital hereditary endothelial dystrophy 1, congenital hereditary endothelial dystrophy 2, posterior polymorphous corneal dystrophy, or a dry eye syndrome. In some embodiments, the ocular disease, disorder or condition is Fuch's dystrophy. In some embodiments, the ocular disease, disorder or condition is a disease, disorder, or condition of the corneal epithelium. In some embodiments, the disease, disorder, or condition of the corneal epithelium is a dry eye syndrome or corneal epithelial damage from corneal surgery or transplantation. In some embodiments, the corneal surgery is photorefractive keratotomy (PRK) or laser-assisted in situ keratomileusis (LASIK). In some embodiments, the ocular disease, disorder or condition is a disease, disorder, or condition of the corneal stroma. In some embodiments, the disease, disorder, or condition of the corneal stroma is keratoconus, lattice corneal dystrophy, granular corneal dystrophy, macular corneal dystrophy, Schnyder crystalline corneal dystrophy, congenital stromal corneal dystrophy, or fleck corneal dystrophy.

One embodiment provides a method of transplanting corneal cells to a mammal or enhancing the success of cell transplantation comprising treating the corneal cells to be transplanted with a modified FGF-1 according to any one of the above described embodiments, prior to, during or after transplanting the corneal cells to the mammal. One embodiment provides a method of preventing scarring during tissue regeneration comprising administering a modified FGF-1 according to any one of the above described embodiments. In some embodiments, the modified FGF-1 is administered to a mammal after undergoing a trabeculectomy.

One embodiment provides a method of treating or preventing a chemical or vesicant induced injury in a patient, the method comprising administering to the patient a modified FGF-1 polypeptide according to any one of the above described embodiments. In some embodiments, the chemical or vesicant induced injury is an ocular injury or a skin injury. In some embodiments, the ocular injury is a corneal injury.

One embodiment provides a method of treatment of corneal injury in a patient, the method comprising administering a modified FGF-1 polypeptide according to this disclosure or a pharmaceutical composition according to this disclosure, wherein the corneal injury is induced by a chemical or a vesicant, and wherein the administering the modified FGF-1 promotes regeneration of cornea, prevents degeneration of the cornea, and prevents long term sequelae to the chemical injury. In some embodiments, the modified FGF-1 is administered over a period of about 7 days to about 40 years to prevent degeneration of corneal tissue. In some embodiments, the corneal tissue comprises corneal epithelium, stroma, corneal endothelium, or corneal innervation. In some embodiments, the corneal injury is a stromal injury. In some embodiments, the stromal injury comprises stromal scarring and corneal opacity.

One embodiment provides a method of preventing long-term corneal injury in a patient, the method comprising administering a modified FGF-1 polypeptide according to this disclosure or a pharmaceutical composition according to this disclosure, wherein the corneal injury is caused by a chemical or a vesicant agent. In some embodiments, the corneal injury is corneal endothelial injury. In some embodiments, administering the modified FGF-1 polypeptide enhances the function of corneal endothelial cells and prevents or reduces long term degeneration of the cornea. In some embodiments, administering the modified FGF-1 polypeptide prevents corneal edema and secondary anterior keratopathies. In some embodiments, administering the modified FGF-1 polypeptide prevents loss of corneal endothelial cells. In some embodiments, the corneal injury is a stromal injury. In some embodiments, the stromal injury comprises stromal scarring and corneal opacity. In some embodiments, the corneal injury is mustard gas keratopathy (MGK). In some embodiments, administering the modified FGF-1 polypeptide results in amelioration of histopathological conditions associated with MGK. In some embodiments, the histopathological conditions include hyperplasia of corneal epithelial layer and epithelial-stromal cell separation. In some embodiments, administering the modified FGF-1 polypeptide results in reduction in edema and elimination of corneal erosions. In some embodiments, the corneal erosion is characterized by de-epithelialization of the cornea. In some embodiments, administering the modified FGF-1 polypeptide reduces the severity of corneal de-epithelialization. In some embodiments, administering the modified FGF-1 polypeptide results in faster re-epithelialization of the cornea.

One embodiment provides a method of regenerating ocular surface epithelium in a patient exposed to a chemical or a vesicant, the method comprising ocular administration of a modified FGF-1 polypeptide according to any one of the above described embodiments. In some embodiments, the ocular surface epithelium is corneal epithelium.

One embodiment provides a method of preventing ocular epithelial injury in a patient exposed to a chemical or a vesicant, the method comprising ocular administration of a modified FGF-1 polypeptide according to any one of the above described embodiments. In some embodiments, the ocular injury is corneal injury caused by exposure to a vesicant. In some embodiments, the corneal injury is corneal epithelial detachment. In some embodiments, administering the modified FGF-1 polypeptide results in reduction in the severity of corneal epithelial detachment following exposure to the vesicant. In some embodiments, administering the modified FGF-1 polypeptide results in reduction in edema and elimination of corneal erosions. In some embodiments, the corneal erosion is characterized by de-epithelialization of the cornea. In some embodiments, administering the modified FGF-1 polypeptide reduces the severity of corneal de-epithelialization. In some embodiments, administering the modified FGF-1 polypeptide results in faster re-epithelialization of the cornea. In some embodiments, the modified FGF-1 polypeptide is administered over a period of up to two weeks or until complete regeneration of the corneal epithelium. In some embodiments, a first dose of the modified FGF-1 polypeptide is administered within 48 hours after exposure to the vesicant. In some embodiments, administering the chemical comprises chlorine gas, phosgene, an alkali, or an acid. In some embodiments, the vesicant comprises sulfur mustard (SM), nitrogen mustard (NM), lewisite, or half mustard (2-chloroethyl ethyl sulfide (CEES)). In some embodiments, the vesicant is NM. In some embodiments, administering the modified FGF-1 polypeptide suppresses NM induced up-regulation of ADAM17. In some embodiments, the chemical or vesicant induced injury is chemical burn. In some embodiments, administering the chemical burn is caused by chlorine gas, phosgene, an alkali, or an acid. In some embodiments, administering the modified FGF-1 polypeptide comprises mutations of positions 16, 66, and 117 of SEQ ID NO: 1. In some embodiments, the mutations are Cys16Ser, Ala66Cys, and Cys117Val. In some embodiments, the modified FGF-1 polypeptide is less susceptible to oxidation upon exposure to a vesicant. In some embodiments, the vesicant is NM.

One embodiment provides a method of treating herpetic keratopathy comprising administering to a mammal modified a FGF-1 polypeptide according to any embodiments of this disclosure or a pharmaceutical composition according to this disclosure. In some embodiments, the herpetic keratopathy is caused by a primary infection by herpes simplex virus. In some embodiments, the herpetic keratopathy is a chronic herpetic keratopathy. In some embodiments, the herpetic keratopathy is secondary to an infection by herpes simplex virus. In some embodiments, the herpetic keratopathy that is secondary to an infection by herpes simplex virus comprises neurotrophic keratopathy. In some embodiments, the modified FGF-1 polypeptide according to this disclosure or the pharmaceutical composition according to this disclosure is administered twice daily. In some embodiments, the modified FGF-1 polypeptide according to this disclosure or the pharmaceutical composition according to this disclosure is administered for a duration of 30 days. In some embodiments, administration of the modified FGF-1 polypeptide according to any this disclosure or the pharmaceutical composition according to this disclosure results in healing of corneal ulcer, reduction of duration of pain and inflammation, reduction in pain and inflammation, reduction in corneal opacity, haze, scarring, or any combinations thereof. In some embodiments, the corneal ulcer comprises a herpetic corneal ulcer. In some embodiments, the mammal is a human.

One embodiment provides a method of treating or preventing chemical or vesicant induced injury in a patient, the method comprising administering to the patient a modified FGF-1 comprising one or more mutations of at positions 12, 16, 66, 117, and 134 of SEQ ID NO: 1. In some embodiments, the chemical or vesicant induced injury is an ocular injury or a skin injury. In some embodiments, the ocular injury is a corneal injury.

One embodiment provides a method of treatment of corneal injury in a patient, the method comprising administering to the patient a modified FGF-1 polypeptide comprising one or more mutations at positions 12, 16, 66, 117, and 134 of SEQ ID NO: 1, wherein the corneal injury is induced by a chemical or a vesicant, and wherein the administering the modified FGF-1 promotes regeneration of cornea, prevents degeneration of the cornea, and prevents long term sequelae to the chemical injury. In some embodiments, the modified FGF-1 is administered over a period of about 7 days to about 40 years to prevent degeneration of corneal tissue. In some embodiments, the corneal tissue comprises corneal epithelium, stroma, corneal endothelium, or corneal innervation. In some embodiments, the corneal injury is a stromal injury. In some embodiments, the stromal injury comprises stromal scarring and corneal opacity.

One embodiment provides a method of preventing long-term corneal injury in a patient, the method comprising administering to the patient a modified FGF-1 polypeptide comprising one or more mutations at positions 12, 16, 66, 117, and 134 of SEQ ID NO: 1, wherein the corneal injury is caused by a chemical or a vesicant agent. In some embodiments, the corneal injury is a corneal endothelial injury. In some embodiments, administering the modified FGF-1 polypeptide enhances the function of the corneal endothelial cells and prevents or reduces long term degeneration of the cornea. In some embodiments, administering the modified FGF-1 polypeptide prevents corneal edema and secondary anterior keratopathies. In some embodiments, administering the modified FGF-1 polypeptide prevents loss of corneal endothelial cells. In some embodiments, the corneal injury is a stromal injury. In some embodiments, the stromal injury comprises stromal scarring and corneal opacity. In some embodiments, the corneal injury is mustard gas keratopathy (MGK). In some embodiments, administration of the modified FGF-1 polypeptide results in amelioration of histopathological conditions associated with MGK. In some embodiments, histopathological conditions include hyperplasia of corneal epithelial layer and epithelial-stromal cell separation. In some embodiments, administration of the modified FGF-1 polypeptide results in reduction in edema and elimination of corneal erosions. In some embodiments, the corneal erosion is characterized by de-epithelialization of the cornea. In some embodiments, administration of the modified FGF-1 polypeptide reduces the severity of corneal de-epithelialization. In some embodiments, administration of the modified FGF-1 polypeptide results in faster re-epithelialization of the cornea.

One embodiment provides a method of regenerating ocular surface epithelium in a patient exposed to a chemical or a vesicant, the method comprising ocular administration of a modified FGF-1 polypeptide comprising one or more mutations at positions 12, 16, 66, 117, and 134 of SEQ ID NO: 1. In some embodiments, the ocular surface epithelium is corneal epithelium.

One embodiment provides a method of preventing ocular epithelial injury in a patient exposed to a chemical or a vesicant, the method comprising ocular administration of a modified FGF-1 polypeptide comprising one or more mutations at positions 12, 16, 66, 117, and 134 of SEQ ID NO: 1. In some embodiments, the ocular injury is corneal injury caused by exposure to a vesicant. In some embodiments, the corneal injury is corneal epithelial detachment. In some embodiments, administration of the modified FGF-1 polypeptide results in reduction in the severity of corneal epithelial detachment following exposure to the vesicant. In some embodiments, administration of the modified FGF-1 polypeptide results in reduction in edema and elimination of corneal erosions. In some embodiments, the corneal erosion is characterized by de-epithelialization of the cornea. In some embodiments, administration of the modified FGF-1 polypeptide reduces the severity of corneal de-epithelialization. In some embodiments, administration of the modified FGF-1 polypeptide results in faster re-epithelialization of the cornea. In some embodiments, the modified FGF-1 polypeptide is administered over a period of up to two weeks or until complete regeneration of the corneal epithelium. In some embodiments, a first dose of the modified FGF-1 polypeptide is administered within 48 hours after exposure to the vesicant. In some embodiments, the chemical comprises chlorine gas, phosgene, an alkali, or an acid. In some embodiments, the vesicant comprises sulfur mustard (SM), nitrogen mustard (NM), lewisite, or half mustard (2-chloroethyl ethyl sulfide (CEES)). In some embodiments, wherein the vesicant is NM. In some embodiments, administration of the modified FGF-1 polypeptide suppresses NM induced up-regulation of ADAM17. In some embodiments, the chemical or vesicant induced injury is chemical burn. In some embodiments, the chemical burn is caused by chlorine gas, phosgene, an alkali, or an acid. In some embodiments, the modified FGF-1 polypeptide comprises mutations of positions 16, 66, and 117 of SEQ ID NO: 1. In some embodiments, the mutations are Cys16Ser, Ala66Cys, and Cys117Val. In some embodiments, the modified FGF-1 polypeptide is less susceptible to oxidation upon exposure to a vesicant. In some embodiments, the vesicant is NM. In some embodiments, the modified FGF-1 polypeptide comprises a sequence as set forth in any one of SEQ ID NOs: 2, and 9-206. In some embodiments, the modified FGF-1 polypeptide comprises a sequence as set forth in any one of SEQ ID NOs: 2, 9-204, and 207. In some embodiments, the modified FGF-1 polypeptide comprises a sequence as set forth in any one of SEQ ID NOs: 205 and 206. In some embodiments, the modified FGF-1 polypeptide comprises a sequence as set forth in SEQ ID NO: 2. In some embodiments, the modified FGF-1 polypeptide comprises a sequence as set forth in SEQ ID NO: 205. In some embodiments, the modified FGF-1 polypeptide comprises a sequence as set forth in SEQ ID NO: 206.

One embodiment provides a method of treating herpetic keratopathy comprising administering to a mammal a modified FGF-1 polypeptide comprising a sequence as set forth in any one of SEQ ID NOs: 205 and 206, or a pharmaceutical composition comprising the same. In some embodiments, the herpetic keratopathy is caused by a primary infection by herpes simplex virus. In some embodiments, the herpetic keratopathy is a chronic herpetic keratopathy. In some embodiments, the herpetic keratopathy is secondary to an infection by herpes simplex virus. In some embodiments, the herpetic keratopathy that is secondary to an infection by herpes simplex virus comprises neurotrophic keratopathy. In some embodiments, the modified FGF-1 polypeptide comprising a sequence as set forth in any one of SEQ ID Nos: 205 and 206, or a pharmaceutical composition comprising the same, is administered twice daily. In some embodiments, the modified FGF-1 polypeptide comprising a sequence as set forth in any one of SEQ ID Nos: 205 and 206, or a pharmaceutical composition comprising the same, is administered for a duration of 30 days. In some embodiments, administration of the modified FGF-1 polypeptide comprising a sequence as set forth in any one of SEQ ID Nos: 205 and 206, or a pharmaceutical composition comprising the same, results in healing of corneal ulcer, reduction of duration of pain and inflammation, reduction in pain and inflammation, reduction in corneal opacity, haze, scarring, or any combinations thereof. In some embodiments, the corneal ulcer comprises a herpetic corneal ulcer.

One embodiment provides a method of treating herpetic keratopathy comprising administering to a mammal a modified FGF-1 polypeptide comprising a sequence as set forth in any one of SEQ ID NOs: 2, 9-204, and 207 or a pharmaceutical composition comprising the same. In some embodiments, the herpetic keratopathy is caused by a primary infection by herpes simplex virus. In some embodiments, the herpetic keratopathy is a chronic herpetic keratopathy. In some embodiments, the herpetic keratopathy is secondary to an infection by herpes simplex virus. In some embodiments, the herpetic keratopathy that is secondary to an infection by herpes simplex virus comprises neurotrophic keratopathy. In some embodiments, the modified FGF-1 polypeptide comprising a sequence as set forth in any one of SEQ ID Nos: 2, 9-204, and 207 or a pharmaceutical composition comprising the same, is administered twice daily. In some embodiments, the modified FGF-1 polypeptide comprising a sequence as set forth in any one of SEQ ID Nos: 2, 9-204, and 207 or a pharmaceutical composition comprising the same, is administered for a duration of 30 days. In some embodiments, administration of the modified FGF-1 polypeptide comprising a sequence as set forth in any one of SEQ ID Nos: 2, 9-204, and 207 or a pharmaceutical composition comprising the same, results in healing of corneal ulcer, reduction of duration of pain and inflammation, reduction in pain and inflammation, reduction in corneal opacity, haze, scarring, or any combinations thereof. In some embodiments, the corneal ulcer comprises a herpetic corneal ulcer. In some embodiments, the mammal is a human.

INCORPORATION BY REFERENCE

All publications and patent applications mentioned in this specification are herein incorporated by reference in their entireties to the same extent as if each individual publication or patent application was specifically and individually indicated to be incorporated by reference.

BRIEF DESCRIPTION OF DRAWINGS

FIG. 6 shows an exemplary histopathological grading scheme for assessing the effects of vesicant induced corneal injury.

FIG. 10A shows a corneal section which was not exposed to NM, and FIG. 10B shows a comparison of exposed cornea with (lower panel) or without (upper panel) treatment with an exemplary polypeptide (TTHX1114).

DETAILED DESCRIPTION

Figure 1:
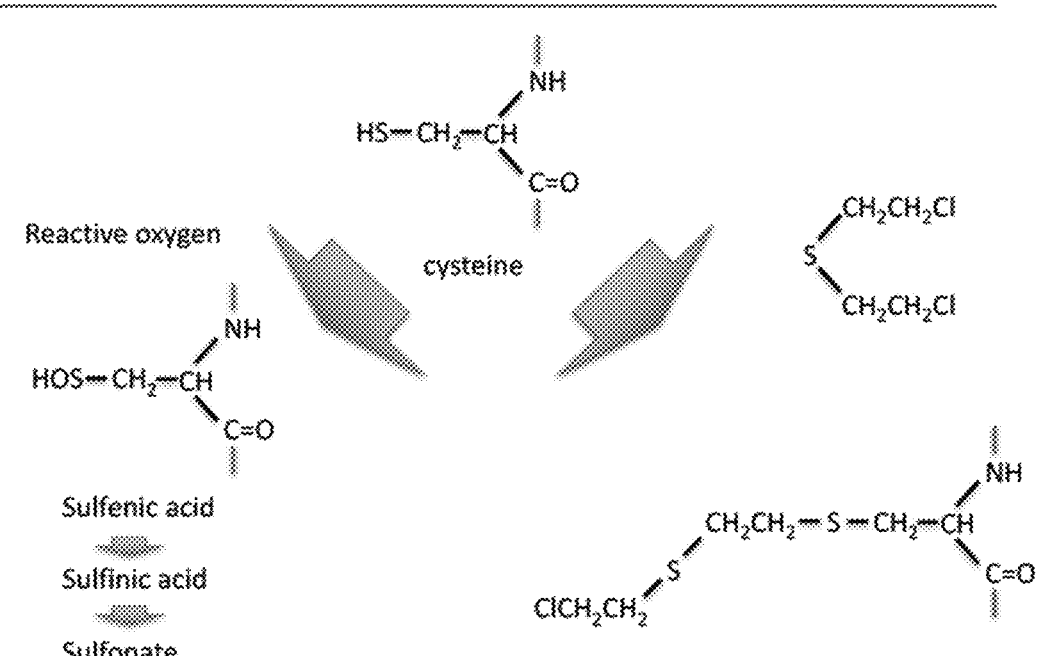
FIG. 1 illustrates the reaction of mustard gas with cysteine.

Diseases of and injuries to the eyes can be severely debilitating, and occur in a wide variety of forms. One class of ocular disease is mustard gas keratopathy. Mustard gas is a vesicant poisonous gas that was first released by the German Army on a battlefield at Ypres in April 1915 during World War I. Exposure to mustard gas can lead to long-term complications, which develop over the years. The cornea becomes scarred and irregular, and cholesterol and calcium are deposited in its tissues, resulting in progressive impairment of vision. Slit-lamp examination reveals that the episcleral tissues display a characteristic underglaze. White porcelain appearance and unusual vascular anomalies are common. These appear as enlarged, distorted vessels, sometimes with an ampulliform outline accompanied by varicosities and sausage-like vessels. With the passage of time, dense opacification of the cornea results, being most evident in the central and lower sections, as the upper portion has been protected by the overhanging eyelid. Predominant histopathological features of MGK include, for example, irregular epithelial thickness, degenerative changes, thickened epithelial basement membrane, keratocytes loss, and destroyed Bowman layer. (Kanavi et al., *Chronic and delayed mustard gas keratopathy: a histopathologic and immunohistochemical study*, Eur. J Ophthalmol. 2010 September-October; 20(5):839-43). Typically, within one day of corneal vesicant exposure, the corneal epithelium (CE) sloughs from the basement membrane (BM), corneal edema develops in the denuded stroma and full-thickness keratocytosis is apparent within the wound margins. By five days, an epithelial cap is regenerated and corneal edema begins to subside. One week after exposure, the CE is partially stratified, with rudimentary hemidesmosomal attachments. Despite this apparent improvement, corneas develop clinical signatures of chronic injury as soon as three weeks after exposure, including persistently elevated corneal edema, recurring corneal erosions and neovascularization. By eight weeks, the basement membrane zone undergoes severe degeneration. Further, MGK affected corneas appear to exhibit delayed wound healing process.

Provided herein are modified FGF-1 polypeptides, pharmaceutical compositions and medicaments that include such modified peptides, and methods of using such modified FGF-1 polypeptides to treat various conditions, such as ocular disease, disorders and conditions (e.g., Fuch's dystrophy), vesicant agent induced corneal epithelial and endothelial injuries (e.g., Mustard Gas Keratopathy (MGK)), wound healing, cardiovascular diseases (e.g., ischemia), and neurological conditions (e.g., amylotrophic lateral sclerosis (ALS)).

Also provided herein is a method of treating a chemical or vesicant induced injury by administering a modified fibroblast growth factors (FGF-1) polypeptides, or pharmaceutical composition or medicaments that include such modified peptides. In some embodiments, the method comprises treating mustard gas keratopathy (MGK), induced by a chemical injury, e.g., a chemical burn, by administering modified FGF-1 polypeptides described herein. In some embodiments, the method comprises treating mustard gas keratopathy (MGK), induced by a vesicant, e.g., nitrogen mustard (NM), by administering modified FGF-1 polypeptides described herein. In some embodiments, the method comprises treating a chemical or thermal injury caused by a chemical warfare agent, e.g., phosgene.

In some embodiments described herein, where the modified FGF-1 polypeptide is expressed with an N-terminal methionine (N-Met) residue, the polypeptide is subsequently purified without a step requiring proteolytic cleavage for removal of an N-terminal peptide. Accordingly, in some embodiments, the present disclosure provides a modified FGF-1 polypeptide that is prepared by a rapid purification method, without involving a proteolytic cleavage step for removal of an N-terminal peptide. This is particularly advantageous for production of the modified FGF-1 polypeptides per good manufacturing practice (GMP) guidelines. The advantages include the lack of a cleavage step, including eliminating the need for subsequent purification of the cleaved product and removal of the reagents used for cleavage. The further advantage of this is an increase in yield due to decreased handling and the alleviation of the need to test for residual cleavage reagents and contaminants introduced for the cleavage and subsequent separation of cleaved from uncleaved material.

The modified FGF-1 polypeptides described herein, can have increased stability (e.g. thermostability), reduced number of buried free thiols, and/or increased effective heparan sulfate proteoglycan (HSPG) affinity.

Several other advantages are associated with the use of the modified FGF-1 polypeptides in the methods described herein. For example, the modified FGF-1 polypeptides described herein can be administered without heparin in its pharmaceutical composition or formulation (e.g., an ophthalmic formulation), avoiding potential safety issues related to its biologic origin. In addition, avoidance of heparin allows the use of higher doses of the modified FGF-1 polypeptides without complications resulting from local heparin-induced adverse events or preexisting anti-heparin antibodies. Furthermore, in the absence of heparin, immediate binding of the modified FGF to tissue is maximized and systemic distribution is significantly reduced. The modified FGF-1 polypeptides described herein are also advantage of having enhanced local sequestration and reduced redistribution kinetics, thus increasing the elimination half-life and mean residence time (MRT) at the site of delivery, and allowing for a reduced dosing frequency. This can be the result of modified FGF-1 polypeptides described herein that have increased stability (e.g. thermostability), reduced number of buried free thiols, and/or increased effective heparan sulfate proteoglycan (HSPG) affinity.

The FGF-1 polypeptides of the present disclosure comprise, in various embodiments, modifications at the N-terminus of the polypeptide, such as an addition, a truncation, or a combination of additions and truncations. In some embodiments, the modification is the addition of a single N-terminal methionine residue. In some embodiments, the modification is the addition of an extension peptide. In some embodiments, the modification is a truncation of one or more of the first five residues of a FGF-1 polypeptide. In some embodiments, the FGF-1 polypeptides comprise a sequence as set forth in SEQ ID NO: 1, with one or more mutations, in addition to the N-terminal modification.

Several examples of the modified FGF-1 polypeptides disclosed herein comprise an N-terminal methionine (N-Met) residue in a mature form of the polypeptide. The retention of biological activity when amino acids are added to the N-terminus of a protein is unpredictable. Some proteins are tolerant of this and some are not, and the retention of biological activity and the potential for changes in stability are only determined empirically. The present disclosure identifies that the addition of N-terminal Met residues are tolerated with retention of biological activity and stability.

Certain Terminology

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described. Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

As used herein, the term "Percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer softwares such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

Definition of standard chemistry terms may be found in reference works, including but not limited to, Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

The terms "treat," "treating" or "treatment" include alleviating, abating or ameliorating a disease, disorder or condition symptoms, preventing additional symptoms, ameliorating or preventing the underlying metabolic causes of symptoms, inhibiting the disease, disorder, or condition, e.g., arresting the development of the disease, disorder or condition, relieving the disease, disorder or condition, causing regression of the disease, disorder or condition, relieving a condition caused by the disease, disorder or condition, or stopping the symptoms of the disease, disorder or condition. The terms "treat," "treating" or "treatment", include, but are not limited to, prophylactic and/or therapeutic treatments.

The term "acceptable" or "pharmaceutically acceptable", with respect to a formulation, composition or ingredient, refers to having no persistent detrimental effect on the general health of the subject being treated or does not abrogate the biological activity or properties of the modified FGF described herein, and is relatively nontoxic.

The term "amelioration" of the symptoms of a particular disease, disorder or condition by administration of a particular modified FGF or pharmaceutical composition refers to any lessening of severity, delay in onset, slowing of progression, or shortening of duration, whether permanent or temporary, lasting or transient that can be attributed to or associated with administration of the modified FGF or pharmaceutical composition.

The term "combination" or "pharmaceutical combination" as used herein, means a product that results from the mixing or combining of more than one active ingredient and includes both fixed and non-fixed combinations of the active ingredients. The term "fixed combination" means that one active ingredient (e.g., a modified FGF) and a co-agent are both administered to a patient simultaneously in the form of a single entity or dosage. The term "non-fixed combination" means that one active ingredient (e.g., a modified FGF) and a co-agent are administered to a patient as separate entities either simultaneously, concurrently or sequentially with no specific intervening time limits, wherein such administration provides effective levels of the two agents in the body of the patient. The latter also applies to cocktail therapy, e.g., the administration of three or more active ingredients.

The term "pharmaceutical composition" as used herein refers to one or more modified FGF-1 polypeptides with one or more other chemical components, such as carriers, stabilizers, diluents, dispersing agents, suspending agents, thickening agents, and/or excipients. The pharmaceutical composition facilitates administration of the modified FGF-1 polypeptides to an organism. Multiple techniques of administering a modified FGF-1 polypeptide exist in the art including, but not limited to: topical, ophthalmic, intraocular, periocular, intravenous, oral, aerosol, parenteral, and administration.

The term "carrier," as used herein, refers to relatively nontoxic chemical compounds or agents that facilitate the incorporation of an agent of interest (e.g., a modified FGF) into cells or tissues.

The term "diluent" refers to chemical compounds that are used to dilute the agent of interest (e.g., a modified FGF) prior to delivery. Diluents can also be used to stabilize agents because they can provide a more stable environment. Salts dissolved in buffered solutions (which also can provide pH control or maintenance) are utilized as diluents in the art, including, but not limited to a phosphate buffered saline solution.

The terms "co-administration" or the like, are meant to encompass administration of the selected agents (e.g., a modified FGF or composition thereof and a co-agent) to a single patient, and are intended to include treatment regimens in which the agents are administered by the same or different route of administration or at the same or different time.

The terms "effective amount" or "therapeutically effective amount," refer to a sufficient amount of a modified FGF-1 polypeptide, agent, combination or pharmaceutical composition described herein administered which will relieve to some extent one or more of the symptoms of the disease, disorder or condition being treated. The result can be reduction and/or alleviation of the signs, symptoms, or causes of a disease, or any other desired alteration of a biological system. For example, an "effective amount" for therapeutic uses is the amount of the modified FGF, agent, combination or pharmaceutical composition required to provide a desired pharmacologic effect, therapeutic improvement, or clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. It is understood that "an effect amount" can vary from subject to subject due to variation in metabolism of the modified FGF, combination, or pharmaceutical composition, age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The term "prophylactically effective amount," refers that amount of a modified FGF, compound, agent, combination or pharmaceutical composition described herein applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The term "subject" or "patient" as used herein, refers to an animal, which is the object of treatment, observation or experiment. By way of example only, a subject may be, but is not limited to, a mammal including, but not limited to, a human.

The terms "enhance" or "enhancing" means to increase or prolong either in potency or duration a desired effect. By way of example, "enhancing" the effect of therapeutic agents singly or in combination refers to the ability to increase or prolong, either in potency, duration and/or magnitude, the effect of the agents on the treatment of a disease, disorder or condition. When used in a patient, amounts effective for this use will depend on the severity and course of the disease, disorder or condition, previous therapy, the patient's health status and response to the drugs, and the judgment of the treating physician.

The term "modulate," means to interact with a target (e.g., a FGF receptor) either directly or indirectly so as to alter the activity of the target, including, by way of example only, to enhance the activity of the target, to inhibit or antagonize the activity of the target, to limit the activity of the target, or to extend the activity of the target. In some embodiments, modified FGF-1 polypeptides and pharmaceutical compositions described herein can modulate the activity of one or more respective targets (e.g., one or more FGF receptors). In some embodiments, the modified FGF-1 polypeptides described herein modulate (e.g., increase) the activity of one or more FGF receptors on a cell (e.g., a corneal endothelial cell), resulting, e.g., in cell migration and/or cell proliferation.

As used herein, the term "target" or refers to a biological molecule (e.g., a target protein or protein complex), such as an FGF receptor, or a portion of a biological molecule capable of being bound by a selective binding agent (e.g., a modified FGF) or pharmaceutical composition described herein. As used herein, the term "non-target" refers to a biological molecule or a portion of a biological molecule that is not selectively bound by a selective binding agent or pharmaceutical composition described herein.

The term "target activity" or "cell response" refers to a biological activity capable of being modulated by a modified FGF or any cellular response that results from the binding of a modified FGF to a FGF receptor. Certain exemplary target activities and cell responses include, but are not limited to, binding affinity, signal transduction, gene expression, cell migration, cell proliferation, cell differentiation, and amelioration of one or more symptoms associated with an ocular disease, disorder or condition.

The terms "herpetic keratitis", "herpes simplex keratitis", "HSK", "herpetic keratopathy", "herpes corneae", and "herpetic keratoconjunctivitis" refer to an ocular disease, disorder, or condition that is typically caused by herpes simplex virus (HSV).

Expressed and Mature Forms of the Modified FGF-1 Polypeptides

FGFs stimulate a family seven FGF receptor isoforms, and each FGF stimulates a different pattern of receptors to achieve its specific effect. See, e.g., Ornitz et al. (1996) The Journal of biological chemistry, 1996, 271(25):15292-7; Zhang et al. (2006) The Journal of biological chemistry, 2006, 281(23):15694-700). In some embodiments, modified FGF-1 polypeptide is preferable because it binds to and stimulates all seven FGF receptor isoforms. See Ornitz et al. (1996) The Journal of biological chemistry, 1996, 271(25): 15292-7.

Embodiments disclosed herein relate to a modified FGF-1 polypeptide or a pharmaceutical composition (e.g., an ophthalmic formulation) comprising a modified FGF-1 polypeptide. Embodiments disclosed herein also relate to a method of treating a chemical or a vesicant injury by administering a modified FGF-1 polypeptide or a pharmaceutical composition (e.g., an ophthalmic formulation) comprising a modified FGF-1 polypeptide. A modified FGF-polypeptide, as used herein, refers to a recombinant FGF that includes a substitution or mutation of one or more different amino acid residues and/or one or more deletions of one or more amino acid residues and/or one or more additions of one or more amino acid residues of SEQ ID NO: 1.

Provided herein, in a first embodiment, is a modified FGF-1 polypeptide comprising the sequence set forth as SEQ ID NO: 1, with one or more mutations, wherein the modified polypeptide further comprises a methionine residue upstream to the first residue of SEQ ID NO: 1. In some embodiments, the modified FGF-1 polypeptide comprising the N-terminal methionine (N-Met) residue is a mature form of the polypeptide. In some instances, the modified FGF-1 polypeptide, according to the first embodiment, comprises one or more mutations at positions 12, 16, 66, 117, and 134 of SEQ ID NO: 1. In some embodiments, the modified FGF-1 polypeptide is expressed in a host cell with a methionine residue upstream to the first residue of SEQ ID NO: 1. In some embodiments, the modified FGF-1 polypeptide is not subject to N-terminal processing for removal of the N-Met residue during maturation. Thus, in some embodiments, the mature form of a modified FGF-1 comprises an N-Met residue and one or more mutations at positions 12, 16, 66, 117, and 134 of SEQ ID NO: 1. An exemplary modified FGF-1 sequence, comprising an N-Met residue, is disclosed as SEQ ID NO: 2.

The present disclosure identifies that a modified FGF-1 as described herein, comprising an N-Met residue in its mature form, has similar biological activity as a version without the N-Met residue. N-terminal methionine removal, or excision, is a co-translational process that occurs as soon as a polypeptide emerges from the ribosome. The removal of the N-terminal methionine involves the substrate specificities of a cleavage enzyme, methionine aminopeptidase (metAP), which recognizes a methionine residue which is followed by an amino acid residue with a small side chain, such as alanine, glycine, proline, serine, threonine, or valine. Due to this substrate sequence specificity, the modified FGF-1 of the first embodiment, which comprises an N-Met residue followed by phenylalanine, see position 1 of SEQ ID NO: 1, is not processed by metAP. Thus, by expressing the modified FGF-1 with a methionine residue directly upstream of SEQ ID NO: 1, a mature modified FGF-1, comprising methionine as its N-terminal residue, can be obtained. In some embodiments, the modified FGF-1 according to the first embodiment is not expressed with an N-terminal peptide and therefore is not subject to proteolytic cleavage for removal of the same, during subsequent purification.

Provided herein, in a second embodiment, is a modified FGF-1 polypeptide comprising the sequence set forth as SEQ ID NO: 1, with one or more mutations, wherein the modified polypeptide further comprises a methionine residue upstream to the first residue of SEQ ID NO: 1, and one or more amino acids of the peptide set forth as SEQ ID NO: 3. A peptide comprising one or more residues of SEQ ID NO: 3 is herein referred to as an "extension peptide." Thus, the modified FGF-1 according to the second embodiment comprises the sequence set forth as SEQ ID NO: 1, with one or more mutations, a methionine residue upstream to the first residue of SEQ ID NO: 1, and an extension peptide positioned between the methionine residue and the first residue of SEQ ID NO: 1. In some embodiments, the modified FGF-1 polypeptide comprising the N-terminal methionine and an extension peptide, positioned between the methionine residue and the first residue of SEQ ID NO: 1, is a mature form of the polypeptide. In some embodiments, the modified FGF-1 polypeptide comprises one or more mutations at positions 12, 16, 66, 117, and 134 of SEQ ID NO: 1, which polypeptide is expressed in a host cell with a methionine residue upstream to the first residue of SEQ ID NO: 1, and further an extension peptide positioned between the methionine residue and the first residue of SEQ ID NO: 1. In some embodiments, the modified FGF-1 polypeptide according to the second embodiment is expressed with an extension peptide comprising five residues of SEQ ID NO: 3, positioned between the methionine residue and the first residue of SEQ ID NO: 1. In some embodiments, the modified FGF-1 polypeptide according to the second embodiment is expressed with four residues of SEQ ID NO: 3, positioned between the methionine residue and the first residue of SEQ ID NO: 1. In some embodiments, the modified FGF-1 polypeptide according to the second embodiment is expressed with three residues of SEQ ID NO: 3, positioned between the methionine residue and the first residue of SEQ ID NO: 1. In some embodiments, the modified FGF-1 polypeptide according to the second embodiment is expressed with two residues of SEQ ID NO: 3, positioned between the methionine residue and the first residue of SEQ ID NO: 1. In some embodiments, the modified FGF-1 polypeptide according to the second embodiment is expressed with one residue of SEQ ID NO: 3, positioned between the methionine residue and the first residue of SEQ ID NO: 1. Exemplary sequences of the extension peptide include SEQ ID NOS: 4-5 and any one of the sequences of TEK, EK, or K.

In some instances, the modified FGF-1 polypeptide of the second embodiment, comprising an extension peptide and an N-terminal methionine residue, is not subject to N-terminal processing for removal of the methionine residue, whereas in some instances the methionine is excised by a cleavage enzyme. Typically, the cleavage enzyme is methionine aminopeptidase (metAP). Thus, in some examples, the mature form of the modified FGF-1 polypeptide according to the second embodiment comprises an N-Met residue followed by an extension peptide as described herein. Exemplary sequences of mature forms of modified FGF-1 polypeptides according to the second embodiment, comprising an N-terminal methionine, and one or more residues of the extension peptide, positioned between the methionine residue and the first residue of SEQ ID NO:1, are set forth as SEQ ID NOS: 9-13, wherein the sequences further comprise one or more mutations at amino acids corresponding to positions 12, 16, 66, 117, and 134 of SEQ ID NO: 1. Additional exemplar sequences of mature modified FGF-1 polypeptides comprising an N-terminal methionine, and an extension peptide are set forth as SEQ ID NOS: 14-18. In some other examples, the mature form of the modified FGF-1 polypeptide according to the second embodiment does not comprise an N-Met residue but includes only an extension peptide. Exemplary sequences of mature forms of modified FGF-1 polypeptides according to the second embodiment, comprising an extension peptide, positioned upstream to the first residue of SEQ ID NO:1 are set forth as SEQ ID NOS: 19-23, wherein the sequences further comprise one or more mutations at amino acids corresponding to positions 12, 16, 66, 117, and 134 of SEQ ID NO: 1. Additional exemplar sequences of mature modified FGF-1 polypeptides comprising one or more residues of the extension peptide are set forth as SEQ ID NOS: 24-28. In some embodiments, the methionine residue is cleaved by metAP when the extension peptide starts with an alanine (as in SEQ ID NO: 4) or with a threonine (as in SEQ ID NO: 5). In those instance, the mature FGF-1 polypeptide does not comprise an N-terminal methionine residue, e.g., SEQ ID NOS: 19, 21, 24, and 26.

Provided herein, in a third embodiment, is a modified FGF-1 polypeptide comprising the sequence set forth as SEQ ID NO: 1, with one or more mutations, wherein the modified polypeptide further comprises an extension peptide positioned upstream to the first residue of SEQ ID NO: 1. In some embodiments, the modified FGF-1 polypeptide comprising an extension peptide is a mature form of the polypeptide. In some embodiments, the modified FGF-1 polypeptide comprising one or more mutations at positions 12, 16, 66, 117, and 134 of SEQ ID NO: 1, which polypeptide is expressed in a host cell with one or more amino acid residues of the extension peptide positioned upstream to the first residue of SEQ ID NO: 1. Exemplary sequences of the modified FGF-1 polypeptides comprising an extension peptide, expressed without an N-terminal methionine residue, are set forth as SEQ ID NOS: 19-23, wherein the sequences further comprise one or more mutations at amino acids corresponding to positions 12, 16, 66, 117, and 134 of SEQ ID NO: 1. Additional exemplar sequences of mature modified FGF-1 polypeptides comprising one or more residues of the extension peptide, and expressed without an N-terminal methionine residue, are set forth as SEQ ID NOS: 24-28.

Provided herein, in a fourth embodiment, is a modified FGF-1 polypeptide comprising the sequence set forth as SEQ ID NO: 1, with one or more mutations, wherein the modified polypeptide further comprises a truncation of one or more of the first five residues of SEQ ID NO: 1. In some embodiments, the modified FGF-1 polypeptide comprising the truncation of one or more of the first five residues of SEQ ID NO: 1 is the mature form of the polypeptide. In some embodiments, the modified FGF-1 polypeptide comprises one or more mutations at positions 12, 16, 66, 117, and 134 of SEQ ID NO: 1, wherein one or more of the first five residues of SEQ ID NO: 1 is deleted. In some cases, the modified FGF-1 polypeptide comprising truncations is expressed with an N-terminal methionine residue. For instance, the modified FGF-1 polypeptide, according to the fourth embodiment, can have a sequence wherein the N-Met residue is followed by the second residue, asparagine, of SEQ ID NO: 1. In some cases, the modified FGF-1 polypeptide comprises an N-Met residue followed by the third residue, leucine, of SEQ ID NO: 1. In some cases, the modified FGF-1 polypeptide comprises an N-Met residue followed by the fourth residue, proline, of SEQ ID NO: 1. In some cases, the modified FGF-1 polypeptide comprises an N-Met residue followed by the fifth residue, proline, of SEQ ID NO: 1. An extension peptide can be positioned in between the N-Met residue and the first, second, third, fourth, or fifth residue of SEQ ID NO: 1. Examples of a mature form of the modified FGF-1 polypeptide according to the fourth embodiment wherein an N-Met residue is followed by the second, third, fourth, or fifth residue of SEQ ID NO: 1 are shown in SEQ ID NOS: 37-40, wherein the sequences further comprise one or more mutations at amino acids corresponding to positions 12, 16, 66, 117, and 134 of SEQ ID NO: 1. Additional examples of modified FGF-1 polypeptides comprising truncations and an N-Met residue, are provided in SEQ ID NOS: 41-44.

The present disclosure also relates to modified FGF-1 polypeptides comprising one or more mutations of SEQ ID NO: 1, wherein the polypeptides are expressed with an N-Met residue followed by an extension peptide, and the extension peptide is followed by truncation of one or more of the first five residues of SEQ ID NO: 1. In some embodiments, the modified FGF-1 polypeptide comprises one or more mutations at positions 12, 16, 66, 117, and 134 of SEQ ID NO: 1, wherein the polypeptide is expressed with an N-Met residue followed by an extension peptide, and the extension peptide is followed by truncation of one or more of the first five residues of SEQ ID NO: 1. Examples of such sequences expressed with an N-Met residue followed by an extension peptide, which extension peptide is followed by truncation of one or more of the first five residues of SEQ ID NO: 1 are disclosed as SEQ ID NOS: 45-68, wherein the sequences further comprise one or more mutations at amino acids corresponding to positions 12, 16, 66, 117, and 134 of SEQ ID NO: 1. In some examples, the N-terminal methionine is cleaved off by N-terminal processing and accordingly the mature form of the modified FGF-1 polypeptide comprises only one or more residues of the leader fragment followed by truncation of one or more of the first five residues of SEQ ID NO: 1, as exemplified in SEQ ID NOS: 69-92, wherein the exemplary sequences further comprise one or more mutations at amino acids corresponding to positions 12, 16, 66, 117, and 134 of SEQ ID NO: 1. Additional examples of sequences without N-Met residue but including an extension peptide and truncations of N-terminal residues, are provided in SEQ ID NO: 93-117.

In some examples, the N-Met residue is retained in the mature modified FGF-1 polypeptide sequence, and accordingly the mature forms comprise sequences as exemplified in SEQ ID NO: 45-68, further comprising one or more mutations at amino acids corresponding to positions 12, 16, 66, 117, and 134 of SEQ ID NO: 1. Additional examples of sequences comprising an N-Met residue, an extension peptide and truncations of N-terminal residues, are provided in SEQ ID NO: 118-141 and 207.

The truncated versions of the modified FGF-1 polypeptides comprising one or more mutations at positions 12, 16, 66, 117, and 134 of SEQ ID NO: 1, are, in a fifth embodiment, expressed without an N-terminal methionine residue, and further without an extension peptide. In some examples, mature modified FGF-1 polypeptides according to the fifth embodiment comprise a sequence as set forth in SEQ ID NOS: 29-32, wherein the sequences further comprise one or more mutations at amino acids corresponding to positions 12, 16, 66, 117, and 134 of SEQ ID NO: 1. In some examples, the modified FGF-1 polypeptides according to the fifth embodiment comprise a sequence selected from the group consisting of SEQ ID NOS: 33-36.

In instances where the modified FGF-1 polypeptide, or its truncated version, comprising one or more mutations at positions 12, 16, 66, 117, and 134 of SEQ ID NO: 1, is expressed with an N-terminal methionine followed by an extension peptide, the methionine residue is either retained or cleaved off of the N-terminus during maturation of the polypeptide after expression. In some examples, where the modified FGF-1 polypeptide is expressed with an alanine next to the N-Met residue, e.g., SEQ ID NO: 14, the methionine is cleaved, to yield a mature FGF-1 polypeptide that does not comprise an N-Met residue, e.g., SEQ ID NO: 19. In some examples, where the modified FGF-1 polypeptide is expressed with a threonine next to the N-Met residue, e.g., SEQ ID NO: 16, the methionine is cleaved, to yield a mature FGF-1 polypeptide that does not comprise an N-Met residue, e.g., SEQ ID NO: 20. In some examples, where the modified FGF-1 polypeptide is expressed with a glutamic acid next to the N-Met residue, e.g., SEQ ID NO: 17, the methionine is not cleaved, to yield a mature FGF-1 that comprise an N-terminal methionine and has the same sequence as the expressed form.

Provided herein, in a sixth embodiment, is a modified FGF-1 polypeptide comprising the sequence set forth as SEQ ID NO: 1, comprising a mutation at position 67. In some embodiments, the modified FGF-1 polypeptide comprises a mutation at position 67 of SEQ ID NO: 1, one or more further mutations at positions 12, 16, 66, 117, and 134, and is expressed with an N-Met residue. The internal methionine at position 67 can be replaced, for example, with an alanine residue. In absence of the internal methionine at position 67, the N-terminal methionine of the modified FGF-1 polypeptide can be cleaved, post-expression; using cyanogen bromide (CNBr), an agent that specifically cleaves the amide bond after methionine residues. In some cases, the modified FGF-1 polypeptides according to the sixth embodiment are expressed with an extension peptide. In some other cases, modified FGF-1 polypeptides according to the sixth embodiment are expressed in a form comprising truncations of one or more of the first five residues of SEQ ID NO: 1, as exemplified in SEQ ID NOS: 142-149, wherein the sequences further comprise one or more mutations at amino acids corresponding to positions 12, 16, 66, 117, and 134 of SEQ ID NO: 1. In yet other examples, the modified FGF-1 polypeptides according to the sixth embodiment are expressed in a form comprising an extension peptide and truncations of one or more of the first five residues of SEQ ID NO: 1, as exemplified in SEQ ID NOS: 151-175. Additional examples of the modified FGF-1 polypeptides according to the sixth embodiment, in their mature forms, are set forth in SEQ ID NOS: 174-204. Among the modified FGF-1 polypeptides expressed in a form that comprises an internal methionine mutation, in cases where the polypeptide is expressed with an N-terminal methionine followed by an alanine or a threonine residue from the extension peptide, e.g., SEQ ID NO: 175 and SEQ ID NO: 177, respectively, the N-terminal methionine can be cleaved off during maturation of the polypeptide either by metAP or using CNBr.

Provided herein, in a seventh embodiment, is a modified FGF-1 polypeptide comprising the sequence set forth as SEQ ID NO: 205, for use in a method as described herein. Provided herein, in an eighth embodiment, is a modified FGF-1 polypeptide comprising the sequence set forth as SEQ ID NO: 206, for use in a method as described herein.

The present disclosure further relates to modified FGF-1 polypeptides comprising any combination of deletion, insertion, and substitution of SEQ ID NO: 1, provided that said modified polypeptide comprises one or more mutations of SEQ ID NO: 1. Amino acid substitutions may be introduced into a modified FGF-1 polypeptide and the products screened for a desired activity, e.g., retained/improved effectivity in treating ocular disorders, increased potency in amelioration of Fuch's dystrophy, improved treatment of mustard gas keratopathy. Amino acid substitutions may also be introduced into a modified FGF-1 polypeptide and the products screened for a desired physicochemical property, e.g., less prone to aggregation, improved solubility, prolonged half-life, ease of formulating as an ophthalmic pharmaceutical, enhanced stability, improved shelf-life. Both conservative and non-conservative amino acid substitutions are contemplated.

The modified FGF-1 polypeptide, as in any of the above embodiments, is expressed in a form that comprises at least 136 amino acids. In some embodiments, the modified FGF-1 polypeptide is expressed in a form that comprises 137 amino acids. In some embodiments, the modified FGF-1 polypeptide is expressed in a form that comprises 138 amino acids. In some embodiments, the modified FGF-1 polypeptide is expressed in a form that comprises 139 amino acids. In some embodiments, the modified FGF-1 polypeptide is expressed in a form that comprises 140 amino acids. In some embodiments, the modified FGF-1 polypeptide is expressed in a form that comprises 141 amino acids. In some embodiments, the modified FGF-1 polypeptide is expressed in a form that comprises 142 amino acids. In some embodiments, the modified FGF-1 polypeptide is expressed in a form that comprises 143 amino acids. In some embodiments, the modified FGF-1 polypeptide is expressed in a form that comprises 144 amino acids. In some embodiments, the modified FGF-1 polypeptide is expressed in a form that comprises 145 amino acids. In some embodiments, the modified FGF-1 polypeptide is expressed in a form that comprises 146 amino acids.

The modified FGF-1 polypeptide, as in any of the above embodiments, comprises at least 136 amino acids in the mature form. In some examples, the modified FGF-1 polypeptide comprises 137 amino acids in the mature form. In some examples, the modified FGF-1 polypeptide comprises 138 amino acids in the mature form. In some examples, the modified FGF-1 polypeptide comprises 139 amino acids in the mature form. In some examples, the modified FGF-1 polypeptide comprises 140 amino acids in the mature form. In some examples, the modified FGF-1 polypeptide comprises 141 amino acids in the mature form. In some examples, the modified FGF-1 polypeptide comprises 142 amino acids in the mature form. In some examples, the modified FGF-1 polypeptide comprises 143 amino acids in the mature form. In some examples, the modified FGF-1 polypeptide comprises 144 amino acids in the mature form. In some examples, the modified FGF-1 polypeptide comprises 145 amino acids in the mature form. In some examples, the modified FGF-1 polypeptide comprises 146 amino acids in the mature form.

In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1, provided that said polypeptide comprises an N-Met residue in the mature form of the polypeptide. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 9-13, provided that said polypeptide comprises the N-Met residue in its mature form, and the polypeptide comprises one or more mutations at amino acid positions corresponding to positions 12, 16, 66, 117, and 134 of SEQ ID NO: 1. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 14-18, provided that said polypeptide comprises the N-Met residue in its mature form. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 19-23, provided that said polypeptide does not comprise the N-Met residue in its mature form, and the polypeptide comprises one or more mutations at amino acid positions corresponding to positions 12, 16, 66, 117, and 134 of SEQ ID NO: 1. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 24-28, provided that said polypeptide does not comprise an N-Met residue in its mature form. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 19-23, provided that said polypeptide does not comprise an N-Met residue in its mature form, and the polypeptide comprises one or more mutations at amino acid positions corresponding to positions 12, 16, 66, 117, and 134 of SEQ ID NO: 1. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 37-40, provided that said polypeptide comprises an N-Met residue in its mature form, and the polypeptide comprises one or more mutations at amino acid positions corresponding to positions 12, 16, 66, 117, and 134 of SEQ ID NO: 1. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 41-44, provided that said polypeptide comprises an N-Met residue in its mature form. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 45-68, provided that said polypeptide comprises one or more mutations at amino acid positions corresponding to positions 12, 16, 66, 117, and 134 of SEQ ID NO: 1, and said polypeptide does not comprise an N-Met residue in its mature form. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 69-92, comprises one or more mutations at amino acid positions corresponding to positions 12, 16, 66, 117, and 134 of SEQ ID NO: 1, and said polypeptide comprises an N-Met residue in its mature form. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 93-117, provided that said polypeptide does not comprise an N-Met residue in its mature form. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 118-141 and 207, provided that said polypeptide comprises an N-Met residue in its mature form. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NOS: 29-32, provided that said polypeptide comprises one or more mutations at amino acid positions corresponding to positions 12, 16, 66, 117, and 134 of SEQ ID NO: 1. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NOS: 33-36.

In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NOS: 142-204.

In some embodiments, the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at position 12 with, for example, the mutation Lys12Val, and wherein said modified FGF-1 polypeptide comprises an N-terminal methionine in its mature form. In some embodiments, the modified FGF-1 polypeptide comprises a sequence with a mutation at position 12 of SEQ ID NO: 1, for example the mutation Lys12Val, and with truncation of one or more of the first five residue of SEQ ID NO: 1, wherein said modified FGF-1 polypeptide comprises an N-Met residue in its mature form. In some embodiments, the modified FGF-1 polypeptide comprises a sequence with a mutation at position 12 of SEQ ID NO: 1, for example the mutation Lys12Val, with an extension peptide, and with truncation of one or more of the first five residue of SEQ ID NO: 1, wherein said modified FGF-1 polypeptide comprises an N-met residue in its mature form. In some embodiments, the modified FGF-1 polypeptide comprises a sequence with mutations at position 12 of SEQ ID NO: 1, for example the mutation Lys12Val, wherein the polypeptide further comprises a mutation of the methionine at position 67 of SEQ ID NO: 1, and is expressed with a methionine at the N-terminus, which methionine is cleaved off of the polypeptide in its mature form.

In some embodiments, the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at position 16 with, for example, the mutation Cys16Ser, and wherein said modified FGF-1 polypeptide comprises an N-met residue in its mature form. In some embodiments, the modified FGF-1 polypeptide comprises a sequence with a mutation at position 16 of SEQ ID NO: 1, for example the mutation Cys16Ser, and with truncation of one or more of the first five residue of SEQ ID NO: 1, wherein said modified FGF-1 polypeptide comprises an N-met residue in its mature form. In some embodiments, the modified FGF-1 polypeptide comprises a sequence with a mutation at position 16 of SEQ ID NO: 16, for example the mutation Cys16Ser, with an extension peptide, and with truncation of one or more of the first five residue of SEQ ID NO: 1, wherein said modified FGF-1 polypeptide comprises an N-met residue. In some embodiments, the modified FGF-1 polypeptide comprises a sequence with mutations at position 16 of SEQ ID NO: 1, for example the mutation Cys16Ser, wherein the polypeptide further comprises a mutation of the methionine at position 67 of SEQ ID NO: 1, and is expressed with a methionine at the N-terminus, which methionine is cleaved off of the polypeptide in its mature form.

In some embodiments, the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at position 66 with, for example, the mutation Ala66Cys, and wherein said modified FGF-1 polypeptide comprises an N-terminal methionine in its mature form. In some embodiments, the modified FGF-1 polypeptide comprises a sequence with a mutation at position 66 of SEQ ID NO: 1, for example the mutation Ala66Cys, and with truncation of one or more of the first five residue of SEQ ID NO: 1, wherein said modified FGF-1 polypeptide comprises an N-met residue in its mature form. In some embodiments, the modified FGF-1 polypeptide comprises a sequence with a mutation at position 66 of SEQ ID NO: 1, for example the mutation Ala66Cys, with an extension peptide, and with truncation of one or more of the first five residue of SEQ ID NO: 1, wherein said modified FGF-1 polypeptide is expressed with an N-Met residue. In some embodiments, the modified FGF-1 polypeptide comprises a sequence with mutations at position 66 of SEQ ID NO: 1, for example the mutation Ala66Cys, wherein the polypeptide further comprises a mutation of the methionine at position 67 of SEQ ID NO: 1, and is expressed with a methionine at the N-terminus, which methionine is cleaved off of the polypeptide in its mature form.

In some embodiments, the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at position 117 with, for example, the mutation Cys117Val, and wherein said modified FGF-1 polypeptide comprises an N-met residue in its mature form. In some embodiments, the modified FGF-1 polypeptide comprises a sequence with a mutation at position 117 of SEQ ID NO: 1, for example the mutation Cys117Val, and with truncation of one or more of the first five residue of SEQ ID NO: 1, wherein said modified FGF-1 polypeptide comprises an N-met residue in its mature form. In some embodiments, the modified FGF-1 polypeptide comprises a sequence with a mutation at position 117 of SEQ ID NO: 1, for example the mutation Cys117Val, with an extension peptide, and with truncation of one or more of the first five residue of SEQ ID NO: 1, wherein said modified FGF-1 polypeptide comprises an N-met residue in its mature form.

In some embodiments, the modified FGF-1 polypeptide comprises a sequence with mutations at position 117 of SEQ ID NO: 1, for example the mutation Cys117Val, wherein the polypeptide further comprises a mutation of the methionine at position 67 of SEQ ID NO: 1, and is expressed with a methionine at the N-terminus, which methionine is cleaved off of the polypeptide in its mature form.

In some embodiments, the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at position 134 with, for example, the mutation Pro134Val, and wherein said modified FGF-1 polypeptide comprises an N-terminal methionine in its mature form. In some embodiments, the modified FGF-1 polypeptide comprises a sequence with a mutation at position 134 of SEQ ID NO: 1, for example the mutation Pro134Val, and with truncation of one or more of the first five residue of SEQ ID NO: 1, wherein said modified FGF-1 polypeptide comprises an N-met residue in its mature form. In some embodiments, the modified FGF-1 polypeptide comprises a sequence with a mutation at position 134 of SEQ ID NO: 1, for example the mutation Pro134Val, with an extension peptide, and with truncation of one or more of the first five residue of SEQ ID NO: 1, wherein said modified FGF-1 polypeptide comprises an N-met residue in its mature form. In some embodiments, the modified FGF-1 polypeptide comprises a sequence with mutations at position 134 of SEQ ID NO: 1, for example the mutation Pro134Val, wherein the polypeptide further comprises a mutation of the methionine at position 67 of SEQ ID NO: 1, and is expressed with a methionine at the N-terminus, which methionine is cleaved off of the polypeptide in its mature form.

In some embodiments, the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at positions 16, 66, and 117 of SEQ ID NO: 1, with, for example, the mutation Cys16Ser, Ala66Cys, and Cys117Val, and wherein said modified FGF-1 polypeptide comprises an N-met residue in its mature form. In some embodiments, the modified FGF-1 polypeptide comprises a sequence with mutations at positions 16, 66, and 117 of SEQ ID NO: 1, with, for example, the mutation Cys16Ser, Ala66Cys, and Cys117Val, and with truncation of one or more of the first five residue of SEQ ID NO: 1, wherein said modified FGF-1 polypeptide comprises an N-met residue in its mature form. In some embodiments, the modified FGF-1 polypeptide comprises a sequence with mutations at positions 16, 66, and 117 of SEQ ID NO: 1, with, for example, the mutation Cys16Ser, Ala66Cys, and Cys117Val, with an extension peptide, and with truncation of one or more of the first five residue of SEQ ID NO: 1, wherein said modified FGF-1 polypeptide comprises an N-met residue. In some embodiments, the modified FGF-1 polypeptide comprises a sequence with mutations at positions 16, 66, and 117 of SEQ ID NO: 1, with, for example, the mutation Cys16Ser, Ala66Cys, and Cys117Val, wherein the polypeptide further comprises a mutation of the methionine at position 67 of SEQ ID NO: 1, and is expressed with a methionine at the N-terminus, which methionine is cleaved off of the polypeptide in its mature form.

In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to a sequence selected from SEQ ID NOs: 2, 9-204, and 207. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 205 or 206.

In some embodiments, the modified FGF-1 polypeptide is thermostable. As used herein, a thermostable FGF (e.g., a thermostable FGF-1) refers to an FGF having a modified amino acid sequence relative to SEQ ID NO: 1 that is also more stable than the polypeptide of SEQ ID NO: 1 under the same conditions. Examples of mutations capable of conferring thermostability to FGF (e.g., FGF-1) and methods for assessing thermostability are described, for example, in U.S. Pat. Nos. 7,790,682; 7,595,296; 7,696,171; 7,776,825; 7,659,379; 8,119,776; 8,153,770; 8,153,771; and 8,461,111; U.S. Patent Application Publication Nos. 2011/0224404 and 2013/0130983; and in Xia et al. *PloS one.* (2012) 7(11): e48210. In some embodiments, positions 12 and/or 134 are mutated in FGF-1 to generate a modified FGF-1 that is thermostable.

In some embodiments, the modified FGF-1 polypeptide includes one or more modifications that reduce the number of reactive thiols (e.g., free cysteines). Examples such modifications in FGF-1 are described, for example, in U.S. Pat. Nos. 7,790,682; 7,595,296; 7,696,171; 7,776,825; 7,659,379; 8,119,776; 8,153,770; 8,153,771; and 8,461,111; U.S. Patent Application Publication Nos. 2011/0224404 and 2013/0130983; and in Xia et al. *PloS one.* (2012) 7(11): e48210. In some embodiments, positions 83 and/or 117 are mutated in SEQ ID NO: 1 to generate a modified FGF-1 that reduces the number of reactive thiols.

In some embodiments, the modified FGF includes one or more modifications that enable formation of an internal disulfide linkage. In some embodiments, position 66 is mutated in SEQ ID NO: 1 to generate a modified FGF-1 that comprises an internal disulfide linkage.

In some embodiments, the modified FGF-1 polypeptides described herein can be administered without exogenous heparin in the formulation for stability, they can be formulated and applied without heparin and thus are more able to bind to the tissue heparans. Such modified FGF-1 polypeptides have a high affinity for tissue heparans that are exposed in a surgical, traumatic or dystrophic conditions and disease-states and so bind to diseased tissue on application. In addition, the modified FGF-1 polypeptides being more thermally stable are suitable for formulation and storage at room temperature. The stability of the modified FGF-1 polypeptides also makes them suitable for administration in both solution (e.g., immediate release) and sustained-release formulations.

In some embodiments, the modified FGF-1 polypeptide is SEQ ID NO: 1 that has been modified at one or more of positions 12, 16, 66, 117, and 134. In some embodiments, the modified FGF is SEQ ID NO: 1 that has been modified at positions 16, 66, and 117. The amino acid positions can be substituted with, e.g., Ser, Cys, Val, or other amino acids to create disulfide linkages between modified amino acids and wild-type amino acids. In some embodiments, the modified FGF comprises the amino acid sequence of SEQ ID NO: 2, also referred to as N-Met THX1114. In some embodiments, the modified FGF-1 polypeptide comprises one or more mutations selected from the group consisting of: Lys12Val, Pro134Val, Ala66Cys, Cys117Val, and Pro134Val. In some embodiments, the modified FGF-1 polypeptide comprises the sequence of SEQ ID NO: 2.

In some embodiments, the modified FGF-1 polypeptides or compositions described herein may be prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug.

The modified FGF-1 polypeptides described herein may be labeled isotopically (e.g., with a radioisotope) or by other means, including, but not limited to, the use of chromophores or fluorescent moieties, bioluminescent labels, photoactivatable or chemiluminescent labels.

The present discloser further relates to modified FGF polypeptides comprising N-terminal modification(s), wherein the modified FGF polypeptide can be any member of the FGF family, including FGF-1 (SEQ ID NO: 1), FGF-2, FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, FGF-20, FGF-21, FGF-22, and FGF-23, and FGF-24.

In some embodiments, the synthesis of modified FGF-1 polypeptides as described herein is accomplished using means described in the art, using the methods described herein, or by a combination thereof.

In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at one or more positions 16, 66, and 117 with, for example, the mutations Cys16Ser, Ala66Cys, and Cys117Val. In some embodiments, the modified FGF comprises the wild-type human FGF-1 sequence with a mutation at positions 16, 66 and 117, for example the mutations Cys16Ser, Ala66Cys, and Cys117Val.

Recombinant Techniques for Preparation of Modified FGF-1 Polypeptides

A variety of host-expression vector systems may be utilized to produce the modified FGF-1 polypeptides provided herein. Such host-expression systems represent vehicles by which the modified FGF-1 polypeptides may be produced and subsequently purified, but also represent cells that may, when transformed or transfected with the appropriate nucleotide coding sequences, exhibit the modified gene product in situ. Examples of host-expression systems include but are not limited to, bacteria, insect, plant, mammalian, including human host systems, such as, but not limited to, insect cell systems infected with recombinant virus expression vectors (e.g., baculovirus) containing nucleotide sequences coding for the modified FGF-1 polypeptides; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing coding sequences for the modified FGF-1 polypeptides; or mammalian cell systems, including human cell systems, e.g., HT1080, COS, CHO, BHK, 293, 3T3, harboring recombinant expression constructs containing promoters derived from the genome of mammalian cells, e.g., metallothionein promoter, or from mammalian viruses, e.g., the adenovirus late promoter; the vaccinia virus 7.5K promoter, or from yeast-derived plasmids e.g., pSH19 and pSH15, or from bacteriophages such as lambda phase and derivatives thereof. Examples of bacterial expression systems include but are not limited to *Escherichia coli*-derived plasmids (e.g., pBR322, pBR325, pUC12, pUC13, and pET-3); *Bacillus subtilis*-derived plasmids (e.g., PUB110, pTP5, and pC194).

In some embodiments, a host cell strain is chosen such that it modulates the expression of the inserted sequences, or modifies and processes the gene product in the specific fashion desired. Such modifications and processing of protein products may be important for the function of the protein. Different host cells have specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells, including human host cells, include but are not limited to HT1080, CHO, VERO, BHK, HeLa, COS, MDCK, 293, 3T3, and WI38.

For long-term, high-yield production of recombinant peptides, stable expression is desired. For example, cell lines that stably express the recombinant modified FGF-1 polypeptides may be engineered. In some embodiments, rather than using expression vectors that contain viral origins of replication, host cells can be transformed with DNA controlled by appropriate expression control elements, e.g., promoter, enhancer, sequences, transcription terminators, polyadenylation sites, and the like, and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. In some examples, this method may advantageously be used to engineer cell lines that express the modified FGF-1 polypeptide product. Such engineered cell lines may be particularly useful in screening and evaluation of compounds that affect the biological of the gene product.

Disulfide Bond Formation in Modified FGF-1 Polypeptides

In some embodiments, the modified FGF-1 polypeptide of the present disclosure comprises the following mutations in SEQ ID NO: 1—Cys16Ser, Ala66Cys, and Cys117Val, wherein the polypeptide includes an internal disulfide bond between the cysteine residues at positions 66 and 83. For many recombinant proteins, the formation of correct disulfide bonds is vital for attaining their biologically active three-dimensional conformation. The formation of erroneous disulfide bonds can lead to protein misfolding and aggregation into inclusion bodies. In *E. coli*, cysteine oxidation typically takes places in the periplasm, where disulfide bonds are formed in disulfide exchange reactions catalyzed by a myriad of enzymes, mainly from the Dsb family (Rosano, G. L., & Ceccarelli, E. A. (2014). *Recombinant protein expression in Escherichia coli: advances and challenges*. Frontiers in Microbiology, 5, 172). By contrast, disulfide bond formation in the cytoplasm is rare. This situation affects the production of recombinant proteins with disulfide bonds that are produced in the cytoplasm, such as a modified FGF-1 polypeptide comprising an internal disulfide linkage between Cys66 and Cys83. Accordingly, in some examples, an engineered *E. coli* strain that possess an oxidative cytoplasmic environment that favors disulfide bond formation is selected as a host cell for expression of the modified FGF-1 polypeptides (Rosano, G. L., & Ceccarelli, E. A. (2014). *Recombinant protein expression in Escherichia coli: advances and challenges*. Frontiers in Microbiology, 5, 172). Examples of such strains include but are not limited to Origami (Novagen), which has a trxB– gor– genotype in the K-12 background, and SHuffle® T7 Express strain (NEB), which has a trxB–gor– genotype in a BL21 (DE3) background and constitutively expresses a chromosomal copy of the disulfide bond isomerase DsbC. It has been shown that DsbC promotes the correction of mis-oxidized proteins into their correct form and is also a chaperone that can assist in the folding of proteins that do not require disulfide bonds. Without being bound by a particular theory, it is contemplated that due to the action of DsbC, less target protein, such as the modified FGF-1 polypeptide comprising an internal disulfide linkage between Cys66 and Cys83, aggregates into inclusion bodies. Thus, in certain embodiments, the present disclosure identifies an improved method for cytoplasmic production of a modified FGF-1 polypeptide comprising internal disulfide linkage between Cys16 and Cys83.

In some embodiments where the modified FGF-1 polypeptide is expressed with an N-Met residue, the polypeptide is subsequently purified without a step requiring proteolytic cleavage for removal of an N-terminal peptide. Accordingly, in some embodiments, the present disclosure provides a method of rapid purification of the modified FGF-1 polypeptides described herein, without involving a proteolytic cleavage step for removal of an N-terminal peptide. This is particularly advantageous for production of the modified FGF-1 polypeptides per good manufacturing practice (GMP) guidelines. The advantages include the lack of a cleavage step, including eliminating the need for subsequent purification of the cleaved product and removal of the reagents used for cleavage. The further advantage of this is an increase in yield due to decreased handling and the alleviation of the need to test for residual cleavage reagents and contaminants introduced for the cleavage and subsequent separation of cleaved from uncleaved material.

Methods of Use

Provided herein, in one embodiment, is a method of treating an ocular disease, disorder or condition in a mammal comprising administering to the mammal a modified FGF-1 polypeptide as described in the above embodiments. In some instances, the modified FGF-1 polypeptide for use in the methods described herein comprises a sequence selected from SEQ ID NOs: 2, 9-204, and 207. Provided herein, in one embodiment, is a method of treating an ocular disease, disorder or condition in a mammal comprising administering to the mammal a modified FGF-1 polypeptide comprising a sequence as set forth in SEQ ID NO: 205 or 206.

In some embodiments, the ocular disease, disorder or condition to be treated is a disease, disorder, or condition of the corneal endothelial layer. Diseases, disorders, or conditions of the corneal endothelial layer include, but are not limited to, Fuch's dystrophy, bullous keratopathy, congenital hereditary endothelial dystrophy 1, congenital hereditary endothelial dystrophy 2, posterior polymorphous corneal dystrophy, and dry eye syndromes.

Without being bound by theory, it is believed a solution of a modified FGF-1 polypeptide injected intracamerally into the aqueous humor of the eye binds to the endothelial surface and especially any areas of the cornea that are not covered by a healthy endothelial layer. The modified FGF stimulates the growth and migration of the endothelial cells. This reduces the corneal edema associated with the endothelial dystrophy and reduces the likelihood for a need for a corneal or endothelial transplant. The action of the modified FGF can occur at a site other than the site of greatest dystrophy (typically at the corneal center) and also results in stimulation of endothelial cells in the corneal periphery and endothelial progenitor pools in the trabecular meshwork (TM).

In some embodiments, the ocular disease, disorder or condition to be treated is a disease, disorder, or condition of the corneal epithelium. Diseases, disorders or conditions of the corneal epithelium include, but are not limited to, dry eye syndromes, inflammatory conditions such as Stevens-Johnson syndrome, and corneal epithelial defects.

In some embodiments, the ocular disease, disorder or condition to be treated is herpetic keratopathy. Herpetic keratopathy typically is an infection of the cornea caused by Herpes Simplex virus (HSV). Primary infection can be the result of direct exposure of the host's mucous membranes to infectious HSV. Following primary infection and the establishment of latency in the sensory ganglia, the virus can be stimulated to enter an infectious cycle, from which it returns to the cornea. Once there, this recurrent infection can cause various complications, in particular an inflammatory response, which if strong enough can compromise the integrity of the cornea, leading to corneal ulcer, opacity, haze, scarring and in severe cases blindness. Secondary to herpes infection, there can be development of chronic herpetic keratopathy, neurotrophic keratopathy, or both. For example, stromal infections, which are immune-mediated and are the leading cause of corneal blindness in developed countries occur as a result of chronic viral reactivation, and lead to neurotrophic keratopathy, a degenerative condition. A normal cornea is densely innervated, but lacks blood vessels. Subsequent episodes following primary viral infection can not only damage nerves, leading to decreased corneal sensation (corneal hypoesthesia), but also lead to angiogenesis, and neovascularization.

In further embodiments, the modified FGF-1 polypeptides described herein can be used to treat epithelial basement membrane dystrophy, Meesmann juvenile epithelial corneal dystrophy, gelatinous drop-like corneal dystrophy, Lisch epithelial corneal dystrophy, subepithelial mucinous corneal dystrophy, Reis-Bucklers corneal dystrophy, or Thiel-Behnke dystrophy, and recurrent corneal erosions.

In some embodiments, the ocular condition includes damage to the cornea (e.g., the corneal surface or endothelial layer at the interface of the cornea and aqueous humor) or surgical disruption caused by corneal surgeries, including PRK, LASIK, and any penetrating corneal surgery or keratoplasty.

Also provided herein is a method of treating a chemical or vesicant agent induced injury by administering a modified fibroblast growth factors (FGF-1) polypeptides, or pharmaceutical composition or medicaments that include such modified peptides.

Also provided herein in one embodiment is a method of treating a chemical or vesicant injury by administering a modified FGF-1 polypeptide as described herein. In some embodiments, the method comprises treating a skin injury or an ocular injury caused by a chemical or a vesicant agent. In some embodiments, the method comprises treating mustard gas keratopathy, induced by a vesicant, e.g., nitrogen mustard (NM), by administering modified FGF-1 as polypeptides described herein. Treating MGK with a modified FGF-1 polypeptide, as described herein, in some embodiments, results in amelioration of histopathological conditions associated with MGK, such as hyperplasia of corneal epithelial layer, epithelial-stromal cell separation edema, corneal erosions. The administration of modified FGF-1 of the present disclosure, in certain embodiments, results in reduction in edema and elimination of corneal erosions.

Corneal erosion is typically characterized by de-epithelialization of the cornea and in some examples; administration of the modified FGF-1 results in faster re-epithelialization of the cornea or reduces the severity of corneal de-epithelialization. In one embodiment is described a method of regenerating ocular surface epithelium in a patient exposed to a chemical or a vesicant, by administering a modified FGF-1 as described herein. In some embodiments, the method promotes regeneration of cornea, prevents degeneration of the cornea, and prevents long term sequelae to the chemical injury. In some examples, the method comprises treating a corneal endothelial injury, a corneal epithelial injury, or a corneal stromal injury. In instances where the method treats corneal endothelial injuries, administering a modified FGF-1, as described herein, enhances the function of corneal endothelial cells and prevents long term degeneration of the cornea. In some instances, where the method treats corneal endothelial injuries, administering a modified FGF-1, as described herein, prevents corneal edema and secondary anterior keratopathies. In some instances, where the method treats corneal endothelial injuries, administering a modified FGF-1, as described herein, prevents loss of corneal endothelial cells. In some embodiments, the method results in reduction of the severity of corneal epithelial detachment. In some embodiments, the method comprises treating a stromal injury such as stromal scarring and corneal opacity.

In some embodiments, the ocular condition includes accidental trauma or chemical or thermal injury to the cornea. In some examples, the chemical or thermal injury is a chemical burn. In some examples, the chemical or thermal injury is caused by a vesicant agent. In some examples, the chemical or thermal injury is caused by a chemical warfare agent.

A multitude of household and occupational compounds have the potential to induce chemical burns to the eye and skin. Without prompt intervention, irreversible visual loss and disfigurement may prevail. Agents that rapidly neutralize both acid and alkali agents without heat release and limit diffusion, are contemplated to be effective in treating chemical injuries. Exemplary chemical injuries include, but are not limited to, alkali injuries, acid injuries. Common sources of chemical burns include sulfuric acid ($H_2SO_4$), hydrochloric acid (HCl), sodium hydroxide (NaOH), lime (CaO), silver nitrate ($AgNO_3$), hydrogen peroxide ($H_2O_2$), chlorine gas and any strong oxidant.

Exemplary chemical warfare agent that can cause the chemical or thermal injury described herein, is phosgene, an urticant, or a nettle agent. Phosgene is a highly toxic, colorless gas at room temperature and standard pressure that condenses at 0° C. to a fuming liquid. Its molecular formula is $COCl_2$. Phosgene is extremely toxic by acute (short-term) inhalation exposure. Severe respiratory effects, including pulmonary edema, pulmonary emphysema, and death have been reported in humans. Severe ocular irritation and dermal burns may result following eye or skin exposure. Chronic (long-term) inhalation exposure to phosgene may also cause irreversible pulmonary changes, such as emphysema and fibrosis. Its exposure can result in widespread and devastating effects including high mortality due to its fast penetration and ability to cause immediate severe cutaneous injury. Results from a recent study show that topical cutaneous exposure to phosgene vapor causes blanching of exposed skin with an erythematous ring, necrosis, edema, mild urticaria and erythema within minutes after exposure out to 8 h post-exposure, in a mouse model. These clinical skin manifestations are accompanied with increases in skin thickness, apoptotic cell death, mast cell degranulation, myeloperoxidase activity indicating neutrophil infiltration, p53 phosphorylation and accumulation, and an increase in COX-2 and TNFα levels. Topical phosgene-exposure also resulted in the dilatation of the peripheral vessels with a robust increase in RBCs in vessels of the liver, spleen, kidney, lungs and heart tissues. It is contemplated that these events could cause a drop in blood pressure leading to shock, hypoxia and death. See, Tewari-Singh N, Goswami D G, Kant R, Croutch C R, Casillas R P, Orlicky D J, Agarwal R, *Cutaneous exposure to vesicantphosgene oxime: Acute effects on the skin and systemic toxicity*, Toxicol Appl Pharmacol. 2017 Feb. 15; 317:25-32.

In some embodiments, the modified FGF-1 polypeptide may be used in a method of treating, preventing, or ameliorating the various skin injuries caused by vesicant exposure.

Figure 12:
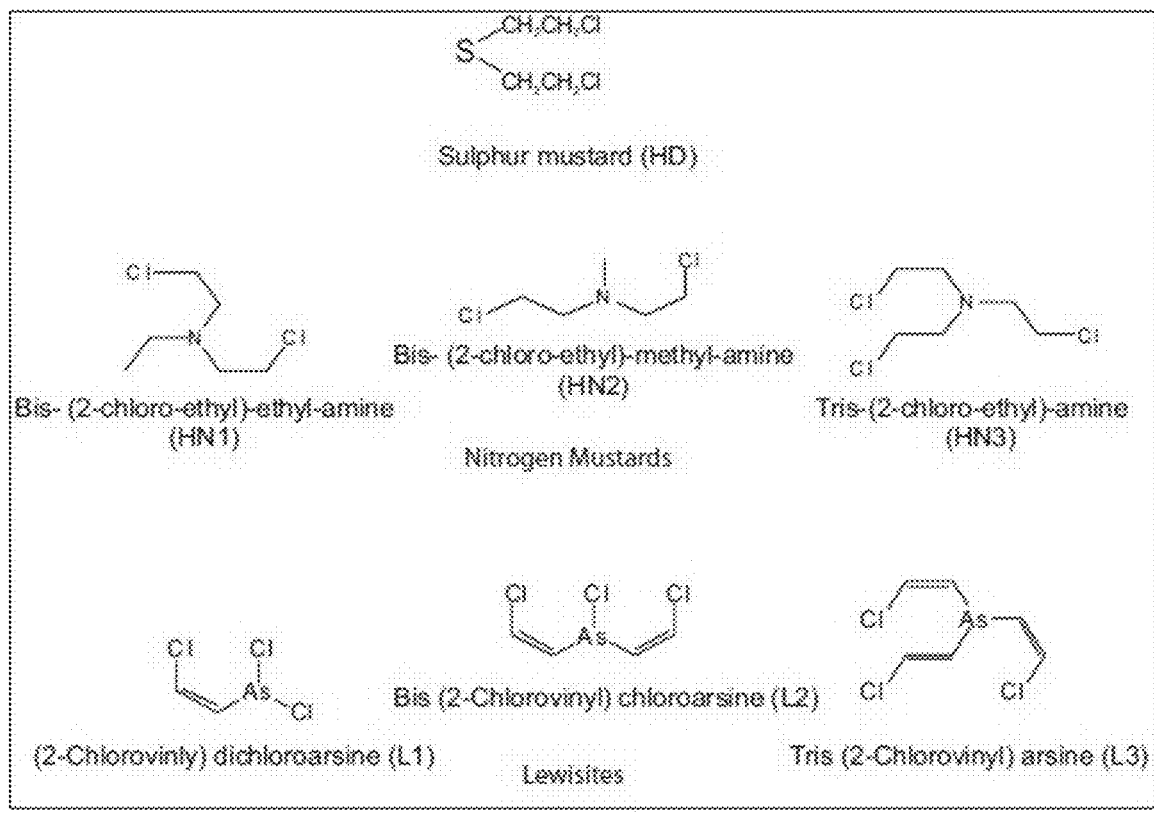
FIG. 12 shows structures of exemplary vesicants.

Vesicants, or vesicant agents, or blistering agents are toxic compounds that produce skin injuries resembling those caused by burns. These agents on inhalation affect the upper respiratory tract as well as the lungs, producing pulmonary edema. See, e.g., Ganesan, K., S. K. Raza, and R. Vijaraghavan (2010) *Chemical Warfare Agents*, Journal of Pharmacy and Bioallied Sciences 2.3: 166-178. These agents can also cause severe eye injuries. There are two forms of vesicants: mustards and arsenicals. The most important substance in this class of chemical warfare agents is sulfur mustard. Other members include nitrogen mustards (HN1, HN2 and HN3), and arsenic vesicants such as lewisites (L1, L2 and L3), ethyldichloroarsine, methyldichloroarsine, phenyldichloriarsine. FIG. 12 shows some example structures of vesicant agents. Specific examples of vesicant agents include but are not limited to sulfur mustard (SM), bis-(2-chloroethyl) sulfide, chloroethylethyl sulfide (CEES), lewisite, and 2-chloro-N-(2-chloroethyl)-N-methylethanamine hydrochloride, a member of the family of nitrogen mustard (NM). As used throughout this disclosure, the terms vesicant, vesication-causing agent or chemical, vesicating agent, and the like, are taken to mean vesicants as specifically enumerated herein, and other compounds, such as toxins and/or chemical warfare agents. Sulfur mustard is the vesicant with the highest military significance since its use in WWI. The nitrogen mustards were synthesized in the 1930s but were not produced in large amounts for warfare. Mechlorethamine (HN2, Mustargen) has found more peaceful applications as a cancer chemotherapeutic agent and has remained the standard compound for this purpose for many years. Lewisite (L) was synthesized in 1918 for military purpose due to its non-flammable property and toxicity similar to mustard, but has probably not been used on a battlefield. The mustards are radiomimetic and are extremely toxic to dividing cells. Mustards are lipophilic and readily penetrate the skin, most textiles and rubber. After passing through the cellular membrane, sulfur mustard is converted to highly reactive sulphonium ion. It irreversibly alkylates DNA, RNA and protein, causing cell death; the most important target is DNA. Mustard alkylates the purine bases of DNA and damages them. Lewisite is absorbed by the skin much faster, and it causes immediate pain and irritation in the affected organ and produces more systematic symptoms. It directly binds to the sulfhydryl groups and inactivates them.

The use of sulfur mustard (SM), and other vesicating agents in chemical warfare has been long known. More recently, in August 2015, SM was used by ISIS in an attack on Kurdish forces in Iraq, as well as an attack in Syria. Mustard agents injure the eyes, the skin, and the lungs, with the eyes being the most sensitive. Because symptoms do not manifest until 2 to 4 hours after exposure, exposed persons do not immediately know they are exposed to mustard. This delay has contributed to confusion and panic when symptoms of exposure finally develop. For the eyes, these consist of blepharospasm, lacrimation, irritation, pain, and photophobia. Corneal injuries resulting from ocular exposure to sulfur mustard (SM) vapor are the most prevalent chemical warfare injury. Ocular exposures exhibit three distinct, dose-dependent clinical trajectories: complete injury resolution, immediate transition to a chronic injury, or apparent recovery followed by the subsequent development of persistent ocular manifestations. These latter two trajectories include a constellation of corneal symptoms that are collectively known as mustard gas keratopathy (MGK). Tissue-specific damage during the acute injury can decrement the regenerative capacities of corneal endothelium and limbal stem cells, thereby predisposing the cornea to the chronic or delayed forms of MGK.

For some patients MGK occurs a few weeks after exposure; in others it took years to manifest. This keratopathy is characterized by corneal conjunctivalization and limbal stem cell deficiency. It has been shown that in the human corneal endothelium, gaps due to CEC loss are typically filled by spreading of proximal CECs. These morphological changes compensate for endothelial loss until the barrier between the cornea and aqueous humor can no longer be maintained, resulting in persistent corneal edema and secondary anterior keratopathies. Because adult human CECs do not proliferate in vivo, any loss of CECs therefore potentially represents a permanent reduction in endothelial capacity. Thus, while endothelial function can be restored after a mild injury by CEC spreading, more severe injuries may exceed the repair capacity of the human endothelium. Rabbits are distinct from humans in that they can undergo limited CEC proliferation, giving them an improved capacity to recover from CEC loss. However, as in humans, sufficiently severe injury to the rabbit endothelium also results in irreversible corneal decompensation and secondary keratopathies.

Based on the above studies, it has been hypothesized that vesicant-induced endothelial failure may be the causal mechanism underlying MGK pathogenesis. This hypothesis is consistent with the dose dependence between SM and the development of MGK that has been observed in humans and rabbits, as well as the different clinical trajectories (resolved chronic MGK and delayed-onset MGK) that have been reported in human casualties. According to this hypothesis, cornea exposure to low doses of vesicant may result in an acute epithelial lesion, with minimal endothelial toxicity, and corneas recover without long-term complications. Alternatively, exposure to doses of a vesicant that cause irreparable injury to the corneal endothelium could result in endothelial barrier failure, producing a persistent edema with secondary anterior keratopathies. Following a severe injury, there may be no apparent delay between the acute injury and MGK onset.

Hence, a composition and method for minimizing or preventing injury due to sulfur mustard and similarly acting chemical toxicants, particularly chemical warfare agents, is an important pursuit for scientists working for the U.S. Department of Defense. Recent studies have shown that as vesicating agents, mustard compounds lead to a loss of epithelial-stromal attachment. In the cornea, microbullae are formed, and once enough have accrued, the corneal epithelium is unable to hold fast to the basement membrane, causing the epithelial tissue to slough. Thus, an effective post-exposure therapy for SM is desired to enhance the ability of the corneal epithelium to remain attached to the stroma. Without being bound by a theory, it is contemplated that the ability of the corneal epithelium to remain attached to the stroma might allow some basal epithelia the opportunity to recover in situ, maintaining their connections with their basement membrane and stroma. It has also been hypothesized that one of the key players in the epithelial-stromal integrity is collagen XVII (i.e., BP180), a transmembranous component of the hemidesmosome. Cleavage of collagen XVII by ADAM ("A Disintegrin And Metalloproteinase") family of proteins, including ADAM9, ADAM10, and/or ADAM17 after injury releases epithelial cells from their basement membrane, and this cleavage allows them to migrate.

ADAM17, also known as TNF-α converting enzyme or TACE, is a general response to injury as well as a "sheddase" for releasing collagen XVII. It was postulated that corneal microblistering, induced by vesicant agent exposure, is in part due to activation of ADAM17, which is capable of cleaving collagen XVII. Experimental data confirmed the induction of ADAM17 expression at the basement membrane zone of corneas exposed to vesicant agent NM. Thus, agents that are able to inhibit the post-exposure upregulation of ADAM17 expression are contemplated to be useful for attenuation of corneal injuries caused by vesicant agents.

The present disclosure provides modified FGF-1 polypeptides that treat, reduce the adverse effects or, and otherwise aid in the healing of exposure to vesicant agents, such as SM and NM. The modified FGF-1 polypeptides disclosed herein are capable of preventing the overexpression of ADAM17 following exposure to a vesicant agent, such as SM and/or NM.

The present disclosure also provides a method of treating, preventing, reducing the adverse effects of, and otherwise aiding the healing of exposure to chemical or vesicant induced injury, by administering a modified FGF-1 polypeptide. In some embodiments, the methods disclosed herein further prevent the overexpression of ADAM17 following exposure to a vesicant agent, such as SM and/or NM.

Wild type FGF-1 proteins, e.g., SEQ ID NO: 1, which have unpaired cysteine residues that are susceptible to oxidation and alkylation. See FIG. 1. In some embodiments of the present disclosure where the modified FGF-1 polypeptides do not comprise unpaired cysteine residues, such modified FGF-1 polypeptides are less susceptible to oxidation and/or alkylation by vesicant agents. Experimental data has also indicated reduction in levels of FGF-1 and its mRNA are known to result from exposure to mustard agents and it is hypothesized that this loss may play a role in the slow healing of mustard-induced lesions in the cornea. In some embodiments of the present disclosure, the modified FGF-1 polypeptides, which do not comprise free cysteine residues and accordingly are less or not susceptible to cysteine modification, are effective in accelerating the healing of corneal mustard lesions.

In some embodiments of the present disclosure, the method comprises administering a modified FGF-1 polypeptide that do not comprise unpaired cysteine residues, which modified FGF-1 polypeptides are less susceptible to oxidation and/or alkylation by vesicant agents. In some embodiments of the present disclosure, the method comprises administering a modified FGF-1 polypeptides, which do not comprise free cysteine residues and accordingly are less or not susceptible to cysteine modification. In some embodiments, the method disclosed herein is effective in accelerating the healing of corneal lesions associated with MGK.

Exposure to vesicant agents, such as sulfur mustard (SM) and nitrogen mustard (NM) can cause severe skin injury with delayed blistering. Depending upon the dose and time of their exposure, edema and erythema can potentially develop into blisters, ulceration, necrosis, desquamation, and pigmentation changes, which persist weeks and even years after exposure. See, e.g., Tewari-Singh N, Agarwal R, *Mustard vesicating agent-induced toxicity in the skin tissue and silibinin as a potential countermeasure*, Ann N Y Acad Sci. 2016 June; 1374(1):184-92. Another exemplary vesicant agent Phosgene Oxime (CX), an urticant or nettle agent, is also a potential chemical warfare and terrorist weapon.

In some embodiments, the ocular disease, disorder or condition to be treated is a disease, disorder, or condition of the corneal stroma. Diseases, disorders or conditions of the corneal stroma include, but are not limited to, keratoconus, lattice corneal dystrophy, granular corneal dystrophy, macular corneal dystrophy, Schnyder crystalline corneal dystrophy, congenital stromal corneal dystrophy, fleck corneal dystrophy, trauma or chemical or thermal injury, or injury secondary to infections such as trachoma.

In further embodiments, the modified FGF-1 polypeptides described herein can be applied before, during, or after corneal transplantations procedures (e.g., corneal transplantation or procedures involving Descemet's membrane) that involve disruption of the cornea (e.g., corneal endothelial structure) where acceleration of healing of corneal or ocular surface cells and/or improving the cellular response (e.g., by increasing the viability and/or longevity of the transplanted cells) to insult would result in a therapeutic benefit.

In additional embodiments, the modified FGF-1 polypeptides described herein can be used to increase the viability and health of corneal cells or corneal progenitors being prepared for transplantation. Modified FGF-1 polypeptides added to the organ culture medium for donated corneas or other donated corneal tissue stimulates the corneal cells and increases the length of time the corneas can be stored before transplantation, as well as increasing the probability that a cornea will have sufficient healthy cells to be useful for transplantation. Also, the modified FGF-1 polypeptides can be used in culture media when culturing corneal progenitor cells to stimulate growth of those cells.

Further embodiments relate to methods of modulating the activity of one or more fibroblast growth factor receptors (FGFRs) in a corneal endothelial cell comprising contacting said corneal endothelial cell with a modified FGF (e.g., a modified FGF-1, such as one comprising the sequence of SEQ ID NO: 2). Such methods can be used to increase or stimulate the activity of one or more FGFRs, which can result in increased cell migration and/or cell proliferation.

In additional embodiments are described methods of treating a metabolic disease by administering a modified FGF-1 polypeptide according to the present disclosure. Exemplary metabolic diseases that can be treated with the disclosed modified FGF-1 polypeptides include but are not limited to: (1) glucose utilization disorders and the sequelae associated therewith, including diabetes mellitus (Type I and Type-2), gestational diabetes, hyperglycemia, insulin resistance, abnormal glucose metabolism, "pre-diabetes" (Impaired Fasting Glucose (IFG) or Impaired Glucose Tolerance (IGT)), and other physiological disorders associated with, or that result from, the hyperglycemic condition, including, for example, histopathological changes such as pancreatic R-cell destruction; (2) dyslipidemias and their sequelae such as, for example, atherosclerosis, coronary artery disease, cerebrovascular disorders and the like; (3) other conditions which may be associated with the metabolic syndrome, such as obesity and elevated body mass (including the co-morbid conditions thereof such as, but not limited to, nonalcoholic fatty liver disease (NAFLD), nonalcoholic steatohepatitis (NASH), and polycystic ovarian syndrome (PCOS)), and also include thromboses, hypercoagulable and prothrombotic states (arterial and venous), hypertension, cardiovascular disease, stroke and heart failure; (4) disorders or conditions in which inflammatory reactions are involved, including atherosclerosis, chronic inflammatory bowel diseases (e.g., Crohn's disease and ulcerative colitis), asthma, lupus erythematosus, arthritis, or other inflammatory rheumatic disorders; (5) disorders of cell cycle or cell differentiation processes such as adipose cell tumors, lipomatous carcinomas including, for example, liposarcomas, solid tumors, and neoplasms; (6) neurodegenerative diseases and/or demyelinating disorders of the central and peripheral nervous systems and/or neurological diseases involving neuroinflammatory processes and/or other peripheral neuropathies, including Alzheimer's disease, multiple sclerosis, Parkinson's disease, progressive multifocal leukoencephalopathy and Guillian-Barre syndrome; (7) skin and dermatological disorders and/or disorders of wound healing processes, including erythemato-squamous dermatoses; and (8) other disorders such as syndrome X, osteoarthritis, and acute respiratory distress syndrome. Also described are methods of reducing fed and fasting blood glucose, improving insulin sensitivity and glucose tolerance, reducing systemic chronic inflammation, ameliorating hepatic steatosis in a mammal, reducing food intake, or combinations thereof, by administering a therapeutically effective amount of a disclosed modified FGF-1 polypeptide (or nucleic acid molecules encoding such).

In some embodiments, the modified FGF-1 polypeptides are administered for wound healing. Examples of wounds include, but are not limited to, abrasions, avulsions, blowing wounds (e.g., open pneumothorax), burn wounds, contusions, gunshot wounds, incised wounds, open wounds, penetrating wounds, perforating wounds, puncture wounds, seton wounds, stab wounds, surgical wounds, subcutaneous wounds, diabetic lesions, or tangential wounds. Additional examples of wounds that can be treated by the compounds and compositions described herein include acute conditions or wounds, such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies; trauma-induced injuries including cuts, incisions, excoriations; injuries sustained from accidents; post-surgical injuries, as well as chronic conditions, such as pressure sores, bedsores, conditions related to diabetes and poor circulation, and all types of acne. In addition, the wound can include dermatitis, such as impetigo, intertrigo, folliculitis and eczema, wounds following dental surgery; periodontal disease; wounds following trauma; and tumor-associated wounds. Yet other examples of wounds include animal bites, arterial disease, insect stings and bites, bone infections, compromised skin/muscle grafts, gangrene, skin tears or lacerations, skin aging, surgical incisions, including slow or non-healing surgical wounds, intracerebral hemorrhage, aneurysm, dermal asthenia, and post-operation infections.

A therapeutic peptide of the present invention may also be used to treat external wounds caused by, but not limited to scrapes, cuts, lacerated wounds, bite wounds, bullet wounds, stab wounds, burn wounds, sun burns, chemical burns, surgical wounds, bed sores, radiation injuries, all kinds of acute and chronic wounds, wounds or lesions created by cosmetic skin procedures. The peptide may also be used to ameliorate the effects of skin aging. The peptide may accelerate wound healing in an external wound and/or improve the cosmetic appearance of wounded areas, or skin subject to aging and disease. The peptide may be used to treat internal injury caused by, but not limited to, disease, surgery, gunshots, stabbing, accidents, infarcts, ischemic injuries, to organs and tissues including but not limited to heart, bone, brain, spinal cord, retina, peripheral nerves and other tissues and organs commonly subject to acute and chronic injury, disease, congenital and developmental malformation and aging processes.

In some embodiments, the modified FGF-1 polypeptides are administered for treating burn injury. Exemplary burn wounds include, but are not limited to, "burn ulcers" including, for example, ulceration that occur as a result of a burn injury, including a first degree burn (i.e., superficial, reddened area of skin); a second degree burn (a blistered injury site which may heal spontaneously after the blister fluid has been removed); a third degree burn (burn through the entire skin and usually require surgical intervention for wound healing); scalding (may occur from scalding hot water, grease or radiator fluid); a thermal burn (may occur from flames, usually deep burns); a chemical burn (may come from acid and alkali, usually deep burns); an electrical burn (either low voltage around a house or high voltage at work); an explosion flash (usually superficial injuries); and contact burns (usually deep and may occur from muffler tail pipes, hot irons, and stoves). As used herein, a delayed or difficult to heal wound may include, for example, a wound that is characterized at least in part by 1) a prolonged inflammatory phase, 2) a slow forming extracellular matrix (ECM), and 3) a decreased rate of epithelialization. It has been shown that growth factors, e.g. FGF-1, play an important role in nerve regeneration and nerve healing. FGF-1 has been suggested for use in regenerating nervous system tissue following spinal cord injury or trauma, such as brachial plexus injury, neuroimmunologic disorders, such as acute or idiopathic transverse myelitis (TM), or any other disease or condition where regeneration and/or protection of neurons or neural tissue is desired, since FGF-1 is believed to stimulate neural proliferation and growth and may be neuroprotective. See, e.g., Cheng, H. et al., "Spinal Cord Repair with Acidic Fibroblast Growth Factor as a Treatment for a Patient with Chronic Paraplegia," SPINE 29(14):E284-E288 (2004); and Lin, P-H., "Functional recovery of chronic complete idiopathic transverse myelitis after administration of neurotrophic factors," Spinal Cord 44:254-257 (2006). FGF-1 is known to have a neurotrophic activity, promote axonal growth, and exert beneficial effects in models of spinal cord injury and axon regeneration. Accordingly, in some embodiments the modified FGF-1 polypeptide of the present disclosure promotes neural regeneration and can be used in methods of treating conditions that benefit from neural regeneration. In some example methods, the neurological condition is amyotrophic lateral sclerosis (ALS). In some example methods, the neurological condition is acute or idiopathic transverse myelitis (TM). In certain instances, the modified FGF-1 polypeptide can be administered in combination with other growth factors, as well as other pharmaceutically active components, for treating conditions that benefit from neural; regeneration.

Pharmaceutical Compositions, Methods of Administration, and Dosing

Pharmaceutical compositions comprising a modified FGF-polypeptide as described herein may be formulated in a conventional manner using one or more physiologically acceptable carriers including excipients and auxiliaries which facilitate processing of the active compounds into preparations which can be used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a modified FGF with other chemical components, such as carriers, stabilizers, diluents, dispersing agents, suspending agents, thickening agents, and/or excipients, and, optionally, other therapeutic and/or prophylactic ingredients. The pharmaceutical composition facilitates administration of the modified FGF to an organism. In practicing the methods of treatment or use provided herein, therapeutically effective amounts of modified FGF-1 polypeptides described herein are administered in a pharmaceutical composition to a mammal having an ocular disease, disorder, or condition to be treated. In some embodiments, the mammal is a human. A therapeutically effective amount can vary widely depending on the severity of the disease, the age and relative health of the subject, the potency of the compound used and other factors. A pharmaceutically acceptable or suitable composition includes an ophthalmologically suitable or acceptable composition.

A pharmaceutical composition (e.g., for delivery by injection or for application as an eye drop) may be in the form of a liquid or solid. A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. Physiological saline is commonly used as an excipient, and an injectable pharmaceutical composition or a composition that is delivered ocularly (for example, as an eye drop) is preferably sterile.

A modified FGF-polypeptide or pharmaceutical composition described herein can be delivered to a subject by any suitable means, including, for example, topically, intraocularly, intracamerally, orally, parenterally, intravenously, intraperitoneally, intranasally (or other delivery methods to the mucous membranes, for example, of the nose, throat, and bronchial tubes), or by local administration to the eye, or by an intraocular or periocular device. Modes of local administration can include, for example, topical application, eye drops, intraocular injection or periocular injection. Periocular injection typically involves injection of the compound under the conjunctiva or into the Tennon's space (beneath the fibrous tissue overlying the eye). Intraocular injection typically involves injection of the modified FGF or pharmaceutical composition into the vitreous. In certain embodiments, the administration is non-invasive, such as by topical application or eye drops. In some embodiments, the administration is via a combination of topical and intracameral method.

A modified FGF or pharmaceutical composition described herein can be formulated for administration using pharmaceutically acceptable (suitable) carriers or vehicles as well as techniques routinely used in the art. A pharmaceutically acceptable or suitable carrier includes an ophthalmologically suitable or acceptable carrier. A carrier is selected according to the solubility of the particular modified FGF. Suitable ophthalmological compositions and formulations include those that are administrable locally to the eye, such as by eye drops, injection or the like. In the case of eye drops, the formulation can also optionally include, for example, ophthalmologically compatible agents such as isotonizing agents such as sodium chloride, concentrated glycerin, and the like; buffering agents such as sodium phosphate, sodium acetate, and the like; surfactants such as polyoxyethylene sorbitan mono-oleate (also referred to as Polysorbate 80), polyoxyl stearate 40, polyoxyethylene hydrogenated castor oil, and the like; stabilization agents such as sodium citrate, sodium edentate, and the like; preservatives such as benzalkonium chloride, parabens, and the like; and other ingredients. Preservatives can be employed, for example, at a level of from about 0.001 to about 1.0% weight/volume. The pH of the formulation is usually within the range acceptable to ophthalmologic formulations, such as within the range of about pH 4 to 8.

For injection, the modified FGF or pharmaceutical composition can be provided in an injection grade saline solution, in the form of an injectable liposome solution, slow-release polymer system or the like. Intraocular and periocular injections are known to those skilled in the art and are described in numerous publications including, for example, Spaeth, Ed., *Ophthalmic Surgery: Principles of Practice*, W. B. Sanders Co., Philadelphia, Pa., 85-87, 1990.

In some embodiments, the modified FGF or pharmaceutical composition (e.g., an ophthalmic formulation) is administered via microneedles into the cornea (Jiang et al. (2007). *Invest Ophthalmol Vis Sci* 48(9): 4038-4043). A microneedle array is coated with the modified FGF or pharmaceutical composition and pressed against the cornea such that the microneedles penetrate into the corneal stroma but do not penetrate the entire cornea. It is then removed, and the modified FGF or pharmaceutical composition is left behind in the corneal stroma. This modified FGF or pharmaceutical composition can stimulates the corneal cells to proliferate and migrate, and suppresses the scarring response that the stromal cells normally have.

For delivery of a composition comprising at least one of the modified FGF-1 polypeptides described herein via a mucosal route, which includes delivery to the nasal passages, throat, and airways, the composition may be delivered in the form of an aerosol. The compound may be in a liquid or powder form for intramucosal delivery. For example, the composition may be delivered via a pressurized aerosol container with a suitable propellant, such as a hydrocarbon propellant (e.g., propane, butane, isobutene). The composition may be delivered via a non-pressurized delivery system such as a nebulizer or atomizer.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, PA (2005)).

The modified FGF-1 polypeptides or pharmaceutical compositions described herein may be formulated for sustained or slow-release. Such compositions may generally be prepared using well known technology and administered by, for example, periocular, intraocular, rectal, oral or subcutaneous implantation, or by implantation at the desired target site, or by topical application. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained-release formulation depends upon the site of implantation, the rate and expected duration of release, and the nature of the condition to be treated or prevented.

Systemic drug absorption of a drug or composition administered via an ocular route is known to those skilled in the art (see, e.g., Lee et al., *Int. J. Pharm.* 233:1-18 (2002)). In one embodiment, a compound described herein is delivered by a topical ocular delivery method (see, e.g., *Curr. Drug Metab.* 4:213-22 (2003)). The composition may be in the form of an eye drop, salve, or ointment or the like, such as, aqueous eye drops, aqueous ophthalmic suspensions, non-aqueous eye drops, and non-aqueous ophthalmic suspensions, gels, ophthalmic ointments, etc. For preparing a gel, for example, carboxyvinyl polymer, methyl cellulose, sodium alginate, hydroxypropyl cellulose, ethylene maleic anhydride polymer and the like can be used.

In another embodiment, the modified FGF solution or pharmaceutical composition (e.g., an ophthalmic formulation) contains hyaluronic acid, carboxymethyl cellulose, or other polysaccharides that provide increased ocular tolerability, viscosity and osmolality to produce a comfortable ocular solution.

The dose of the modified FGF or pharmaceutical composition comprising at least one of the modified FGF-1 polypeptides described herein may differ, depending upon the patient's (e.g., human) condition, that is, stage of the ocular disease, disorder, or condition, general health status, age, and other factors that a person skilled in the medical art will use to determine dose. When the composition is used as eye drops, for example, one to several drops per unit dose, preferably 1 or 2 drops (about 50 μl per 1 drop), may be applied about 1 to about 6 times daily.

Pharmaceutical compositions may be administered in a manner appropriate to the disease, disorder, or condition to be treated (or prevented) as determined by persons skilled in the medical arts. An appropriate dose and a suitable duration and frequency of administration will be determined by such factors as the condition of the patient, the type and severity of the patient's disease, disorder, or condition, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free, or a lessening of symptom severity). For prophylactic use, a dose should be sufficient to prevent, delay the onset of, or diminish the severity of an ocular disease, disorder, or condition. Optimal doses may generally be determined using experimental models and/or clinical trials. The optimal dose may depend upon the body mass, weight, or blood volume of the patient.

In various embodiments, a modified FGF-1 polypeptide of the present disclosure may be administered as a daily dose over a period of time to a subject. In some embodiments, a modified FGF-1 polypeptide of the present disclosure may be administered chronically or long-term. In some embodiments, a modified FGF-1 polypeptide of the present disclosure may be administered for a period of days, weeks, months, years or continued therapy over the lifetime of a subject. In some embodiments, a modified FGF-1 polypeptide of the present disclosure may be administered for a period of about 7 days, 15 days, about 21 days, about 30 days, about 3 months, about 6 months, about 12 months, about 18 months, about 2 years, about 5 years, about 7 years, about 10 years, about 15 years, about 20 years, about 25 years, about 30 years, about 35 years, or about 40 years. In some embodiments, a treatment regime may be determined for an individual subject dependent on various factors. In some examples, the treatment regimen is dependent on the level of exposure to a compound causing a chemical or thermal injury, such as a vesicant compound. In some embodiments, the treatment regimen is about 2 weeks for an acute exposure and several months to a year for a long term exposure. In some embodiments, the treatment regimen is chronic. In some examples, a factor may include, but not be limited to, a determination of the change in the extent of degeneration of corneal tissue in response to administration of a modified FGF-1 polypeptide of the present disclosure. In some examples, a factor may include, but not be limited to, amelioration of MGK sequelae in response to administration of a modified FGF-1 polypeptide of the present disclosure. In some examples, a factor may include, but not be limited to, healing of corneal endothelial lesions in response to administration of a modified FGF-1 polypeptide of the present disclosure. In some examples, a factor may include, but not be limited to, corneal epithelial cell proliferation in response to administration of a modified FGF-1 polypeptide of the present disclosure. In some examples, a factor may include, but not be limited to, reduction of symptoms associated with Fuch's dystrophy in response to administration of a modified FGF-1 polypeptide of the present disclosure. In embodiments, a subject exhibiting an immediate response to the composition, for example, an immediate reduction in symptoms associated with Fuch's dystrophy, may require less frequent doses than a subject exhibiting a response to the composition at a later time or after several doses.

The doses of the modified FGF-1 polypeptides or pharmaceutical compositions can be suitably selected depending on the clinical status, condition and age of the subject, dosage form and the like. In the case of eye drops, a modified FGF described herein can be administered, for example, from about 10 ug/ml to about 100 mg/ml of the modified FGF one to seven times per week.

Also provided are methods of manufacturing the modified FGF-1 polypeptides and pharmaceutical compositions described herein. A composition comprising a pharmaceutically acceptable excipient or carrier and at least one of the modified FGF-1 polypeptides described herein may be prepared by synthesizing the modified FGF according to any one of the methods described herein or practiced in the art and then formulating the compound with a pharmaceutically acceptable carrier. Formulation of the composition will be appropriate and dependent on several factors, including but not limited to, the delivery route, dose, and stability of the compound.

At least one modified FGF described herein can be administered to human or other nonhuman vertebrates. In certain embodiments, the modified FGF is substantially pure, in that it contains less than about 5% or less than about 1%, or less than about 0.1%, of other organic molecules, such as contaminating intermediates or by-products that are created, for example, in one or more of the steps of a synthesis method. In other embodiments, a combination of one or more modified FGF-1 polypeptides described herein can be administered.

The compositions described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like.

In the case wherein the patient's condition does not improve, upon the doctor's discretion the administration of the compositions may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compositions may be given continuously; alternatively, the dose of drug being administered may be temporarily reduced or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more modified FGF-1 polypeptides. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

The modified FGF-1 polypeptides and pharmaceutical compositions may also be used in combination with other therapeutic agents that are selected for their therapeutic value for the condition to be treated. The modified FGF-1 polypeptides and pharmaceutical compositions may also be used in combination with other therapeutic agents that are selected for their therapeutic value for treating the vesicant injury. Such agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

The particular choice of these optional additional agents used will depend upon the diagnosis of the attending physicians and their judgment of the condition of the patient and the appropriate treatment protocol. The agents may be administered concurrently (e.g., simultaneously, essentially simultaneously or within the same treatment protocol) or sequentially, depending upon the nature of the disease, disorder, or condition, the condition of the patient, and the actual choice of agents used. The determination of the order of administration, and the number of repetitions of administration of each therapeutic agent during a treatment protocol, is well within the knowledge of the physician after evaluation of the disease being treated and the condition of the patient.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For example, the modified may be incorporated into formulations that contain other active ingredients such as steroids, antibiotics, anti-inflammatories, cytokines such as IL-1 or analogs of IL-1, or antagonists of cytokines such as inhibitors of IL-17.

Other exemplary cytokines include, but are not limited to, interleukins (e.g., IL-2, IL-3, IL-4, IL-5, IL-6, IL-7, IL-8, IL-9, IL-10, IL-11, IL-12, IL-13, IL-15, IL-16, IL-17, IL-18, IL-1α, IL-1β, and IL-1 RA), granulocyte colony stimulating factor (G-CSF), granulocyte-macrophage colony stimulating factor (GM-CSF), oncostatin M, erythropoietin, leukemia inhibitory factor (LIF), interferons, B7.1 (also known as CD80), B7.2 (also known as B70, CD86), TNF family members (TNF-α, TNF-β, LT-β, CD40 ligand, Fas ligand, CD27 ligand, CD30 ligand, 4-1BBL, Trail), and migration inhibitory factor MIF.

In some embodiments, combinations or pharmaceutical compositions described herein are administered in immunosuppressive therapy to reduce, inhibit, or prevent activity of the immune system. Immunosuppressive therapy is clinically used to: prevent the rejection of transplanted organs and tissues; treatment of autoimmune diseases or diseases that are most likely of autoimmune origin; and treatment of some other non-autoimmune inflammatory diseases.

In some embodiments, the modified FGF-1 polypeptides and pharmaceutical compositions described herein are administered with one or more anti-inflammatory agent including, but not limited to, non-steroidal anti-inflammatory drugs (NSAIDs) and corticosteroids (glucocorticoids).

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, and COX-2 specific inhibitors (such as, but not limited to, celecoxib, rofecoxib, valdecoxib, parecoxib, etoricoxib, lumiracoxib, CS-502, JTE-522, L-745,337 and NS398).

Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

Other agents used as anti-inflammatories include those disclosed in U.S. patent publication 2005/0227929, herein incorporated by reference.

Some commercially available anti-inflammatories include, but are not limited to: Arthrotec® (diclofenac and misoprostol), Asacol® (5-aminosalicyclic acid), Salofalk® (5-aminosalicyclic acid), Auralgan® (antipyrine and benzocaine), Azulfidine® (sulfasalazine), Daypro® (oxaprozin), Lodine® (etodolac), Ponstan® (mefenamic acid), Solumedrol® (methylprednisolone), Bayer® (aspirin), Bufferin® (aspirin), Indocin® (indomethacin), Vioxx® (rofecoxib), Celebrex® (celecoxib), Bextra® (valdecoxib), Arcoxia® (etoricoxib), Prexige® (lumiracoxib), Advil®, Motrin® (ibuprofen), Voltaren® (diclofenac), Orudis® (ketoprofen), Mobic® (meloxicam), Relafen® (nabumetone), Aleve®, Naprosyn® (naproxen), Feldene® (piroxicam).

In one embodiment, compositions described herein are administered with leukotriene receptor antagonists including, but are not limited to, BAY u9773 (see EP 00791576; published 27 Aug. 1997), DUO-LT (Tsuji et al, *Org. Biomol. Chem.*, 1, 3139-3141, 2003), zafirlukast (Accolate®), montelukast (Singulair®), prankulast (Onon®), and derivatives or analogs thereof.

In some embodiments, the modified FGF-1 polypeptides and pharmaceutical compositions described herein are administered with one or more Rho kinase inhibitors. In some embodiments, the modified FGF-1 polypeptides and pharmaceutical compositions described herein are administered with one or more additional growth factors, including, but not limited to epidermal growth factor (EGF) and nerve growth factor (NGF). See, e.g., see Joyce et al. (2009) *Invest Ophthalmol. Vis Sci.* 50:2116-2122, vascular endothelial growth factor (VEGF), transforming growth factor alpha and beta (TGF-alpha and TFG-beta), platelet-derived endothelial growth factor (PD-ECGF), platelet-derived growth factor (PDGF), tumor necrosis factor alpha (TNF-alpha), hepatocyte growth factor (HGF), insulin like growth factor (IGF), erythropoietin, colony stimulating factor (CSF), macrophage-CSF (M-CSF), granulocyte/macrophage CSF (GM-CSF) and nitric oxidic synthase (NOS).

Kits/Articles of Manufacture

For use in the therapeutic applications described herein, kits and articles of manufacture are also provided herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products include, e.g., U.S. Pat. Nos. 5,323, 907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of ophthalmic formulations of the modified FGF-1 polypeptides and pharmaceutical compositions provided herein are contemplated as a variety of treatments for any ocular disease, disorder, or condition that would benefit by administration of a modified FGF ore pharmaceutical composition described herein.

For example, the container(s) can include a modified FGF such as a modified FGF-1 having a sequence of SEQ ID NO: 2. The container(s) optionally have a sterile access port. Such kits optionally comprising compounds with an identifying descriptions or labels or instructions relating to their use in the methods described herein.

A kit will typically may include one or more additional containers, each with one or more of various materials (such as reagents, optionally in concentrated form, and/or devices) desirable from a commercial and user standpoint for use of a modified FGF described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, a modified FGF pharmaceutical composition can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a modified FGF provided herein formulated in a compatible pharmaceutical carrier can also be prepared, placed in an appropriate container, and labeled for treatment of an indicated condition.

EXAMPLES

These examples are provided for illustrative purposes only and not to limit the scope of the claims provided herein. The starting materials and reagents used in the examples described herein may be synthesized or can be obtained from commercial sources.

Example 1: Exemplary Modified FGF-1
Polypeptide with an N-Terminal Methionine
(N-Met) has Similar Activity as a Version without
the N-Met The study is directed towards modified FGF-1 polypeptides comprising the sequence of SEQ ID NO: 2 (N-Met-TTHX1114) or SEQ ID NO: 205 (TTHX1001). The modified FGF-1 polypeptides are generated using methods as described above in the Recombinant Techniques section.

Experimental Methods and Results

The biological activity of the test polypeptides are assessed in a NIH-3T3 cell proliferation assay. Results indicate no difference between the modified FGF-1 polypeptides of SEQ ID NO: 2 and SEQ ID NO: 205, in terms of effectivity in inducing proliferation of the fibroblast cells.

Example 2: Effects of Modified FGF-1 Polypeptides on Human Corneal Endothelial Cell (HCEC) Proliferation The study is directed towards modified FGF-1 polypeptides comprising the sequence of SEQ ID NO: 2 (N-Met-TTHX1114) or SEQ ID NO: 205 (TTHX1001). The modified FGF-1 polypeptides are generated using methods as described above in the Recombinant Techniques section.
Experimental Methods and Results
Primary cultures (passage 1) of human corneal endothelial cells from a healthy donor are seeded onto 24 well plates in the presence of fetal bovine serum (FBS, 8%) and 24 hours later treated with the varying concentrations of N-Met-TTHX1114 (SEQ ID NO: 2), TTHX1001 (SEQ ID NO: 205), or wt-FGF-1 (SEQ ID NO: 1) in media with low (0.8%) FBS. The 8% FBS group serves as positive control. Results indicate that N-Met-TTHX1114 is more potent than TTHX1001 or wt-FGF-1 in stimulating human corneal epithelial cell proliferation and is dose responsive therein. The $EC_{50}$ of N-Met-TTHX1114 is about 100-fold lower than the wt-FGF-1 or the other tested modified FGF-1 polypeptide (TTHX1001; SEQ ID NO: 205).

Example 3: Nitrogen Mustard Induced Injury of Cornea

Figure 3:
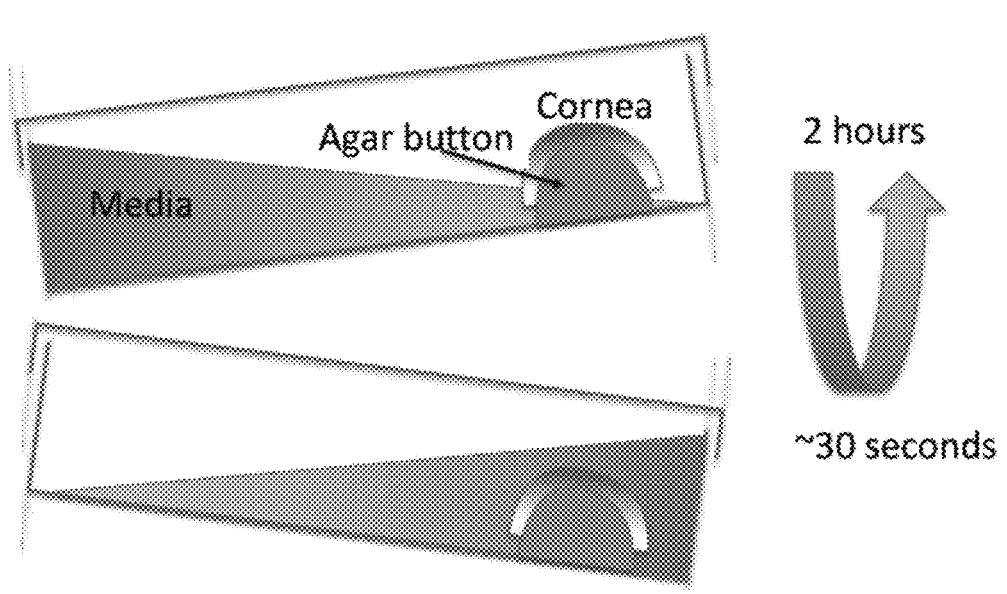
FIG. 3 illustrates an exemplary rabbit corneal organ culture model system.

The study is directed towards the effect of modified FGF-1 polypeptides comprising the sequence of SEQ ID NO: 2 (N-Met-TTHX1114) on treatment of nitrogen mustard (NM) induced corneal injury. The modified FGF-1 polypeptides are generated using methods as described above in the Recombinant Techniques section.
Experimental Methods
A rabbit corneal organ culture model system was used to evaluate healing after exposure to NM. Rabbit eyes (8-12 weeks old) are obtained and corneas with 2-mm scleral rims are dissected from the eyes, placed epithelial-side down into a spot plate, and the concavities were filled with 558 C molten agar (0.75%) in Dulbecco's modified Eagle's medium (DMEM). A non-limiting example of the set-up is shown in FIG. 3. Once the solution is gelled, the corneas are inverted so that the epithelial layer is accessible. Cultures are placed in 60-mm diameter pyrex tissue culture dishes. High glucose DMEM is prepared containing 13MEM-NEAA (minimal essential medium non-essential amino acids), 13 RMPI 1640 Vitamin Solution, 13 antibiotic/antimycotic, ascorbic acid (0.45 mM), and ciprofloxacin (101 g/ml). High glucose DMEM is added up to the scleral rims, leaving the corneas exposed to air. The dishes are placed in a 37° C. humidified incubator with 5% $CO_2$. The epithelium of each culture is moistened with 500 μL medium, added dropwise onto the central cornea every 7 to 9 hours. The vesicating agent, NM, is added dropwise onto the central cornea. Cornea samples (peeled off their agar support) are either put epithelial side down in cryomolds containing Optimal Cutting Temperature (OCT, Tissue-Tek; Sakura, Torrance, CA, USA) compound and flash frozen for histology and immunofluorescence, or directly snap frozen for further protein analyses including Western blot and ADAM17 activity assays (InnoZyme TACE activity assay kit; Calbiochem, Billerica, MA, USA).
NM is used to induce corneal injury. NM, in powdered solid form (catalog No. 122564; Sigma-Aldrich) is first dissolved in PBS to 100 mM, and then diluted with medium to 10 mM. Ten microliters are applied to deliver 100 nmol vesicant to the cornea. After applying NM onto the central corneas, the cultures are returned to the 37° C. incubator for 2 hours without removing the vesicant. After this incubation, contaminated medium is removed, and fresh medium is added to the central cornea until the level in the dish reached the top of the scleral rim. Control unexposed and exposed corneas are then returned to 37° C. for a 22-hour incubation, being removed for only three short periods to add 20 μL medium to the exposed samples not receiving N-Met-TTHX1114 therapy, or to add 20 μL of N-Met-TTHX1114 as therapy to the central corneas. The first -met-TTHX1114 application is left on for 8 hours, the second for 9 hours, and the third for 5 hours. Thus, the length of the 2-hour exposure and the subsequent treatment is 24 hours in total.

For experiments analyzing how fast NM exposure induced ADAM17, cultures are set up as described. For the shortest exposure time, the NM solution is applied to a cornea, then immediately washed off and the sample is put in protein isolation extraction buffer. This is repeated with two other corneas to collect three 0-minute exposures. For the 5- and 10-minute exposures, NM is added to the sets of three corneas accordingly, insuring none are accidentally under- or overexposed to NM. All corneas are extracted and processed for ADAM17 activity assays.

The InnoZyme ADAM17/TACE Activity Kit (Calbiochem) is used to quantify the enzyme's activity from corneal extracts according to the vendor's provided protocol. Briefly, 400 μL wash buffer (from the InnoZyme kit) is applied to 96-well plates precoated with anti-human ADAM17 antibody, followed by two washes. Triplicate samples of corneal extracts and InnoZyme kit standards (100 μL) are each added to three sets of wells. Plates are sealed and incubated 1 hour with gentle shaking at room temperature. Then, plates are washed with 400 μL wash buffer five times. ADAM17 substrate supplied in the kit (100 μL) is added to each well and incubated for 5 hours at 37° C. Fluorescence is measured at an excitation wavelength of 324 nm and an emission wavelength of 405 nm, and is reported as relative fluorescence units on graphs. For immunodetection of ADAM17, OCT-embedded sections on slides are first fixed in 20° C. methanol for 10 minutes. Nonspecific binding is blocked for 1 hour with 5% normal goat serum (NGS) in PBS with 0.05% Tween-20 (PBST). A mouse monoclonal antibody against the ectodomain (amino acids 18-671) of human ADAM 17 (5 μg/mL in 1.5% NGS, MAB9304; R&D Systems, Minneapolis, MN, USA), which is found to detect only the active enzyme by immunofluorescence, is applied to the slides for a 1-hour incubation at room temperature, then the slides are washed three times for 10 minutes in PBST. For negative control slides, the same volume of PBST is applied to sections as that of primary antibody used on test sections, followed by the same wash volume. Goat anti-mouse IgG conjugated to AlexaFluor488 (1:1000; Invitrogen, Carlsbad, CA, USA) in 1.5% NGS is applied for 1 hour at room-temperature incubation. After washing with PBST three times for 5 minutes, 0.4 mg/mL DAPI is applied to sections for 5 minutes to counterstain the nuclei. Prolong Gold is used in cover slipping the slides.
Results
Histopathology of NM Induced Injury in Corneal Organ Cultures
Injury inflicted by NM includes the following: (a) hyperplasia of the epithelial layer, which is apparent by the increase in the number and depth of epithelial cells pushing down into the stroma. This is referred to as downward hyperplasia. Unexposed (naïve) cornea shows some downward hyperplasia but it isn't as extensive as cornea exposed to NM; (b) basal cell nuclei rising up toward the top of the basal epithelial cells; and (c) epithelial-stromal separation. The histopathological effects are visible as early as four days post-exposure. An exemplary histopathological grading scheme for assessing the effects of NM induced corneal injury is shown in FIG. 6. Histopathological grading is improved by treatment with N-Met-TTHX1114. The N-Met-TTHX1114 treated corneal sections exhibit lower score (indicative of lesser injury) compared to sections from untreated corneas.

Treatment of NM Exposed Corneal Cells with N-Met-TTHX1114 Protects Against Injury Treatment of NM-exposed cornea with TTHX1114 protects the cornea from histopathological injury induced by NM. Following NM-exposure, the N-Met-TTHX1114 treated cornea does not exhibit downward hyperplasia. Further, epithelial-stromal separation is not visible in corneas treated with N-Met-TTHX1114.

NM Exposures Reduces FGF-1 Levels in Rabbit Cornea

Figure 9:
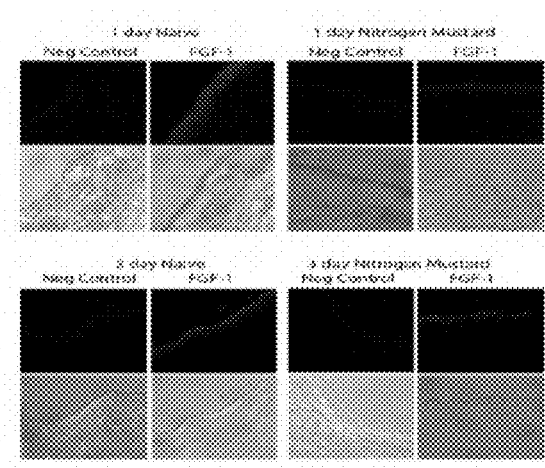
FIG. 9 demonstrates corneal levels of FGF-1 following exposure to a vesicant.

Rabbit corneal sections, exposed to NM, are incubated with anti-FGF-1 antibodies. In exposed corneas, a reduction of FGF-1 level is observed, as shown in FIG. 9. Corneal sections exposed to NM, 1 day (upper panel of FIG. 9), and 3 days (lower panel of FIG. 9) post-exposure, demonstrate enhanced suppression of FGF-1 compared to naïve corneal sections.

NM Exposures Induces ADAM17 Activation in Rabbit Cornea

In NM exposed corneas, intense fluorescent signal is observed at the basement membrane zone where the ADAM17 enzyme would need to be positioned in order to degrade collagen XVII ADAM17 is not appreciably detected in unexposed corneas.

N-Met-TTHX1114 Treatment Reduces NM Exposure Induced ADAM17 Activation in Rabbit Cornea Upon treatment of corneas with TTH1114, ADAM17 fluorescent signal is attenuated in peripheral and central cornea. The attenuation or lack of ADAM17 fluorescent signal corresponds with better histologic appearance of the corneal epithelial-stromal junction.

N-Met-TTHX1114 Treatment Ameliorates NM Exposure Induced Suppression of Corneal Epithelial Proliferation Peripheral corneal epithelial layer stimulation is assessed by via EdU incorporation of corneal epithelial cells (CECs). Primary cultures of rabbit CECs are established using standard procedures, e.g., the procedure described by Kay et al. (Kay et al. Investigative ophthalmology & visual science. 1993; 34(3):663-72; Lee et al., Investigative ophthalmology & visual science. 2009; 50(5):2067-76). The cells are exposed to NM for two hours. Proliferation assays are performed in 12-well plates using, e.g., a Click-IT assay kit (Life Technologies). Incorporation of EdU into corneal epithelial cells is an indicator of epithelial proliferation. The percentage corneal epithelial cells incorporating EdU are lower when treated with N-Met-TTHX1114, following NM-exposure, compared to untreated controls.

Example 4: Sulfur Mustard Induced Injury of Corneal Endothelial Cells

The study is directed towards the effect of modified FGF-1 polypeptides comprising the sequence of SEQ ID NO: 2 (N-Met-TTHX1114) on treatment of sulfur mustard (SM) induced corneal injury. The modified FGF-1 polypeptides are generated using methods as described above in the Recombinant Techniques section.

Experimental Methods

Rabbits are exposed to sulfur mustard in cohorts of 8 to 16 animals during a 4-month period. One day before exposure, a 4-in$^2$ region on each rabbit's back is clipped, and a fentanyl patch (25 µg/h) is placed anterior to the scapula. On the day of exposure, rabbits are anesthetized with an intramuscular administration of 15 mg/kg of ketamine and 7 mg/kg of xylazine, and physiological parameters are recorded. The corneas of anesthetized rabbits are exposed to SM vapor for 2.5 min. Two minutes after exposure, exposed eyes are gently rinsed with 10 mL sterile saline to flush residual agent.

A first group of rabbits are euthanized 24 hours after exposure. Five minutes after euthanasia, 20 µL of a 0.1 mg/mL solution of AlexaFluor 488 (Life Technologies, Carlsbad, CA) dissolved in PBS (pH 7.4) is injected into the anterior chamber through a 30-gauge needle using a 100-µL Hamilton glass syringe (Hamilton Company, Reno, NV). After 10 minutes, corneas are excised and washed three times for 1 minute in 10 mL PBS. Corneas are transferred to 14-mL round-bottom tubes (Becton Dickinson, Franklin Lakes, NJ) with 100 µL PBS and incubated on ice in the dark with gentle agitation. After 30 minutes, supernatant is diluted 1:5 in PBS and analyzed for fluorescence on a Synergy MX fluorophotometer (Biotek, Winooski, VT) using an excitation wavelength of 488±10 nm, emission wavelength of 524±10 nm, and a gain of 50. Representative corneas are imaged with a blue diode and FITC filter set in a Versadoc MP 4000 (Bio-Rad Laboratories, Hercules, CA).

The remaining rabbits are further divided into a test group, treated with N-Met-TTHX1114 at varying doses, and a sham control group, treated with control vehicle. The treatments are carried out for about two weeks. Rabbits are returned to cages and provided food and water ad libitum. Fentanyl patches are replaced after every 72 hours to manage discomfort through 6 days after the exposure and applied liberally thereafter as needed. Animals are monitored daily for signs of pain and distress. Corneal injury is clinically evaluated on a regular basis using pachymetry, fluorescein exclusion assays, and slit-lamp evaluations.

Results

Sulfur Mustard (SM) Exposure Causes Corneal Endothelial Injury

Corneas visualized at 370 nm by scanning electron microscopy (SEM) 24 hours after SM exposure exhibit a centripetal injury, with extensive loss of corneal endothelial cells (CECs) in the central cornea and increased retention toward the exposure margins. To obtain a more comprehensive overview of SM-induced changes in the corneal endothelium, the fine structure of the posterior cornea is evaluated by electron microscopy. Enface scanning electron micrographs of unexposed corneas reveals a continuous layer of polygonal cells of regular shape and size, with interdigitated borders, apical microvilli, and infrequent cilia. Within 24 hours of exposure, all corneal endothelia exhibit evidence of an acute lesion, with extensive central CEC loss and more diffuse vesication in the exposure penumbra. The CECs within the exposed region displays two general morphologies, namely, enlarged (highly attenuated) polymorphic cells and rounded or spindle-shaped cells. Most CECs exhibit atypical apical membrane morphologies and lack cell-to-cell interdigitations. In regions of CEC vesication, denuded Descemet's membrane (DM) is covered by a complex arbor of CEC lamellipodia and filopodia. The TEM imaging of corneal cross-sections confirmed the centripetal injury pattern, with CEC morphology progressively normalizing toward the injury margin. Denuded DM near the central lesion is infiltrated by extensively arborized cellular processes. At more distal regions, overlapping cellular processes with loss of junctional complexes is common, suggestive of a motile population. The rounded CEC population observed by SEM is found exclusively overlying polymorphic endothelium and display signs of necrosis or apoptosis.

Treatment with N-Met-TTHX1114 Resolves Corneal Endothelial Injuries

Eight weeks after exposure, endothelial cell morphology and structure are compared between test group (also referred to as resolved eyes) and sham control group (which later develops MGK). Resolved eyes are distinguished by the absence of characteristic MGK sequelae during clinical evaluations such as corneal erosions, neovascularization, or corneal haze and had corneal thicknesses that are statistically indistinguishable from sham-exposed controls by 6 weeks. Enface scanning micrographs of resolved eyes are found to be strikingly similar to sham-exposed controls, with a well-organized monolayer of polygonal cells. The average CEC size is increased in resolved eyes compared with control corneas; otherwise, resolved corneas do not exhibit significant variability across the posterior surface. In contrast, the sham-control treated rabbits with MGK endothelia reveal extensive variability in cell shape and cell size among animals, indicative of a dynamic injury process. Focal variability in endothelial morphology is routinely observed in individual corneas, with some regions exhibiting enlarged but mosaic CECs and other regions displaying significant disorganization, with variable degrees of apical blebbing, areas showing denuded DM, and clearly delineated cell boundaries lacking. These phenomena are not observed in the N-Met-TTHX1114 treated resolved endothelium. Transmission Electron Microscope images of N-Met-TTHX1114 treated resolved corneas are very similar to naïve endothelium. In contrast, sham-control treated endothelium with MGK pathology exhibit diffusive thickening of the posterior DM, consistent with either edema and/or the deposition of a retrocorneal fibrous membrane. The MGK corneas also exhibit extensive markers of CEC stress or injury, including cytoplasmic rarefication, excessive vacuolization, and swollen endoplasmic reticuli. There is a high frequency of overlapping cell processes, similar to 24-hour images and suggestive of an ongoing attempt to repopulate recently denuded DM.

Example 5: Modified FGF-1 (N-Met-TTHX1114) is Effective in Wound Healing

This study is directed towards the effect of a modified FGF-1 polypeptide comprising the sequence of SEQ ID NO: 2 (N-Met-TTHX1114) on rate of wound healing.

Experimental Methods

Female C57BL/Ks-db/db diabetic mice, 11 weeks old, are obtained from Jackson Laboratories, and housed in sterile microisolator boxes with sterile water and bedding and are kept in a semi-barrier quarantine facility.

Skin Organ Culture

Skin biopsy specimens from healing impaired mice are cultured in suitable culture medium. Briefly, tissue samples are incubated at 37° C. in DMEM (Gibco) medium supplemented with 0.25% heat-inactivated bovine serum (Gibco). The skin specimens are treated daily for 2 days or 3 days with 0, 1, 10, and 100 μg/mL N-Met-TTHX1114. The tissue samples are then labeled for 24 hours with 4 μCi of [methyl-$^3$H]thymidine (from a stock solution containing 20

Ci/mmol; New England Biolabs). After thymidine labeling, the skin specimens are washed, solubilized, and assayed for radioactivity count.

Wound-Closure Model

Mice are anesthetized with intraperitoneal injections of 110 mg ketamine and 9 mg xylazine per kg of body weight. The mid-back and thoracic skin is shaved and disinfected with a 2% chlorhexidine surgical scrub followed by a 70% ethanol.

A template 1.6 cm in diameter is used to mark a 2.0-cm$^2$ circle on the mid-dorsal area, and a single full-thickness wound is created by blunt excision with sterile curved iris scissors. Wound areas typically increase to approximately 2.3 cm$^2$ soon after injury, presumably because of contraction of the dermis along the wound perimeter. All surgical and subsequent healing analysis procedures are performed in a laminar flow hood using a full aseptic techniques. Filter-sterili zed growth factors, at varying doses, and corresponding vehicle control solutions are applied topically, on days 0, 3, and 7 after injury. The wounds are covered with a semi-transparent Bioclusive dressing for protection, maintenance of a moist environment, and prevention of crust formation. Wound fluid samples are taken at day 10 after injury and cultured for aerobic and anaerobic microorganisms. Animals from cultures that exhibit more than 50 colonies per wound are excluded from the study analysis. Prevention of even mild or subclinical infection results in a consistent maximal healing impairment, thus providing a large wound-healing window for evaluation of treatment effects.

Healing Analysis

Wound appearances are recorded photographically, and their perimeters are traced onto sterile glass slides applied directly to the exposed wound surfaces after prewetting with a drop of sterile physiologic saline.

Measurements are made immediately after wounding and twice weekly thereafter until the wounds are completely closed. Wound areas and perimeters are determined from the glass-slide tracings using suitable computerized image analysis (e.g., using Presage C V-6; Advanced Imaging Concepts, Princeton, NJ). Statistical significances of differences between groups are evaluated using an unpaired two-tailed Student t test. Healing expressed as a decrease in percent initial area is converted to linear ingrowth from the wound edges by dividing the difference in wound areas by the average wound perimeters at sequential time intervals. Total ingrowth at a specific time is the sum of the incremental ingrowth distances up until that time. This transformation linearizes closure as a function of time, thereby allowing expression of healing as kinetic rates that are constant over time. Wounds are considered fully healed when moist granulation tissue is no longer apparent, indicating a functional epidermal water-permeability barrier.

Results

Skin biopsy specimens, from the healing impaired mice, incorporates [methyl-$^3$H]thymidine in response to daily doses of N-Met-TTHX1114. The cells within the skin respond mitogenically to N-Met-TTHX1114 in a dose-dependent manner. Thus, N-Met-TTHX111 induces DNA synthesis in skin organ cultures.

Further, full-thickness dermal excisional wounds, about 1.6 cm in diameter, close substantially faster in responses of doses of N-Met-TTHX1114, applied during the first week following wound initiation, compared to treatment with control vehicle. Thus, N-Met-TTHX1114 accelerates wound closure.

Moreover, gross appearance and mean size of vehicle and N-Met-TTHX1114 treated wounds differ significantly. The N-Met-TTHX1114 treated wounds show signs of neovascularization, such as visible reddening and leakage of serous fluids, as early as 3 days following treatment. In contract, the wounds receiving control vehicle contain little or no visible serous fluids and substantially less apparent signs of neoangiogenesis.

Example 6: Treatment of Herpetic Keratopathy Using a Modified FGF-1 Polypeptides (N-Met-TTHX1114 or TTHX-1114)

This study is directed towards using a modified FGF-1 polypeptide comprising the sequence of SEQ ID NO: 2 (N-Met-TTHX1114) or SEQ ID NO: 205 (TTHX1001) for the treatment of herpetic keratopathy.

Methods

A group of patients with herpetic keratopathy is selected for this study. The patients are divided into three subgroups. Patients in the first sub-group are administered, ocularly, an ophthalmic formulation, such as an eye drop, containing about 500 µg/ml (i.e., 5 µg/ml) of N-met TTHX1114 (SEQ ID NO: 2) formulated in phosphate buffered saline (at pH 7.2), 0.3% propylene glycol, 0.4% polyethylene glycol 400, and 0.05% hydroxypropyl guar. Patients in the second sub-group are administered, ocularly, an ophthalmic formulation, such as an eye drop, containing about 500 pg/ml (i.e., 5 µg/ml) of TTHX1001 (SEQ ID NO: 205) formulated in phosphate buffered saline (at pH 7.2), 0.3% propylene glycol, 0.4% polyethylene glycol 400, and 0.05% hydroxypropyl guar. Patients in the third sub-group are administered, ocularly, a sham ophthalmic formulation that does not contain the N-Met-TTHX1114 (SEQ ID NO: 2) or the TTHX1001 (SEQ ID NO: 205) but is otherwise identical to what is administered to the first and the second sub-group. For all three subgroups, the eye drop is either self-administered by the patient or administered by a nurse or a caregiver. The N-Met-TTHX1114 (SEQ ID NO: 2) containing ophthalmic formulation, the TTHX1001 (SEQ ID NO: 205) containing ophthalmic formulation, and the sham ophthalmic formulation are administered, respectively to patients in the first, second, and the third sub-group, twice daily for up to 30 days.

Results

It is observed that the ophthalmic formulation containing the N-Met-TTHX1114 (SEQ ID NO: 2) and the ophthalmic formulation containing the TTHX1001 (SEQ ID NO: 205) results in healing of the herpetic corneal ulcer within about 14 days in majority of the patients belonging to the first and the second sub-groups, along with reduction in the duration of pain and inflammation. Furthermore, eyes of patients in the first and the second sub-groups, treated respectively with the N-Met-TTHX1114 (SEQ ID NO: 2) containing ophthalmic formulation and the TTHX1001 (SEQ ID NO: 205) containing ophthalmic formulation have less corneal haze and scarring than patients in the third sub-group, who were treated with the sham.

Example 7: Treatment of Chronic Herpetic Keratopathy Using a Modified FGF-1 Polypeptides (N-Met-TTHX1114 or TTHX-1001)

This study is directed towards using a modified FGF-1 polypeptide comprising the sequence of SEQ ID NO: 2 (N-Met-TTHX1114) or SEQ ID NO: 205 (TTHX1001) for the treatment of chronic herpetic keratopathy.

Methods

A group of patients with chronic herpetic keratopathy is selected for this study. The patients are divided into three subgroups. Patients in the first sub-group are administered, ocularly, an ophthalmic formulation, such as an eye drop, containing about 500 pg/ml (i.e., 5 µg/ml) of N-Met-TTHX1114 (SEQ ID NO: 2) formulated in phosphate buffered saline (at pH 7.2), 0.3% propylene glycol, 0.4% polyethylene glycol 400, and 0.05% hydroxypropyl guar. Patients in the second sub-group are administered, ocularly, an ophthalmic formulation, such as an eye drop, containing about 500 pg/ml (i.e., 5 µg/ml) of TTHX1001 (SEQ ID NO: 205) formulated in phosphate buffered saline (at pH 7.2), 0.3% propylene glycol, 0.4% polyethylene glycol 400, and 0.05% hydroxypropyl guar. Patients in the third sub-group are administered, ocularly, a sham ophthalmic formulation that does not contain the N-Met-TTHX1114 (SEQ ID NO: 2) or the TTHX1001 (SEQ ID NO: 205) but is otherwise identical to what is administered to the first and the second sub-group. For all three subgroups, the eye drop is either self-administered by the patient or administered by a nurse or a caregiver. The N-Met-TTHX1114 (SEQ ID NO: 2) containing ophthalmic formulation, the TTHX1001 (SEQ ID NO: 205) containing ophthalmic formulation, and the sham ophthalmic formulation are administered, respectively to patients in the first, second, and the third sub-group, twice daily for up to 30 days.

Results

It is observed that the ophthalmic formulation containing the N-Met-TTHX1114 (SEQ ID NO: 2) and the ophthalmic formulation containing the TTHX1001 (SEQ ID NO: 205) result in healing of corneal ulcer in majority of the patients belonging to the first and the second sub-groups, along with reduction in of pain and inflammation. Furthermore, eyes of patients in the first and the second sub-groups, treated respectively with the N-Met-TTHX1114 (SEQ ID NO: 2) containing ophthalmic formulation and the TTHX1001 (SEQ ID NO: 205) containing ophthalmic formulation, have less corneal opacity haze and scarring than patients in the third sub-group, who are treated with the sham.

Example 8: Treatment of Neurotrophic Keratopathy Using Modified FGF-1 Polypeptides (N-Met-TTHX1114 or TTHX-1001)

This study is directed towards using a modified FGF-1 polypeptide comprising the sequence of SEQ ID NO: 2 (N-Met-TTHX1114) or SEQ ID NO: 205 (TTHX1001) for the treatment of neurotrophic keratopathy secondary to herpes infection.

Methods

A group of patients with neurotrophic keratopathy is selected for this study. The patients are divided into three subgroups. Patients in the first sub-group are administered, ocularly, an ophthalmic formulation, such as an eye drop, containing about 500 pg/ml (i.e., 5 µg/ml) of N-Met-TTHX1114 (SEQ ID NO: 2) formulated in phosphate buffered saline (at pH 7.2), 0.3% propylene glycol, 0.4% polyethylene glycol 400, and 0.05% hydroxypropyl guar. Patients in the second sub-group are administered, ocularly, an ophthalmic formulation, such as an eye drop, containing about 500 pg/ml (i.e., 5 µg/ml) of TTHX1001 (SEQ ID NO: 205) formulated in phosphate buffered saline (at pH 7.2), 0.3% propylene glycol, 0.4% polyethylene glycol 400, and 0.05% hydroxypropyl guar. Patients in the third sub-group are administered, ocularly, a sham ophthalmic formulation that does not contain the N-Met-TTHX1114 (SEQ ID NO:

2) or the TTHX1001 (SEQ ID NO: 205) but is otherwise identical to what is administered to the first and the second sub-group. For all three subgroups, the eye drop is either self-administered by the patient or administered by a nurse or a caregiver. The N-Met-TTHX1114 (SEQ ID NO: 2) containing ophthalmic formulation, the TTHX1001 (SEQ ID NO: 205) containing ophthalmic formulation, and the sham ophthalmic formulation are administered, respectively to patients in the first, second, and the third sub-group, twice daily for up to 30 days.

Results

It is observed that the ophthalmic formulation containing the N-Met-TTHX1114 (SEQ ID NO: 2) and the ophthalmic formulation containing the TTHX1001 (SEQ ID NO: 205) result in healing of corneal ulcer in majority of the patients belonging to the first and the second sub-groups, along with reduction in of pain and inflammation. Furthermore, eyes of patients in the first and the second sub-groups, treated respectively with the N-Met-TTHX1114 (SEQ ID NO: 2) containing ophthalmic formulation and the TTHX1001 (SEQ ID NO: 205) containing ophthalmic formulation, have less corneal opacity haze and scarring than patients in the third sub-group, who are treated with the sham.

Example 9: Treatment of Recurrent Herpetic Keratopathy and the Suppression of Reactivation of Latent Virus Using Modified FGF-1 Polypeptides (N-Met-TTHX1114 or TTHX1001)

This study is directed towards using a modified FGF-1 polypeptides comprising the sequence of SEQ ID NO: 2 (N-Met-TTHX1114) or SEQ ID NO: 205 (TTHX1001) for the treatment of neurotrophic keratopathy secondary to herpes infection.

Methods

A group of patients with recurrent keratopathy is selected for this study. The patients have experienced at least one episode of herpetic keratopathy. For treatment of recurrent herpetic keratopathy and the suppression of reactivation of latent virus, the patients are divided into three subgroups. Patients in the first sub-group are administered, ocularly, an ophthalmic formulation, such as an eye drop, containing about 50 pg/ml to about 500 pg/ml (i.e., 5 µg/ml) of N-Met-TTHX1114 (SEQ ID NO: 2) formulated in phosphate buffered saline (at pH 7.2), 0.3% propylene glycol, 0.4% polyethylene glycol 400, and 0.05% hydroxypropyl guar. Patients in the second sub-group are administered, ocularly, an ophthalmic formulation, such as an eye drop, containing about 50 pg/ml to 500 pg/ml (i.e., 5 µg/ml) of TTHX1001 (SEQ ID NO: 205) formulated in phosphate buffered saline (at pH 7.2), 0.3% propylene glycol, 0.4% polyethylene glycol 400, and 0.05% hydroxypropyl guar. Patients in the third sub-group are administered, ocularly, a sham ophthalmic formulation that does not contain the N-Met-TTHX1114 (SEQ ID NO: 2) or the TTHX1001 (SEQ ID NO: 205) but is otherwise identical to what is administered to the first and the second sub-group. For all three subgroups, the eye drop is either self-administered by the patient or administered by a nurse or a caregiver. The N-Met-TTHX1114 (SEQ ID NO: 2) containing ophthalmic formulation, the TTHX1001 (SEQ ID NO: 205) containing ophthalmic formulation, and the sham ophthalmic formulation are administered, respectively to patients in the first, second, and the third sub-group, twice daily for up to 30 days.

Results

It is observed that the ophthalmic formulations containing the N-Met-TTHX1114 (SEQ ID NO: 2) and the ophthalmic formulation containing the TTHX1001 (SEQ ID NO: 205) increase the disease free interval and reduces the severity of the reactivated virus lesions, with patients receiving the modified FGF-1 having a longer period of time without recurrent disease than patients in the third sub-group, who are treated with the sham.

Example 10: Effects of Modified FGF-1 Polypeptides on Human Corneal Endothelial Cell (HCEC) Proliferation The study is directed towards modified FGF-1 polypeptides comprising the sequence of SEQ ID NO: 206 (TTHX1114) or SEQ ID NO: 205 (TTHX1001). The modified FGF-1 polypeptides are generated using methods as described above in the Recombinant Techniques section.

Experimental Methods and Results

Figure 2:
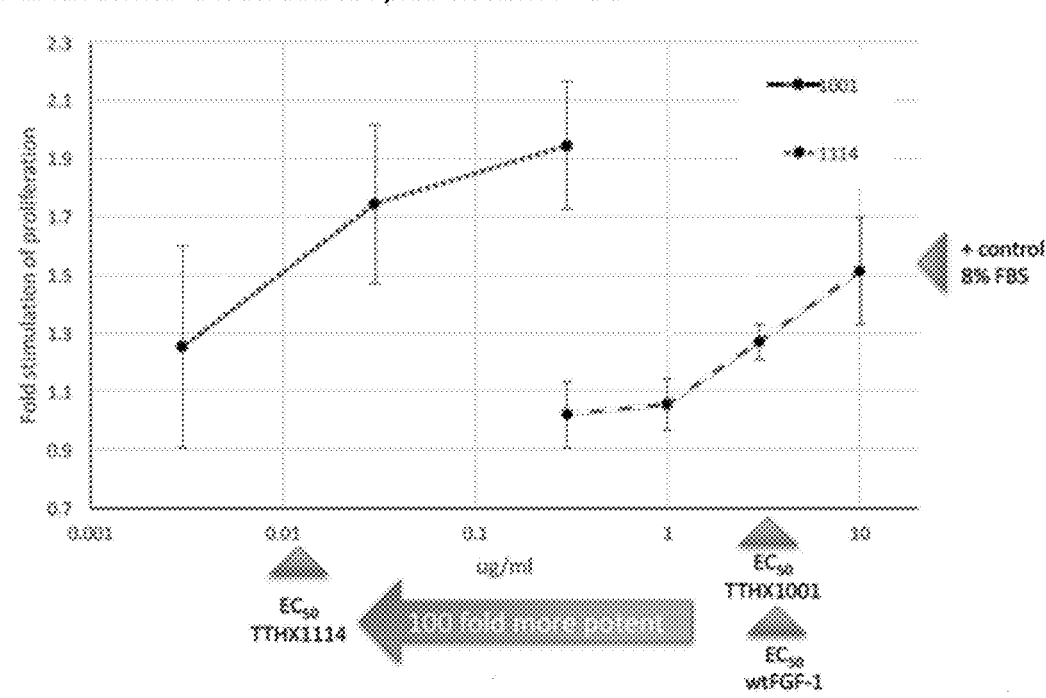
FIG. 2 illustrates the effect of exemplary modified FGF-1 polypeptides (TTHX1114 and TTHX1001) according to the present disclosure on the in vitro proliferation of human corneal endothelial cells. The dotted line corresponds to TTHX1114 and the dashed line corresponds to TTHX1001.

Primary cultures (passage 1) of human corneal endothelial cells from a healthy donor are seeded onto 24 well plates in the presence of fetal bovine serum (FBS, 8%) and 24 hours later treated with the varying concentrations of TTHX1114 (SEQ ID NO: 206), TTHX1001 (SEQ ID NO: 205), or wt-FGF-1 (SEQ ID NO: 1) in media with low (0.8%) FBS. The 8% FBS group serves as positive control. Results indicated that TTHX1114 was more potent than TTHX1001 or wt-FGF-1 in stimulating human corneal epithelial cell proliferation and was dose responsive therein. The $EC_{50}$ of TTHX1114 was about 100-fold lower than the wt-FGF-1 or the other tested modified FGF-1 polypeptide (TTHX1001; SEQ ID NO: 205), as illustrated in FIG. 2.

Example 11: Nitrogen Mustard Induced Injury of Cornea

The study is directed towards the effect of modified FGF-1 polypeptides comprising the sequence of SEQ ID NO: 206 (TTHX1114) on treatment of nitrogen mustard (NM) induced corneal injury. The modified FGF-1 polypeptides were generated using methods as described above in the Recombinant Techniques section.

Experimental Methods

A rabbit corneal organ culture model system was used to evaluate healing after exposure to NM. Rabbit eyes (8-12 weeks old) were obtained and corneas with 2-mm scleral rims were dissected from the eyes, placed epithelial-side down into a spot plate, and the concavities were filled with 558 C molten agar (0.75%) in Dulbecco's modified Eagle's medium (DMEM). A non-limiting example of the sett-up is shown in FIG. 3. Once the solution gelled, the corneas were inverted so that the epithelial layer was accessible. Cultures were placed in 60-mm diameter pyrex tissue culture dishes. High glucose DMEM was prepared containing 13MEM-NEAA (minimal essential medium non-essential amino acids), 13 RMPI 1640 Vitamin Solution, 13 antibiotic/antimycotic, ascorbic acid (0.45 mM), and ciprofloxacin (10 µg/ml). High glucose DMEM was added up to the scleral rims, leaving the corneas exposed to air. The dishes were placed in a 37° C. humidified incubator with 5% $CO_2$. The epithelium of each culture was moistened with 500 µL medium, added dropwise onto the central cornea every 7 to 9 hours. The vesicating agent, NM, was added dropwise onto the central cornea. Cornea samples (peeled off their agar support) were either put epithelial side down in cryo-molds containing Optimal Cutting Temperature (OCT, Tissue-Tek; Sakura, Torrance, CA, USA) compound and flash frozen for histology and immunofluorescence, or directly snap frozen for further protein analyses including Western blot and ADAM17 activity assays (InnoZyme TACE activity assay kit; Calbiochem, Billerica, MA, USA).

NM was used to induce corneal injury. NM, in powdered solid form (catalog No. 122564; Sigma-Aldrich) was first dissolved in PBS to 100 mM, and then diluted with medium to 10 mM. Ten microliters were applied to deliver 100 nmol vesicant to the cornea. After applying NM onto the central corneas, the cultures were returned to the 37° C. incubator for 2 hours without removing the vesicant. After this incubation, contaminated medium was removed, and fresh medium was added to the central cornea until the level in the dish reached the top of the scleral rim. Control unexposed and exposed corneas were then returned to 37° C. for a 22-hour incubation, being removed for only three short periods to add 20 μL medium to the exposed samples not receiving TTHX1114 therapy, or to add 20 μL of TTHX1114 as therapy to the central corneas. The first TTHX1114 application was left on for 8 hours, the second for 9 hours, and the third for 5 hours. Thus, the length of the 2-hour exposure and the subsequent treatment was 24 hours in total.

For experiments analyzing how fast NM exposure induced ADAM17, cultures were set up as described. For the shortest exposure time, the NM solution was applied to a cornea, then immediately washed off and the sample was put in protein isolation extraction buffer. This was repeated with two other corneas to collect three 0-minute exposures. For the 5- and 10-minute exposures, NM was added to the sets of three corneas accordingly, insuring none were accidentally under- or overexposed to NM. All corneas were extracted and processed for ADAM17 activity assays.

The InnoZyme ADAM17/TACE Activity Kit (Calbiochem) was used to quantify the enzyme's activity from corneal extracts according to the vendor's provided protocol. Briefly, 400 μL wash buffer (from the InnoZyme kit) was applied to 96-well plates precoated with anti-human ADAM17 antibody, followed by two washes. Triplicate samples of corneal extracts and InnoZyme kit standards (100 μL) were each added to three sets of wells. Plates were sealed and incubated 1 hour with gentle shaking at room temperature. Then, plates were washed with 400 μL wash buffer five times. ADAM17 substrate supplied in the kit (100 μL) was added to each well and incubated for 5 hours at 37° C. Fluorescence was measured at an excitation wavelength of 324 nm and an emission wavelength of 405 nm, and was reported as relative fluorescence units on graphs. For immunodetection of ADAM17, OCT-embedded sections on slides were first fixed in 208 C methanol for 10 minutes. Nonspecific binding was blocked for 1 hour with 5% normal goat serum (NGS) in PBS with 0.05% Tween-20 (PBST). A mouse monoclonal antibody against the ectodomain (amino acids 18-671) of human ADAM 17 (5 μg/mL in 1.5% NGS, MAB9304; R&D Systems, Minneapolis, MN, USA), which was found to detect only the active enzyme by immunofluorescence, was applied to the slides for a 1-hour incubation at room temperature, then the slides were washed three times for 10 minutes in PBST. For negative control slides, the same volume of PBST was applied to sections as that of primary antibody used on test sections, followed by the same wash volume. Goat anti-mouse IgG conjugated to AlexaFluor488 (1:1000; Invitrogen, Carlsbad, CA, USA) in 1.5% NGS was applied for 1 hour at room-temperature incubation. After washing with PBST three times for 5 minutes, 0.4 mg/mL DAPI was applied to sections for 5 minutes to counterstain the nuclei. Prolong Gold was used in cover slipping the slides.

Results

Histopathology of NM Induced Injury in Corneal Organ Cultures

Figure 4:
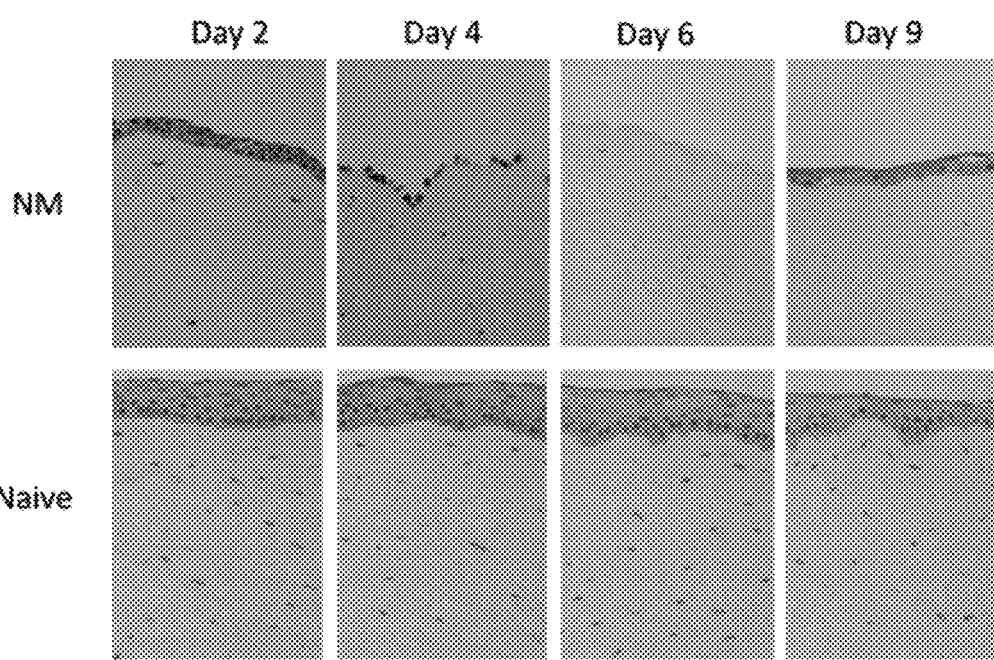
FIG. 4 shows a time course for vesicant injury to the cornea.

Injury inflicted by NM included the following: (a) hyperplasia of the epithelial layer, which was apparent by the increase in the number and depth of epithelial cells pushing down into the stroma. This is referred to as downward hyperplasia. Unexposed (naïve) cornea (FIG. 4, lower panel) also showed some downward hyperplasia but it wasn't as extensive as cornea exposed to NM (FIG. 4, upper panel); (b) basal cell nuclei rising up toward the top of the basal epithelial cells; and (c) epithelial-stromal separation. The histopathological effects were visible as early as four days post-exposure.

Figure 7:
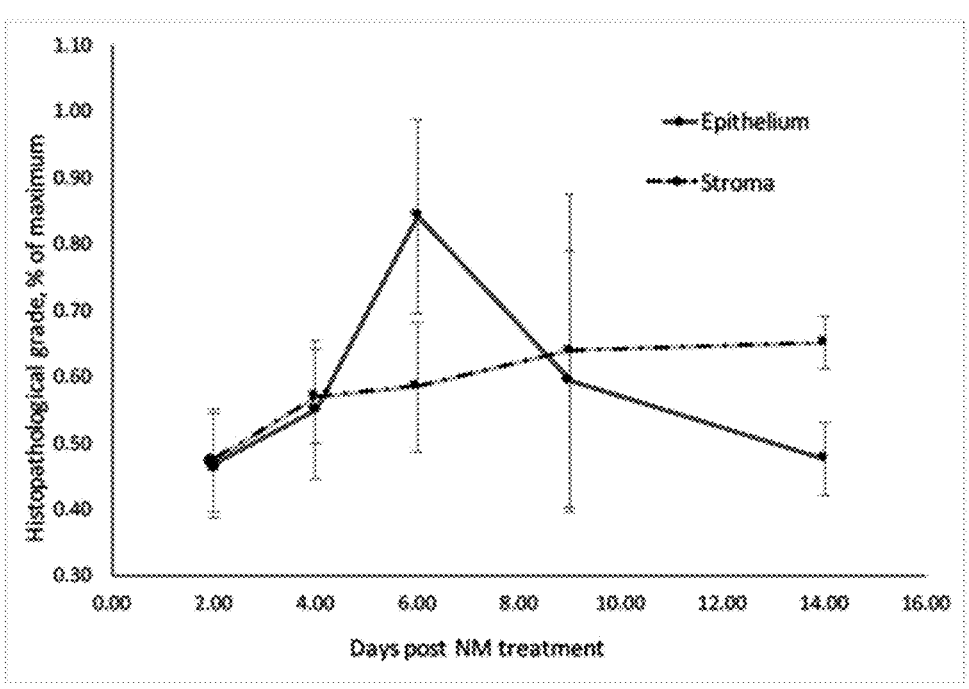
FIG. 7 shows histopathological grading of corneal and stromal injury upon vesicant exposure. The continuous like corresponds to "Epithelium," and the dashed line corresponds to "Stroma."

An exemplary histopathological grading scheme for assessing the effects of NM induced corneal injury is shown in FIG. 6, and NM induced histopathological grading of corneal and stromal injuries is also illustrated in the plot of FIG. 7.

Treatment of NM Exposed Corneal Cells with TTHX1114 Protects Against Injury

Figure 5:
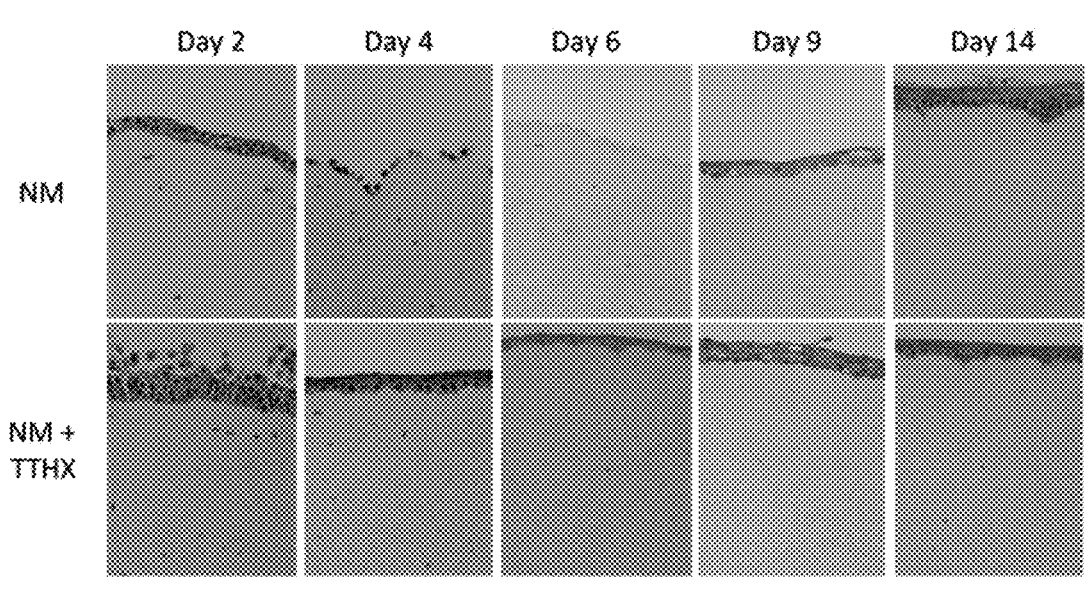
FIG. 5 illustrates the effect of treatment with an exemplary modified FGF-1 polypeptide (TTHX114), upon vesicant induced injury, assessed by histopathological staining.

Treatment of NM-exposed cornea with TTHX1114 protected the cornea from histopathological injury induced by NM. As seen in FIG. 5, on day 4 following NM-exposure, the TTHX1114 treated cornea did not exhibit downward hyperplasia (compare upper and lower panels of FIG. 5). Further, epithelial-stromal separation, as seen in upper panel of FIG. 4, was not visible in corneas treated with TTHX1114 (day 6, lower panel, FIG. 5).

Figure 8:
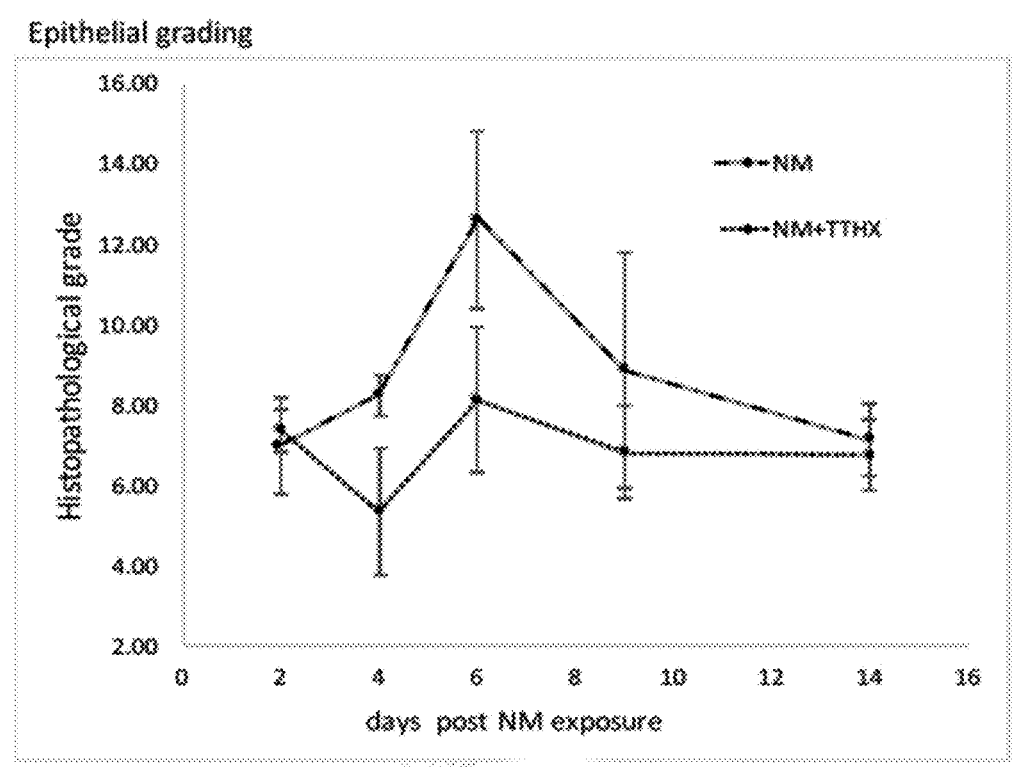
FIG. 8 shows reduced histopathological grading of vesicant injury in corneal cells treated with an exemplary modified FGF-1 polypeptide (TTHX1114). The dashed line corresponds to "NM" and the dotted line corresponds to "NM+TTHX."

Histopathological grading of NM induced injury was also found to be reduced in corneas treated with TTHX1114. The results are shown in FIG. 8.

TTHX1114 Protects NM Exposures Reduces FGF-1 Levels in Rabbit Cornea

Rabbit corneal sections, exposed to NM, were incubated with anti-FGF-1 antibodies. In exposed corneas, a reduction of FGF-1 level was observed, as shown in FIG. 9. Corneal sections exposed to NM, 1 day (upper panel of FIG. 9), and 3 days (lower panel of FIG. 9) post-exposure, demonstrated enhanced suppression of FGF-1 compared to naïve corneal sections.

NM Exposures Induces ADAM17 Activation in Rabbit Cornea

Figure 10A:
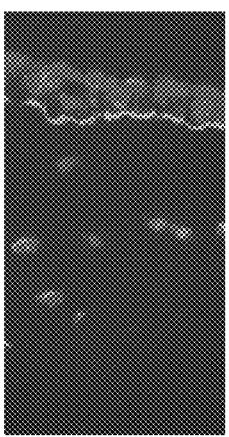
FIG. 10A and FIG. 10B illustrate the suppression of ADAM17 activation in corneal cells treated with an exemplary modified FGF-1 polypeptide (TTHX1114) after exposure to a vesicant.
Figure 10B:
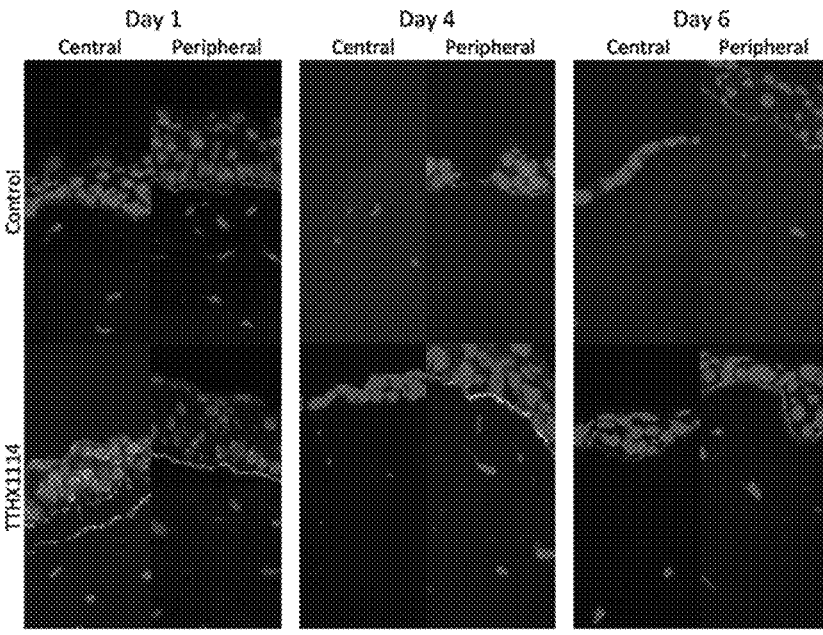

In NM exposed corneas, intense fluorescent signal was observed at the basement membrane zone where the ADAM17 enzyme would need to be positioned in order to degrade collagen XVII (upper panel of FIG. 10B showing ADAM17 immunofluorescence results on days 1, 4, and 6 post-exposure). ADAM17 was not appreciably detected in unexposed corneas (FIG. 10A).

TTHX1114 Treatment Reduces NM Exposure Induced ADAM17 Activation in Rabbit Cornea Upon treatment of corneas with TTH1114, ADAM17 fluorescent signal was attenuated in peripheral and central cornea (lower panel FIG. 10B). The attenuation or lack of ADAM17 fluorescent signal corresponded with better histologic appearance of the corneal epithelial-stromal junction.

Figure 11:
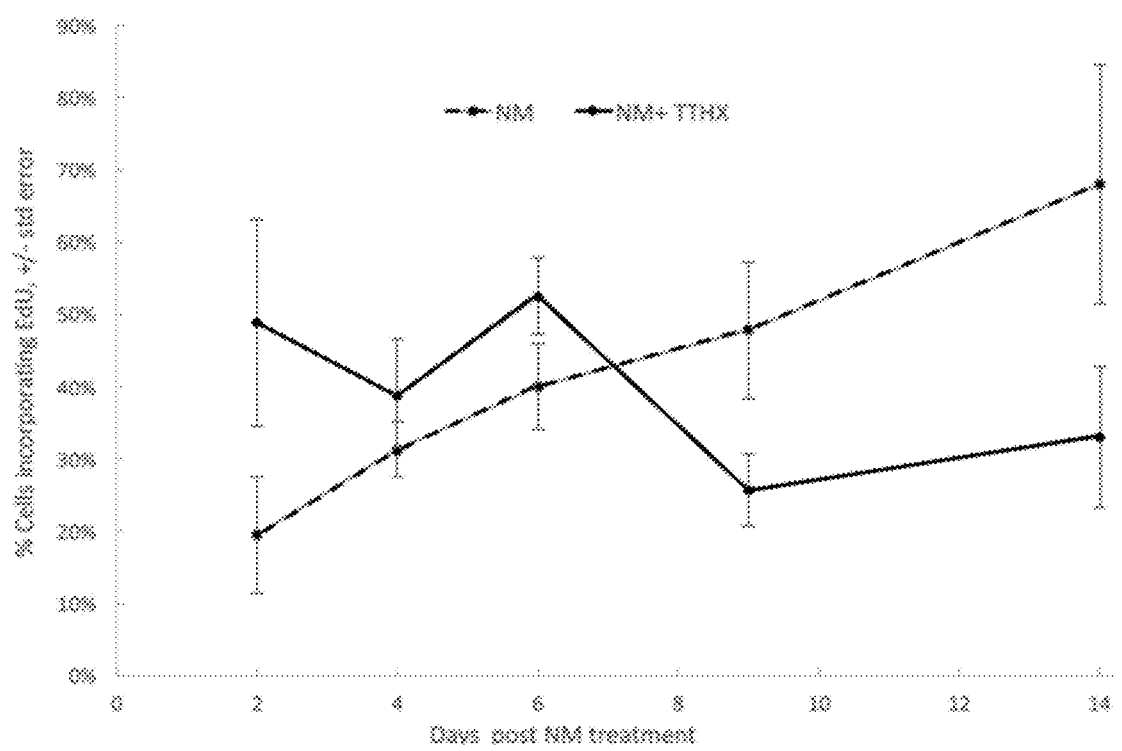
FIG. 11 illustrates the proliferation of corneal epithelial cells exposed to a vesicant and treated with an exemplary modified FGF-1 polypeptide (TTHX1114), measured by EdU incorporation. The dashed line corresponds to "NM" and the solid line corresponds to "NM+TTHX."

TTHX1114 Treatment Ameliorates NM Exposure Induced Suppression of Corneal Epithelial Proliferation Peripheral corneal epithelial layer was stimulation was assessed by via EdU incorporation of corneal epithelial cells (CECs). Primary cultures of rabbit CECs were established using standard procedures, e.g., the procedure described by Kay et al. (Kay et al. Investigative ophthalmology & visual science. 1993; 34(3):663-72; Lee et al., Investigative ophthalmology & visual science. 2009; 50(5):2067-76). The cells are exposed to NM for two hours. Proliferation assays were performed in 12-well plates using, e.g., a Click-IT assay kit (Life Technologies). Incorporation of EdU into corneal epithelial cells were assessed as an indicator of epithelial proliferation. The percentage corneal epithelial cells incorporating EdU were lower when treated with TTHX1114, following NM-exposure, as seen in FIG. 11.

Example 12: Sulfur Mustard Induced Injury of Corneal Endothelial Cells

The study is directed towards the effect of modified FGF-1 polypeptides comprising the sequence of SEQ ID NO: 206 (TTHX1114) on treatment of sulfur mustard (SM) induced corneal injury. The modified FGF-1 polypeptides are generated using methods as described above in the Recombinant Techniques section.

Experimental Methods

Rabbits are exposed in cohorts of 8 to 16 animals during a 4-month period. One day before exposure, a 4-in$^2$ region on each rabbit's back is clipped, and a fentanyl patch (25 μg/h) is placed anterior to the scapula. On the day of exposure, rabbits are anesthetized with an intramuscular administration of 15 mg/kg of ketamine and 7 mg/kg of xylazine, and physiological parameters are recorded. The corneas of anesthetized rabbits are exposed to SM vapor for 2.5 min using a vapor cup delivery system as previously described. Two minutes after exposure, exposed eyes are gently rinsed with 10 mL sterile saline to flush residual agent.

A first group of rabbits are euthanized 24 hours after exposure. Five minutes after euthanasia, 20 μL of a 0.1 mg/mL solution of AlexaFluor 488 (Life Technologies, Carlsbad, CA) dissolved in PBS (pH 7.4) is injected into the anterior chamber through a 30-gauge needle using a 100-μL Hamilton glass syringe (Hamilton Company, Reno, NV). After 10 minutes, corneas are excised and washed three times for 1 minute in 10 mL PBS. Corneas are transferred to 14-mL round-bottom tubes (Becton Dickinson, Franklin Lakes, NJ) with 100 μL PBS and incubated on ice in the dark with gentle agitation. After 30 minutes, supernatant is diluted 1:5 in PBS and analyzed for fluorescence on a Synergy MX fluorophotometer (Biotek, Winooski, VT) using an excitation wavelength of 488±10 nm, emission wavelength of 524±10 nm, and a gain of 50. Representative corneas are imaged with a blue diode and FITC filter set in a Versadoc MP 4000 (Bio-Rad Laboratories, Hercules, CA).

The remaining rabbits are further divided into a test group, treated with TTHX1114 at varying doses, and a sham control group, treated with control vehicle. The treatments are carried out for about two weeks. Rabbits are returned to cages and provided food and water ad libitum. Fentanyl patches are replaced after every 72 hours to manage discomfort through 6 days after the exposure and applied liberally thereafter as needed. Animals are monitored daily for signs of pain and distress. Corneal injury is clinically evaluated on a regular basis using pachymetry, fluorescein exclusion assays, and slit-lamp evaluations.

Results

Sulfur Mustard (SM) Exposure Causes Corneal Endothelial Injury

Corneas visualized at 370 nm by SEM 24 hours after SM exposure exhibit a centripetal injury, with extensive loss of corneal endothelial cells (CECs) in the central cornea and increased retention toward the exposure margins. To obtain a more comprehensive overview of SM-induced changes in the corneal endothelium, the fine structure of the posterior cornea is evaluated by electron microscopy. Enface scanning electron micrographs of sham-exposed corneas reveals a continuous layer of polygonal cells of regular shape and size, with interdigitated borders, apical microvilli, and infrequent cilia. Within 24 hours of exposure, all corneal endothelia exhibit evidence of an acute lesion, with extensive central CEC loss and more diffuse vesication in the exposure penumbra. The CECs within the exposed region displayed two general morphologies, namely, enlarged (highly attenuated) polymorphic cells and rounded or spindle-shaped cells. Most CECs exhibit atypical apical membrane morphologies and lack cell-to-cell interdigitations. In regions of CEC vesication, denuded Descemet's membrane (DM) is covered by a complex arbor of CEC lamellipodia and filopodia. The TEM imaging of corneal cross-sections confirmed the centripetal injury pattern, with CEC morphology progressively normalizing toward the injury margin. Denuded DM near the central lesion is infiltrated by extensively arborized cellular processes. At more distal regions, overlapping cellular processes with loss of junctional complexes is common, suggestive of a motile population. The rounded CEC population observed by SEM is found exclusively overlying polymorphic endothelium and display signs of necrosis or apoptosis.

Treatment with TTHX1114 Resolves Corneal Endothelial Injuries

Eight weeks after exposure, endothelial cell morphology and structure are compared between test group (also referred to as resolved) and sham control group (which later develops MGK). Resolved eyes are distinguished by the absence of characteristic MGK sequelae during clinical evaluations such as corneal erosions, neovascularization, or corneal haze and had corneal thicknesses that are statistically indistinguishable from sham-exposed controls by 6 weeks. Enface scanning micrographs of resolved eyes are found to be strikingly similar to sham-exposed controls, with a well-organized monolayer of polygonal cells. The average CEC size is increased in resolved eyes compared with control corneas; otherwise, resolved corneas do not exhibit significant variability across the posterior surface. In contrast, the sham-control treated rabbits with MGK endothelia reveal extensive variability in cell shape and cell size among animals, indicative of a dynamic injury process. Focal variability in endothelial morphology is routinely observed in individual corneas, with some regions exhibiting enlarged but mosaic CECs and other regions displaying significant disorganization, with variable degrees of apical blebbing, areas showing denuded DM, and clearly delineated cell boundaries lacking. These phenomena are not observed in the TTHX1114 treated resolved enodthelium. Transmission Electron Microscope images of TTHX1114 treated resolved corneas is very similar to naïve endothelium. In contrast, sham-control treated endothelium with MGK pathology exhibit diffusive thickening of the posterior DM, consistent with either edema and/or the deposition of a retrocorneal fibrous membrane. The MGK corneas also exhibit extensive markers of CEC stress or injury, including cytoplasmic rarefication, excessive vacuolization, and swollen endoplasmic reticuli. There is a high frequency of overlapping cell processes, similar to 24-hour images and suggestive of an ongoing attempt to repopulate recently denuded DM.

Example 13: Treatment of Herpetic Keratopathy Using a Modified FGF-1 Polypeptide (TTHX1114)

This study is directed towards using a modified FGF-1 polypeptide comprising the sequence of SEQ ID NO: 206 (TTHX1114) for the treatment of herpetic keratopathy.

Methods

A group of patients with herpetic keratopathy is selected for this study. The patients are divided into two subgroups. Patients in the first sub-group are administered, ocularly, an ophthalmic formulation, such as an eye drop, containing about 500 μg/ml (i.e., 5 μg/ml) of TTHX1114 (SEQ ID NO: 206) formulated in phosphate buffered saline (at pH 7.2), 0.3% propylene glycol, 0.4% polyethylene glycol 400, and 0.05% hydroxypropyl guar. Patients in the second sub-group are administered, ocularly, a sham ophthalmic formulation that does not contain the TTHX1114 (SEQ ID NO: 206) but is otherwise identical to what is administered to the first and the second sub-group. For both subgroups, the eye drop is either self-administered by the patient or administered by a nurse or a caregiver. The TTHX1114 (SEQ ID NO: 206) containing ophthalmic formulation and the sham ophthalmic formulation are administered, respectively to patients in the first and second sub-groups, twice daily for up to 30 days.

Results

It is observed that the ophthalmic formulation containing the TTHX1114 (SEQ ID NO: 206) results in healing of the herpetic corneal ulcer within about 14 days in majority of the patients belonging to the first sub-group, along with reduction in the duration of pain and inflammation. Furthermore, eyes of patients in the first sub-group, treated with the TTHX1114 (SEQ ID NO: 206) containing ophthalmic formulation have less corneal haze and scarring than patients in the third sub-group, who were treated with the sham.

Example 14: Treatment of Chronic Herpetic Keratopathy Using a Modified FGF-1 Polypeptide (TTHX1114)

This study is directed towards using a modified FGF-1 polypeptide comprising the sequence of SEQ ID NO: 206 (TTHX1114).

Methods

A group of patients with chronic herpetic keratopathy is selected for this study. The patients are divided into two subgroups. Patients in the first sub-group are administered, ocularly, an ophthalmic formulation, such as an eye drop, containing about 500 pg/ml (i.e., 5 μg/ml) of N-Met-TTHX1114 (SEQ ID NO: 2) formulated in phosphate buffered saline (at pH 7.2), 0.3% propylene glycol, 0.4% polyethylene glycol 400, and 0.05% hydroxypropyl guar. Patients in the second sub-group are administered, ocularly, a sham ophthalmic formulation that does not contain the TTHX1114 (SEQ ID NO: 206) but is otherwise identical to what is administered to the first and the second sub-group. For both subgroups, the eye drop is either self-administered by the patient or administered by a nurse or a caregiver. The TTHX1114 (SEQ ID NO: 206) containing ophthalmic formulation and the sham ophthalmic formulation are administered, respectively to patients in the first and second sub-group, twice daily for up to 30 days.

Results

It is observed that the ophthalmic formulation containing the TTHX1114 (SEQ ID NO: 206) result in healing of corneal ulcer in majority of the patients belonging to the first sub-group, along with reduction in of pain and inflammation. Furthermore, eyes of patients in the first sub-groups, treated with the TTHX1114 (SEQ ID NO: 206) containing ophthalmic formulation have less corneal opacity haze and scarring than patients in the third sub-group, who are treated with the sham.

Example 15: Treatment of Neurotrophic Keratopathy Using a Modified FGF-1 Polypeptide (TTHX1114)

This study is directed towards using a modified FGF-1 polypeptide comprising the sequence of SEQ ID NO: 206 (TTHX1114) for the treatment of neurotrophic keratopathy secondary to herpes infection.

Methods

A group of patients with neurotrophic keratopathy is selected for this study. The patients are divided into two subgroups. Patients in the first sub-group are administered, ocularly, an ophthalmic formulation, such as an eye drop, containing about 500 pg/ml (i.e., 5 μg/ml) of TTHX1114 (SEQ ID NO: 206) formulated in phosphate buffered saline (at pH 7.2), 0.3% propylene glycol, 0.4% polyethylene glycol 400, and 0.05% hydroxypropyl guar. Patients in the second sub-group are administered, ocularly, a sham ophthalmic formulation that does not contain the TTHX1114 (SEQ ID NO: 206) but is otherwise identical to what is administered to the first sub-group. For both subgroups, the eye drop is either self-administered by the patient or administered by a nurse or a caregiver. The TTHX1114 (SEQ ID NO: 206) containing ophthalmic formulation and the sham ophthalmic formulation are administered, respectively to patients in the first and the second sub-group, twice daily for up to 30 days.

Results

It is observed that the ophthalmic formulation containing the TTHX1114 (SEQ ID NO: 206) results in healing of corneal ulcer in majority of the patients belonging to the first sub-group, along with reduction in of pain and inflammation. Furthermore, eyes of patients in the first sub-group, treated respectively with the TTHX1114 (SEQ ID NO: 206) containing ophthalmic formulation, have less corneal opacity haze and scarring than patients in the third sub-group, who are treated with the sham.

Example 16: Treatment of Recurrent Herpetic Keratopathy and the Suppression of Reactivation of Latent Virus Using a Modified FGF-1 Polypeptide (TTHX1114)

This study is directed towards using a modified FGF-1 polypeptides comprising the sequence of SEQ ID NO: 206 (TTHX1114) for the treatment of neurotrophic keratopathy secondary to herpes infection.

Methods

A group of patients with recurrent keratopathy is selected for this study. The patients have experienced at least one episode of herpetic keratopathy. For treatment of recurrent herpetic keratopathy and the suppression of reactivation of latent virus, the patients are divided into two subgroups. Patients in the first sub-group are administered, ocularly, an ophthalmic formulation, such as an eye drop, containing about 50 pg/ml to about 500 pg/ml (i.e., 5 μg/ml) of TTHX1114 (SEQ ID NO: 206) formulated in phosphate buffered saline (at pH 7.2), 0.3% propylene glycol, 0.4% polyethylene glycol 400, and 0.05% hydroxypropyl guar. Patients in the third sub-group are administered, ocularly, a sham ophthalmic formulation that does not contain the TTHX1114 (SEQ ID NO: 206) but is otherwise identical to what is administered to the first and the second sub-group. For both subgroups, the eye drop is either self-administered by the patient or administered by a nurse or a caregiver. The TTHX1114 (SEQ ID NO: 206) containing ophthalmic formulation and the sham ophthalmic formulation are administered, respectively to patients in the first and the second sub-group, twice daily for up to 30 days.

Results

It is observed that the ophthalmic formulation containing the TTHX1114 (SEQ ID NO: 206) increases the disease free interval and reduces the severity of the reactivated virus lesions, with patients receiving the modified FGF-1 having a longer period of time without recurrent disease than patients in the second sub-group, who are treated with the sham.

| SEQUENCES | |
|---|---|
| SEQUENCE | No. |
| FNLPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 1 |
| MFNLPPGNYKKPKLLYSSNGGHFLRILPDGTVDGTRDRSDQHIQLQLSAESVGEVYIKSTETGQYLCMD TDGLLYGSQTPNEECLFLERLEENHYNTYISKKHAEKNWFVGLKKNGSVKRGPRTHYGQKAILFLPLPV SSD | 2 |
| MAEGEITTFTALTEK | 3 |
| ALTEK | 4 |
| LTEK | 5 |
| TEK | 6 |
| EK | 7 |
| K | 8 |
| MALTEKFNLPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 9 |
| MLTEKFNLPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 10 |
| MTEKFNLPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 11 |
| MEKFNLPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 12 |
| MKFNLPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 13 |
| MALTEKFNLPPGNYKKPKLLYSSNGGHFLRILPDGTVDGTRDRSDQHIQLQLSAESVGEVYIKSTETGQ YLCMDTDGLLYGSQTPNEECLFLERLEENHYNTYISKKHAEKNWFVGLKKNGSVKRGPRTHYGQKAILF LPLPVSSD | 14 |
| MLTEKFNLPPGNYKKPKLLYSSNGGHFLRILPDGTVDGTRDRSDQHIQLQLSAESVGEVYIKSTETGQY LCMDTDGLLYGSQTPNEECLFLERLEENHYNTYISKKHAEKNWFVGLKKNGSVKRGPRTHYGQKAILFL PLPVSSD | 15 |
| MTEKFNLPPGNYKKPKLLYSSNGGHFLRILPDGTVDGTRDRSDQHIQLQLSAESVGEVYIKSTETGQYL CMDTDGLLYGSQTPNEECLFLERLEENHYNTYISKKHAEKNWFVGLKKNGSVKRGPRTHYGQKAILFLP LPVSSD | 16 |
| MEKFNLPPGNYKKPKLLYSSNGGHFLRILPDGTVDGTRDRSDQHIQLQLSAESVGEVYIKSTETGQYLC MDTDGLLYGSQTPNEECLFLERLEENHYNTYISKKHAEKNWFVGLKKNGSVKRGPRTHYGQKAILFLPL PVSSD | 17 |
| MKENLPPGNYKKPKLLYSSNGGHFLRILPDGTVDGTRDRSDQHIQLQLSAESVGEVYIKSTETGQYLCM DTDGLLYGSQTPNEECLFLERLEENHYNTYISKKHAEKNWFVGLKKNGSVKRGPRTHYGQKAILFLPLP VSSD | 18 |
| ALTEKENLPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 19 |
| LTEKENLPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 20 |

-continued

| SEQUENCES | |
|---|---|
| SEQUENCE | No. |
| TEKENLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 21 |
| EKENLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 22 |
| KENLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 23 |
| ALTEKENLPPGNYKKPKLLYSSNGGHFLRILPDGTVDGTRDRSDQHIQLQLSAESVGEVYIKSTETGQY<br>LCMDTDGLLYGSQTPNEECLFLERLEENHYNTYISKKHAEKNWFVGLKKNGSVKRGPRTHYGQKAILFL<br>PLPVSSD | 24 |
| LTEKENLPPGNYKKPKLLYSSNGGHFLRILPDGTVDGTRDRSDQHIQLQLSAESVGEVYIKSTETGQYL<br>CMDTDGLLYGSQTPNEECLFLERLEENHYNTYISKKHAEKNWFVGLKKNGSVKRGPRTHYGQKAILFLP<br>LPVSSD | 25 |
| TEKENLPPGNYKKPKLLYSSNGGHFLRILPDGTVDGTRDRSDQHIQLQLSAESVGEVYIKSTETGQYLC<br>MDTDGLLYGSQTPNEECLFLERLEENHYNTYISKKHAEKNWFVGLKKNGSVKRGPRTHYGQKAILFLPL<br>PVSSD | 26 |
| EKENLPPGNYKKPKLLYSSNGGHFLRILPDGTVDGTRDRSDQHIQLQLSAESVGEVYIKSTETGQYLCM<br>DTDGLLYGSQTPNEECLFLERLEENHYNTYISKKHAEKNWFVGLKKNGSVKRGPRTHYGQKAILFLPLP<br>VSSD | 27 |
| KENLPPGNYKKPKLLYSSNGGHFLRILPDGTVDGTRDRSDQHIQLQLSAESVGEVYIKSTETGQYLCMD<br>TDGLLYGSQTPNEECLFLERLEENHYNTYISKKHAEKNWFVGLKKNGSVKRGPRTHYGQKAILFLPLPV<br>SSD | 28 |
| NLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 29 |
| LPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 30 |
| PPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 31 |
| PGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 32 |
| NLPPGNYKKPKLLYSSNGGHFLRILPDGTVDGTRDRSDQHIQLQLSAESVGEVYIKSTETGQYLCMDTD<br>GLLYGSQTPNEECLFLERLEENHYNTYISKKHAEKNWFVGLKKNGSVKRGPRTHYGQKAILFLPLPVSS<br>D | 33 |
| LPPGNYKKPKLLYSSNGGHFLRILPDGTVDGTRDRSDQHIQLQLSAESVGEVYIKSTETGQYLCMDTDG<br>LLYGSQTPNEECLFLERLEENHYNTYISKKHAEKNWFVGLKKNGSVKRGPRTHYGQKAILFLPLPVSSD | 34 |
| PPGNYKKPKLLYSSNGGHFLRILPDGTVDGTRDRSDQHIQLQLSAESVGEVYIKSTETGQYLCMDTDGL<br>LYGSQTPNEECLFLERLEENHYNTYISKKHAEKNWFVGLKKNGSVKRGPRTHYGQKAILFLPLPVSSD | 35 |
| PGNYKKPKLLYSSNGGHFLRILPDGTVDGTRDRSDQHIQLQLSAESVGEVYIKSTETGQYLCMDTDGLL<br>YGSQTPNEECLFLERLEENHYNTYISKKHAEKNWFVGLKKNGSVKRGPRTHYGQKAILFLPLPVSSD | 36 |
| MNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 37 |
| MLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 38 |
| MPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 39 |

-continued

| SEQUENCES | |
|---|---|
| SEQUENCE | No. |
| MPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 40 |
| MNLPPGNYKKPKLLYSSNGGHFLRILPDGTVDGTRDRSDQHIQLQLSAESVGEVYIKSTETGQYLCMDT<br>DGLLYGSQTPNEECLFLERLEENHYNTYISKKHAEKNWFVGLKKNGSVKRGPRTHYGQKAILFLPLPVS<br>SD | 41 |
| MLPPGNYKKPKLLYSSNGGHFLRILPDGTVDGTRDRSDQHIQLQLSAESVGEVYIKSTETGQYLCMDTD<br>GLLYGSQTPNEECLFLERLEENHYNTYISKKHAEKNWFVGLKKNGSVKRGPRTHYGQKAILFLPLPVSS<br>D | 42 |
| MPPGNYKKPKLLYSSNGGHFLRILPDGTVDGTRDRSDQHIQLQLSAESVGEVYIKSTETGQYLCMDTDG<br>LLYGSQTPNEECLFLERLEENHYNTYISKKHAEKNWFVGLKKNGSVKRGPRTHYGQKAILFLPLPVSSD | 43 |
| MPGNYKKPKLLYSSNGGHFLRILPDGTVDGTRDRSDQHIQLQLSAESVGEVYIKSTETGQYLCMDTDGL<br>LYGSQTPNEECLFLERLEENHYNTYISKKHAEKNWFVGLKKNGSVKRGPRTHYGQKAILFLPLPVSSD | 44 |
| MALTEKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 45 |
| MALTEKLPPGNYKKPKLLYSSNGGHFLRILPDGTVDGTRDRSDQHIQLQLSAESVGEVYIKSTETGQYL<br>CMDTDGLLYGSQTPNEECLFLERLEENHYNTYISKKHAEKNWFVGLKKNGSVKRGPRTHYGQKAILFLP<br>LPVSSD | 46 |
| MALTEKPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 47 |
| MALTEKPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 48 |
| MLTEKFNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 49 |
| MLTEKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 50 |
| MLTEKLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 51 |
| MLTEKPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 52 |
| MLTEKPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 53 |
| MTEKFNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 54 |
| MTEKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 55 |
| MTEKLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 56 |
| MTEKPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 57 |
| MTEKPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 58 |

| SEQUENCES | |
|---|---|
| SEQUENCE | No. |
| MEKFNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 59 |
| MEKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 60 |
| MEKLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 61 |
| MEKPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 62 |
| MEKPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 63 |
| MKFNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 64 |
| MKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 65 |
| MKLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 66 |
| MKPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 67 |
| MKPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 68 |
| ALTEKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 69 |
| ALTEKLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 70 |
| ALTEKPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 71 |
| ALTEKPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 72 |
| LTEKENLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 73 |
| LTEKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 74 |
| LTEKLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 75 |
| LTEKPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 76 |
| LTEKPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 77 |

-continued

| SEQUENCE | No. |
|---|---|
| TEKENLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 78 |
| TEKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 79 |
| TEKLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 80 |
| TEKPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 81 |
| TEKPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 82 |
| EKFNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 83 |
| EKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 84 |
| EKLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 85 |
| EKPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 86 |
| EKPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 87 |
| KFNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 88 |
| KNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 89 |
| KLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 90 |
| KPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 91 |
| KPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 92 |
| ALTEKNLPPGNYKKPKLLYSSNGGHFLRILPDGTVDGTRDRSDQHIQLQLSAESVGEVYIKSTETGQYL<br>CMDTDGLLYGSQTPNEECLFLERLEENHYNTYISKKHAEKNWFVGLKKNGSVKRGPRTHYGQKAILFLP<br>LPVSSD | 93 |
| ALTEKLPPGNYKKPKLLYSSNGGHFLRILPDGTVDGTRDRSDQHIQLQLSAESVGEVYIKSTETGQYLC<br>MDTDGLLYGSQTPNEECLFLERLEENHYNTYISKKHAEKNWFVGLKKNGSVKRGPRTHYGQKAILFLPL<br>PVSSD | 94 |
| ALTEKPPGNYKKPKLLYSSNGGHFLRILPDGTVDGTRDRSDQHIQLQLSAESVGEVYIKSTETGQYLCM<br>DTDGLLYGSQTPNEECLFLERLEENHYNTYISKKHAEKNWFVGLKKNGSVKRGPRTHYGQKAILFLPLP<br>VSSD | 96 |

-continued

| SEQUENCES | |
|---|---|
| SEQUENCE | No. |

ALTEKPGNYKKPKLLYSSNGGHFLRILPDGTVDGTRDRSDQHIQLQLSAESVGEVYIKSTETGQYLCMD
TDGLLYGSQTPNEECLFLERLEENHYNTYISKKHAEKNWFVGLKKNGSVKRGPRTHYGQKAILFLPLPV
SSD

97

LTEKFNLPPGNYKKPKLLYSSNGGHFLRILPDGTVDGTRDRSDQHIQLQLSAESVGEVYIKSTETGQYL
CMDTDGLLYGSQTPNEECLFLERLEENHYNTYISKKHAEKNWFVGLKKNGSVKRGPRTHYGQKAILFLP
LPVSSD

98

LTEKNLPPGNYKKPKLLYSSNGGHFLRILPDGTVDGTRDRSDQHIQLQLSAESVGEVYIKSTETGQYLC
MDTDGLLYGSQTPNEECLFLERLEENHYNTYISKKHAEKNWFVGLKKNGSVKRGPRTHYGQKAILFLPL
PVSSD

99

LTEKLPPGNYKKPKLLYSSNGGHFLRILPDGTVDGTRDRSDQHIQLQLSAESVGEVYIKSTETGQYLCM
DTDGLLYGSQTPNEECLFLERLEENHYNTYISKKHAEKNWFVGLKKNGSVKRGPRTHYGQKAILFLPLP
VSSD

100

LTEKPPGNYKKPKLLYSSNGGHFLRILPDGTVDGTRDRSDQHIQLQLSAESVGEVYIKSTETGQYLCMD
TDGLLYGSQTPNEECLFLERLEENHYNTYISKKHAEKNWFVGLKKNGSVKRGPRTHYGQKAILFLPLPV
SSD

101

LTEKPGNYKKPKLLYSSNGGHFLRILPDGTVDGTRDRSDQHIQLQLSAESVGEVYIKSTETGQYLCMDT
DGLLYGSQTPNEECLFLERLEENHYNTYISKKHAEKNWFVGLKKNGSVKRGPRTHYGQKAILFLPLPVS
SD

102

TEKFNLPPGNYKKPKLLYSSNGGHFLRILPDGTVDGTRDRSDQHIQLQLSAESVGEVYIKSTETGQYLC
MDTDGLLYGSQTPNEECLFLERLEENHYNTYISKKHAEKNWFVGLKKNGSVKRGPRTHYGQKAILFLPL
PVSSD

103

TEKNLPPGNYKKPKLLYSSNGGHFLRILPDGTVDGTRDRSDQHIQLQLSAESVGEVYIKSTETGQYLCM
DTDGLLYGSQTPNEECLFLERLEENHYNTYISKKHAEKNWFVGLKKNGSVKRGPRTHYGQKAILFLPLP
VSSD

104

TEKLPPGNYKKPKLLYSSNGGHFLRILPDGTVDGTRDRSDQHIQLQLSAESVGEVYIKSTETGQYLCMD
TDGLLYGSQTPNEECLFLERLEENHYNTYISKKHAEKNWFVGLKKNGSVKRGPRTHYGQKAILFLPLPV
SSD

105

TEKPPGNYKKPKLLYSSNGGHFLRILPDGTVDGTRDRSDQHIQLQLSAESVGEVYIKSTETGQYLCMDT
DGLLYGSQTPNEECLFLERLEENHYNTYISKKHAEKNWFVGLKKNGSVKRGPRTHYGQKAILFLPLPVS
SD

106

TEKPGNYKKPKLLYSSNGGHFLRILPDGTVDGTRDRSDQHIQLQLSAESVGEVYIKSTETGQYLCMDTD
GLLYGSQTPNEECLFLERLEENHYNTYISKKHAEKNWFVGLKKNGSVKRGPRTHYGQKAILFLPLPVSS
D

107

EKFNLPPGNYKKPKLLYSSNGGHFLRILPDGTVDGTRDRSDQHIQLQLSAESVGEVYIKSTETGQYLCM
DTDGLLYGSQTPNEECLFLERLEENHYNTYISKKHAEKNWFVGLKKNGSVKRGPRTHYGQKAILFLPLP
VSSD

108

EKNLPPGNYKKPKLLYSSNGGHFLRILPDGTVDGTRDRSDQHIQLQLSAESVGEVYIKSTETGQYLCMD
TDGLLYGSQTPNEECLFLERLEENHYNTYISKKHAEKNWFVGLKKNGSVKRGPRTHYGQKAILFLPLPV
SSD

109

EKLPPGNYKKPKLLYSSNGGHFLRILPDGTVDGTRDRSDQHIQLQLSAESVGEVYIKSTETGQYLCMDT
DGLLYGSQTPNEECLFLERLEENHYNTYISKKHAEKNWFVGLKKNGSVKRGPRTHYGQKAILFLPLPVS
SD

110

EKPPGNYKKPKLLYSSNGGHFLRILPDGTVDGTRDRSDQHIQLQLSAESVGEVYIKSTETGQYLCMDTD
GLLYGSQTPNEECLFLERLEENHYNTYISKKHAEKNWFVGLKKNGSVKRGPRTHYGQKAILFLPLPVSS
D

111

EKPGNYKKPKLLYSSNGGHFLRILPDGTVDGTRDRSDQHIQLQLSAESVGEVYIKSTETGQYLCMDTDG
LLYGSQTPNEECLFLERLEENHYNTYISKKHAEKNWFVGLKKNGSVKRGPRTHYGQKAILFLPLPVSSD

112

KFNLPPGNYKKPKLLYSSNGGHFLRILPDGTVDGTRDRSDQHIQLQLSAESVGEVYIKSTETGQYLCMD
TDGLLYGSQTPNEECLFLERLEENHYNTYISKKHAEKNWFVGLKKNGSVKRGPRTHYGQKAILFLPLPV
SSD

113

KNLPPGNYKKPKLLYSSNGGHFLRILPDGTVDGTRDRSDQHIQLQLSAESVGEVYIKSTETGQYLCMDT
DGLLYGSQTPNEECLFLERLEENHYNTYISKKHAEKNWFVGLKKNGSVKRGPRTHYGQKAILFLPLPVS
SD

114

KLPPGNYKKPKLLYSSNGGHFLRILPDGTVDGTRDRSDQHIQLQLSAESVGEVYIKSTETGQYLCMDTD
GLLYGSQTPNEECLFLERLEENHYNTYISKKHAEKNWFVGLKKNGSVKRGPRTHYGQKAILFLPLPVSS
D

115

-continued

| SEQUENCES | |
| --- | --- |
| SEQUENCE | No. |

| | |
| --- | --- |
| KPPGNYKKPKLLYSSNGGHFLRILPDGTVDGTRDRSDQHIQLQLSAESVGEVYIKSTETGQYLCMDTDG<br>LLYGSQTPNEECLFLERLEENHYNTYISKKHAEKNWFVGLKKNGSVKRGPRTHYGQKAILFLPLPVSSD | 116 |
| KPGNYKKPKLLYSSNGGHFLRILPDGTVDGTRDRSDQHIQLQLSAESVGEVYIKSTETGQYLCMDTDGL<br>LYGSQTPNEECLFLERLEENHYNTYISKKHAEKNWFVGLKKNGSVKRGPRTHYGQKAILFLPLPVSSD | 117 |
| MALTEKFNLPPGNYKKPKLLYSSNGGHFLRILPDGTVDGTRDRSDQHIQLQLSAESVGEVYIKSTETGQ<br>YLCMDTDGLLYGSQTPNEECLFLERLEENHYNTYISKKHAEKNWFVGLKKNGSVKRGPRTHYGQKAILF<br>LPLPVSSD | 118 |
| MALTEKNLPPGNYKKPKLLYSSNGGHFLRILPDGTVDGTRDRSDQHIQLQLSAESVGEVYIKSTETGQY<br>LCMDTDGLLYGSQTPNEECLFLERLEENHYNTYISKKHAEKNWFVGLKKNGSVKRGPRTHYGQKAILEL<br>PLPVSSD | 118 |
| MALTEKLPPGNYKKPKLLYSSNGGHFLRILPDGTVDGTRDRSDQHIQLQLSAESVGEVYIKSTETGQYL<br>CMDTDGLLYGSQTPNEECLFLERLEENHYNTYISKKHAEKNWFVGLKKNGSVKRGPRTHYGQKAILFLP<br>LPVSSD | 119 |
| MALTEKPPGNYKKPKLLYSSNGGHFLRILPDGTVDGTRDRSDQHIQLQLSAESVGEVYIKSTETGQYLC<br>MDTDGLLYGSQTPNEECLFLERLEENHYNTYISKKHAEKNWFVGLKKNGSVKRGPRTHYGQKAILFLPL<br>PVSSD | 120 |
| MALTEKPGNYKKPKLLYSSNGGHFLRILPDGTVDGTRDRSDQHIQLQLSAESVGEVYIKSTETGQYLCM<br>DTDGLLYGSQTPNEECLFLERLEENHYNTYISKKHAEKNWFVGLKKNGSVKRGPRTHYGQKAILFLPLP<br>VSSD | 121 |
| MLTEKFNLPPGNYKKPKLLYSSNGGHFLRILPDGTVDGTRDRSDQHIQLQLSAESVGEVYIKSTETGQY<br>LCMDTDGLLYGSQTPNEECLFLERLEENHYNTYISKKHAEKNWFVGLKKNGSVKRGPRTHYGQKAILEL<br>PLPVSSD | 122 |
| MLTEKNLPPGNYKKPKLLYSSNGGHFLRILPDGTVDGTRDRSDQHIQLQLSAESVGEVYIKSTETGQYL<br>CMDTDGLLYGSQTPNEECLFLERLEENHYNTYISKKHAEKNWFVGLKKNGSVKRGPRTHYGQKAILFLP<br>LPVSSD | 123 |
| MLTEKLPPGNYKKPKLLYSSNGGHFLRILPDGTVDGTRDRSDQHIQLQLSAESVGEVYIKSTETGQYLC<br>MDTDGLLYGSQTPNEECLFLERLEENHYNTYISKKHAEKNWFVGLKKNGSVKRGPRTHYGQKAILFLPL<br>PVSSD | 124 |
| MLTEKPPGNYKKPKLLYSSNGGHFLRILPDGTVDGTRDRSDQHIQLQLSAESVGEVYIKSTETGQYLCM<br>DTDGLLYGSQTPNEECLFLERLEENHYNTYISKKHAEKNWFVGLKKNGSVKRGPRTHYGQKAILFLPLP<br>VSSD | 125 |
| MLTEKPGNYKKPKLLYSSNGGHFLRILPDGTVDGTRDRSDQHIQLQLSAESVGEVYIKSTETGQYLCMD<br>TDGLLYGSQTPNEECLFLERLEENHYNTYISKKHAEKNWFVGLKKNGSVKRGPRTHYGQKAILFLPLPV<br>SSD | 126 |
| MTEKFNLPPGNYKKPKLLYSSNGGHFLRILPDGTVDGTRDRSDQHIQLQLSAESVGEVYIKSTETGQYL<br>CMDTDGLLYGSQTPNEECLFLERLEENHYNTYISKKHAEKNWFVGLKKNGSVKRGPRTHYGQKAILFLP<br>LPVSSD | 127 |
| MTEKNLPPGNYKKPKLLYSSNGGHFLRILPDGTVDGTRDRSDQHIQLQLSAESVGEVYIKSTETGQYLC<br>MDTDGLLYGSQTPNEECLFLERLEENHYNTYISKKHAEKNWFVGLKKNGSVKRGPRTHYGQKAILFLPL<br>PVSSD | 128 |
| MTEKLPPGNYKKPKLLYSSNGGHFLRILPDGTVDGTRDRSDQHIQLQLSAESVGEVYIKSTETGQYLCM<br>DTDGLLYGSQTPNEECLFLERLEENHYNTYISKKHAEKNWFVGLKKNGSVKRGPRTHYGQKAILFLPLP<br>VSSD | 129 |
| MTEKPPGNYKKPKLLYSSNGGHFLRILPDGTVDGTRDRSDQHIQLQLSAESVGEVYIKSTETGQYLCMD<br>TDGLLYGSQTPNEECLFLERLEENHYNTYISKKHAEKNWFVGLKKNGSVKRGPRTHYGQKAILFLPLPV<br>SSD | 130 |
| MTEKPGNYKKPKLLYSSNGGHFLRILPDGTVDGTRDRSDQHIQLQLSAESVGEVYIKSTETGQYLCMDT<br>DGLLYGSQTPNEECLFLERLEENHYNTYISKKHAEKNWFVGLKKNGSVKRGPRTHYGQKAILFLPLPVS<br>SD | 131 |
| MEKFNLPPGNYKKPKLLYSSNGGHFLRILPDGTVDGTRDRSDQHIQLQLSAESVGEVYIKSTETGQYLC<br>MDTDGLLYGSQTPNEECLFLERLEENHYNTYISKKHAEKNWFVGLKKNGSVKRGPRTHYGQKAILFLPL<br>PVSSD | 132 |

-continued

| SEQUENCES | |
|---|---|
| SEQUENCE | No. |

MEKNLPPGNYKKPKLLYSSNGGHFLRILPDGTVDGTRDRSDQHIQLQLSAESVGEVYIKSTETGQYLCM 133
DTDGLLYGSQTPNEECLFLERLEENHYNTYISKKHAEKNWFVGLKKNGSVKRGPRTHYGQKAILFLPLP
VSSD

MEKLPPGNYKKPKLLYSSNGGHFLRILPDGTVDGTRDRSDQHIQLQLSAESVGEVYIKSTETGQYLCMD 134
TDGLLYGSQTPNEECLFLERLEENHYNTYISKKHAEKNWFVGLKKNGSVKRGPRTHYGQKAILFLPLPV
SSD

MEKPPPGNYKKPKLLYSSNGGHFLRILPDGTVDGTRDRSDQHIQLQLSAESVGEVYIKSTETGQYLCMDT 135
DGLLYGSQTPNEECLFLERLEENHYNTYISKKHAEKNWFVGLKKNGSVKRGPRTHYGQKAILFLPLPVS
SD

MEKPGNYKKPKLLYSSNGGHFLRILPDGTVDGTRDRSDQHIQLQLSAESVGEVYIKSTETGQYLCMDTD 136
GLLYGSQTPNEECLFLERLEENHYNTYISKKHAEKNWFVGLKKNGSVKRGPRTHYGQKAILFLPLPVSS
D

MKFNLPPGNYKKPKLLYSSNGGHFLRILPDGTVDGTRDRSDQHIQLQLSAESVGEVYIKSTETGQYLCM 137
DTDGLLYGSQTPNEECLFLERLEENHYNTYISKKHAEKNWFVGLKKNGSVKRGPRTHYGQKAILFLPLP
VSSD

MKNLPPGNYKKPKLLYSSNGGHFLRILPDGTVDGTRDRSDQHIQLQLSAESVGEVYIKSTETGQYLCMD 138
TDGLLYGSQTPNEECLFLERLEENHYNTYISKKHAEKNWFVGLKKNGSVKRGPRTHYGQKAILFLPLPV
SSD

MKLPPGNYKKPKLLYSSNGGHFLRILPDGTVDGTRDRSDQHIQLQLSAESVGEVYIKSTETGQYLCMDT 139
DGLLYGSQTPNEECLFLERLEENHYNTYISKKHAEKNWFVGLKKNGSVKRGPRTHYGQKAILFLPLPVS
SD

MKPPGNYKKPKLLYSSNGGHFLRILPDGTVDGTRDRSDQHIQLQLSAESVGEVYIKSTETGQYLCMDTD 140
GLLYGSQTPNEECLFLERLEENHYNTYISKKHAEKNWFVGLKKNGSVKRGPRTHYGQKAILFLPLPVSS
D

MKPGNYKKPKLLYSSNGGHFLRILPDGTVDGTRDRSDQHIQLQLSAESVGEVYIKSTETGQYLCMDTDG 141
LLYGSQTPNEECLFLERLEENHYNTYISKKHAEKNWFVGLKKNGSVKRGPRTHYGQKAILFLPLPVSSD

FNLPPGNYKKPKLLYCSNGGHFLRILPDGTVDGTRDRSDQHIQLQLSAESVGEVY 142
IKSTETGQYLAXDTDGLLYGSQTPNEECLFLERLEENHYNTYISKKHAEK
NWFVGLKKNGSCKRGPRTHYGQKAILFLPLPVSSD

NLPPGNYKKPKLLYCSNGGHFLRILPDGTVDGTRDRSDQHIQLQLSAESVGEVY 143
IKSTETGQYLAXDTDGLLYGSQTPNEECLFLERLEENHYNTYISKKHAEK
NWFVGLKKNGSCKRGPRTHYGQKAILFLPLPVSSD

PPGNYKKPKLLYCSNGGHFLRILPDGTVDGTRDRSDQHIQLQLSAESVGEVY 144
IKSTETGQYLAXDTDGLLYGSQTPNEECLFLERLEENHYNTYISKKHAEK
NWFVGLKKNGSCKRGPRTHYGQKAILFLPLPVSSD

PGNYKKPKLLYCSNGGHFLRILPDGTVDGTRDRSDQHIQLQLSAESVGEVY 145
IKSTETGQYLAXDTDGLLYGSQTPNEECLFLERLEENHYNTYISKKHAEK
NWFVGLKKNGSCKRGPRTHYGQKAILFLPLPVSSD

FNLPPGNYKKPKLLYSSNGGHFLRILPDGTVDGTRDRSDQHIQLQLSAESVGEVYIKSTETGQYLCXDT 146
DGLLYGSQTPNEECLFLERLEENHYNTYISKKHAEKNWFVGLKKNGSVKRGPRTHYGQKAILFLPLPVS
SD

NLPPGNYKKPKLLYSSNGGHFLRILPDGTVDGTRDRSDQHIQLQLSAESVGEVYIKSTETGQYLCXDTD 147
GLLYGSQTPNEECLFLERLEENHYNTYISKKHAEKNWFVGLKKNGSVKRGPRTHYGQKAILFLPLPVSS
D

PPGNYKKPKLLYSSNGGHFLRILPDGTVDGTRDRSDQHIQLQLSAESVGEVYIKSTETGQYLCXDTDGL 148
LYGSQTPNEECLFLERLEENHYNTYISKKHAEKNWFVGLKKNGSVKRGPRTHYGQKAILFLPLPVSSD

PGNYKKPKLLYSSNGGHFLRILPDGTVDGTRDRSDQHIQLQLSAESVGEVYIKSTETGQYLCXDTDGLL 149
YGSQTPNEECLFLERLEENHYNTYISKKHAEKNWFVGLKKNGSVKRGPRTHYGQKAILFLPLPVSSD

ALTEKNLPPGNYKKPKLLYCSNGGHFLRILPDGTVDGTRDRSDQHIQLQLSAESVGEVY 150
IKSTETGQYLAXDTDGLLYGSQTPNEECLFLERLEENHYNTYISKKHAEK
NWFVGLKKNGSCKRGPRTHYGQKAILFLPLPVSSD

SEQUENCES

| SEQUENCE | No. |
| --- | --- |
| ALTEKLPPGNYKKPKLLYSSNGGHFLRILPDGTVDGTRDRSDQHIQLQLSAESVGEVYIKSTETGQYLC<br>XDTDGLLYGSQTPNEECLFLERLEENHYNTYISKKHAEKNWFVGLKKNGSVKRGPRTHYGQKAILFLPL<br>PVSSD | 151 |
| ALTEKPPGGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 152 |
| ALTEKPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 153 |
| LTEKFNLPPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 154 |
| LTEKNLPPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 155 |
| LTEKLPPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 156 |
| LTEKPPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 157 |
| LTEKPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 158 |
| TEKFNLPPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 159 |
| TEKNLPPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 160 |
| TEKLPPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 161 |
| TEKPPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 162 |
| TEKPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 163 |
| EKFNLPPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 164 |
| EKNLPPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 165 |
| EKLPPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 166 |
| EKPPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 167 |
| EKPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 168 |
| KFNLPPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 169 |

-continued

| SEQUENCE | No. |
|---|---|
| KNLPPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 170 |
| KLPPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 171 |
| KPPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 172 |
| KPGNYKKPKLLYCSNGGHFLRILPDGTVDGTRDRSDQHIQLQLSAESVGEVY<br>IKSTETGQYLAXDTDGLLYGSQTPNEECLFLERLEENHYNTYISKKHAEK<br>NWFVGLKKNGSCKRGPRTHYGQKAILFLPLPVSSD | 173 |
| FNLPPGNYKKPKLLYSSNGGHFLRILPDGTVDGTRDRSDQHIQLQLSAESVGEVYIKSTETGQYLCXDT<br>DGLLYGSQTPNEECLFLERLEENHYNTYISKKHAEKNWFVGLKKNGSVKRGPRTHYGQKAILFLPLPVS<br>SD | 174 |
| ALTEKFNLPPGNYKKPKLLYSSNGGHFLRILPDGTVDGTRDRSDQHIQLQLSAESVGEVYIKSTETGQY<br>LCXDTDGLLYGSQTPNEECLFLERLEENHYNTYISKKHAEKNWFVGLKKNGSVKRGPRTHYGQKAILEL<br>PLPVSSD | 175 |
| LTEKFNLPPGNYKKPKLLYSSNGGHFLRILPDGTVDGTRDRSDQHIQLQLSAESVGEVYIKSTETGQYL<br>CXDTDGLLYGSQTPNEECLFLERLEENHYNTYISKKHAEKNWFVGLKKNGSVKRGPRTHYGQKAILFLP<br>LPVSSD | 176 |
| TEKFNLPPGNYKKPKLLYSSNGGHFLRILPDGTVDGTRDRSDQHIQLQLSAESVGEVYIKSTETGQYLC<br>XDTDGLLYGSQTPNEECLFLERLEENHYNTYISKKHAEKNWFVGLKKNGSVKRGPRTHYGQKAILFLPL<br>PVSSD | 177 |
| EKFNLPPGNYKKPKLLYSSNGGHFLRILPDGTVDGTRDRSDQHIQLQLSAESVGEVYIKSTETGQYLCX<br>DTDGLLYGSQTPNEECLFLERLEENHYNTYISKKHAEKNWFVGLKKNGSVKRGPRTHYGQKAILFLPLP<br>VSSD | 178 |
| KFNLPPGNYKKPKLLYSSNGGHFLRILPDGTVDGTRDRSDQHIQLQLSAESVGEVYIKSTETGQYLCXD<br>TDGLLYGSQTPNEECLFLERLEENHYNTYISKKHAEKNWFVGLKKNGSVKRGPRTHYGQKAILFLPLPV<br>SSD | 179 |
| KFNLPPGNYKKPKLLYSSNGGHFLRILPDGTVDGTRDRSDQHIQLQLSAESVGEVYIKSTETGQYLCXD<br>TDGLLYGSQTPNEECLFLERLEENHYNTYISKKHAEKNWFVGLKKNGSVKRGPRTHYGQKAILFLPLPV<br>SSD | 180 |
| ALTEKNLPPGNYKKPKLLYSSNGGHFLRILPDGTVDGTRDRSDQHIQLQLSAESVGEVYIKSTETGQYL<br>CXDTDGLLYGSQTPNEECLFLERLEENHYNTYISKKHAEKNWFVGLKKNGSVKRGPRTHYGQKAILFLP<br>LPVSSD | 181 |
| ALTEKLPPGNYKKPKLLYSSNGGHFLRILPDGTVDGTRDRSDQHIQLQLSAESVGEVYIKSTETGQYLC<br>XDTDGLLYGSQTPNEECLFLERLEENHYNTYISKKHAEKNWFVGLKKNGSVKRGPRTHYGQKAILFLPL<br>PVSSD | 182 |
| ALTEKPPGNYKKPKLLYSSNGGHFLRILPDGTVDGTRDRSDQHIQLQLSAESVGEVYIKSTETGQYLCX<br>DTDGLLYGSQTPNEECLFLERLEENHYNTYISKKHAEKNWFVGLKKNGSVKRGPRTHYGQKAILFLPLP<br>VSSD | 183 |
| ALTEKPGNYKKPKLLYSSNGGHFLRILPDGTVDGTRDRSDQHIQLQLSAESVGEVYIKSTETGQYLCXD<br>TDGLLYGSQTPNEECLFLERLEENHYNTYISKKHAEKNWFVGLKKNGSVKRGPRTHYGQKAILFLPLPV<br>SSD | 184 |
| LTEKFNLPPGNYKKPKLLYSSNGGHFLRILPDGTVDGTRDRSDQHIQLQLSAESVGEVYIKSTETGQYL<br>CXDTDGLLYGSQTPNEECLFLERLEENHYNTYISKKHAEKNWFVGLKKNGSVKRGPRTHYGQKAILFLP<br>LPVSSD | 185 |
| LTEKNLPPGNYKKPKLLYSSNGGHFLRILPDGTVDGTRDRSDQHIQLQLSAESVGEVYIKSTETGQYLC<br>XDTDGLLYGSQTPNEECLFLERLEENHYNTYISKKHAEKNWFVGLKKNGSVKRGPRTHYGQKAILFLPL<br>PVSSD | 186 |
| LTEKLPPGNYKKPKLLYSSNGGHFLRILPDGTVDGTRDRSDQHIQLQLSAESVGEVYIKSTETGQYLCX<br>DTDGLLYGSQTPNEECLFLERLEENHYNTYISKKHAEKNWFVGLKKNGSVKRGPRTHYGQKAILFLPLP<br>VSSD | 187 |

| SEQUENCES | |
| --- | --- |
| SEQUENCE | No. |
| LTEKPPGNYKKPKLLYSSNGGHFLRILPDGTVDGTRDRSDQHIQLQLSAESVGEVYIKSTETGQYLCXD TDGLLYGSQTPNEECLFLERLEENHYNTYISKKHAEKNWFVGLKKNGSVKRGPRTHYGQKAILFLPLPV SSD | 188 |
| LTEKPPGNYKKPKLLYSSNGGHFLRILPDGTVDGTRDRSDQHIQLQLSAESVGEVYIKSTETGQYLCXDT DGLLYGSQTPNEECLFLERLEENHYNTYISKKHAEKNWFVGLKKNGSVKRGPRTHYGQKAILFLPLPVS SD | 189 |
| TEKFNLPPGNYKKPKLLYSSNGGHFLRILPDGTVDGTRDRSDQHIQLQLSAESVGEVYIKSTETGQYLC XDTDGLLYGSQTPNEECLFLERLEENHYNTYISKKHAEKNWFVGLKKNGSVKRGPRTHYGQKAILFLPL PVSSD | 190 |
| TEKNLPPGNYKKPKLLYSSNGGHFLRILPDGTVDGTRDRSDQHIQLQLSAESVGEVYIKSTETGQYLCX DTDGLLYGSQTPNEECLFLERLEENHYNTYISKKHAEKNWFVGLKKNGSVKRGPRTHYGQKAILFLPLP VSSD | 191 |
| TEKLPPGNYKKPKLLYSSNGGHFLRILPDGTVDGTRDRSDQHIQLQLSAESVGEVYIKSTETGQYLCXD TDGLLYGSQTPNEECLFLERLEENHYNTYISKKHAEKNWFVGLKKNGSVKRGPRTHYGQKAILFLPLPV SSD | 192 |
| TEKPPGNYKKPKLLYSSNGGHFLRILPDGTVDGTRDRSDQHIQLQLSAESVGEVYIKSTETGQYLCXDT DGLLYGSQTPNEECLFLERLEENHYNTYISKKHAEKNWFVGLKKNGSVKRGPRTHYGQKAILFLPLPVS SD | 193 |
| TEKPGNYKKPKLLYSSNGGHFLRILPDGTVDGTRDRSDQHIQLQLSAESVGEVYIKSTETGQYLCXDTD GLLYGSQTPNEECLFLERLEENHYNTYISKKHAEKNWFVGLKKNGSVKRGPRTHYGQKAILFLPLPVSS D | 194 |
| EKFNLPPGNYKKPKLLYSSNGGHFLRILPDGTVDGTRDRSDQHIQLQLSAESVGEVYIKSTETGQYLCX DTDGLLYGSQTPNEECLFLERLEENHYNTYISKKHAEKNWFVGLKKNGSVKRGPRTHYGQKAILFLPLP VSSD | 195 |
| EKNLPPGNYKKPKLLYSSNGGHFLRILPDGTVDGTRDRSDQHIQLQLSAESVGEVYIKSTETGQYLCXD TDGLLYGSQTPNEECLFLERLEENHYNTYISKKHAEKNWFVGLKKNGSVKRGPRTHYGQKAILFLPLPV SSD | 196 |
| EKLPPGNYKKPKLLYSSNGGHFLRILPDGTVDGTRDRSDQHIQLQLSAESVGEVYIKSTETGQYLCXDT DGLLYGSQTPNEECLFLERLEENHYNTYISKKHAEKNWFVGLKKNGSVKRGPRTHYGQKAILFLPLPVS SD | 197 |
| EKPPGNYKKPKLLYSSNGGHFLRILPDGTVDGTRDRSDQHIQLQLSAESVGEVYIKSTETGQYLCXDTD GLLYGSQTPNEECLFLERLEENHYNTYISKKHAEKNWFVGLKKNGSVKRGPRTHYGQKAILFLPLPVSS D | 198 |
| EKPGNYKKPKLLYSSNGGHFLRILPDGTVDGTRDRSDQHIQLQLSAESVGEVYIKSTETGQYLCXDTDG LLYGSQTPNEECLFLERLEENHYNTYISKKHAEKNWFVGLKKNGSVKRGPRTHYGQKAILFLPLPVSSD | 199 |
| KFNLPPGNYKKPKLLYSSNGGHFLRILPDGTVDGTRDRSDQHIQLQLSAESVGEVYIKSTETGQYLCXD TDGLLYGSQTPNEECLFLERLEENHYNTYISKKHAEKNWFVGLKKNGSVKRGPRTHYGQKAILFLPLPV SSD | 200 |
| KNLPPGNYKKPKLLYSSNGGHFLRILPDGTVDGTRDRSDQHIQLQLSAESVGEVYIKSTETGQYLCXDT DGLLYGSQTPNEECLFLERLEENHYNTYISKKHAEKNWFVGLKKNGSVKRGPRTHYGQKAILFLPLPVS SD | 201 |
| KLPPGNYKKPKLLYSSNGGHFLRILPDGTVDGTRDRSDQHIQLQLSAESVGEVYIKSTETGQYLCXDTD GLLYGSQTPNEECLFLERLEENHYNTYISKKHAEKNWFVGLKKNGSVKRGPRTHYGQKAILFLPLPVSS D | 202 |
| KPPGNYKKPKLLYSSNGGHFLRILPDGTVDGTRDRSDQHIQLQLSAESVGEVYIKSTETGQYLCXDTDG LLYGSQTPNEECLFLERLEENHYNTYISKKHAEKNWFVGLKKNGSVKRGPRTHYGQKAILFLPLPVSSD | 203 |
| KPGNYKKPKLLYSSNGGHFLRILPDGTVDGTRDRSDQHIQLQLSAESVGEVYIKSTETGQYLCXDTDGL LYGSQTPNEECLFLERLEENHYNTYISKKHAEKNWFVGLKKNGSVKRGPRTHYGQKAILFLPLPVSSD | 204 |
| FNLPPGNYKKPVLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSVKRGPRTHYGQKAILFLVLPVSSD | 205 |
| FNLPPGNYKKPKLLYSSNGGHFLRILPDGTVDGTRDRSDQHIQLQLSAESVGEVYIKSTETGQYLCMDT DGLLYGSQTPNEECLFLERLEENHYNTYISKKHAEKNWFVGLKKNGSVKRGPRTHYGQKAILFLPLPVS SD | 206 |

What is claimed is:

1. A method of treating a corneal injury in a patient, the method comprising administering to the patient a recombinant modified FGF-1 polypeptide comprising an amino acid sequence that has at least 90% sequence identity to SEQ ID NO: 206 while retaining Ser at amino acid position 16, Cys at amino acid position 66, and Val at amino acid position 117, and having an N-terminal methionine residue positioned upstream to the first residue of SEQ ID NO: 206, wherein the corneal injury is induced by exposure to a vesicant as a gas or vapor, and the first dose is administered within 48 hours of exposure to the vesicant, thereby reducing corneal epithelial cell and/or corneal endothelial cell injury.

2. The method of claim 1, wherein the corneal injury comprises a corneal endothelial injury.

3. The method of claim 2, wherein long term degeneration of the cornea is reduced.

4. The method of claim 2, wherein loss of corneal endothelial cells is reduced.

5. The method of claim 1, wherein the corneal injury comprises a stromal injury.

6. The method of claim 5, wherein stromal scarring and corneal opacity are reduced.

7. The method of claim 1, wherein the corneal injury comprises mustard gas keratopathy (MGK).

8. The method of claim 7, wherein administration of the recombinant modified FGF-1 polypeptide results in amelioration of histopathological conditions associated with MGK.

9. The method of claim 8, wherein the histopathological conditions include hyperplasia of corneal epithelial layer and epithelial-stromal cell separation.

10. The method of claim 1, wherein corneal edema and corneal erosion are reduced.

11. The method of claim 10, wherein the corneal erosion is characterized by de-epithelialization of the cornea.

12. The method of claim 11, wherein administration of the recombinant modified FGF-1 polypeptide results in reduction of the severity of corneal de-epithelialization.

13. The method of claim 11, wherein administration of the recombinant modified FGF-1 polypeptide results in faster re-epithelialization of the cornea.

14. The method of claim 1, wherein the vesicant is selected from the group consisting of: sulfur mustard (SM), nitrogen mustard (NM), lewisite, and half mustard (2-chloroethyl ethyl sulfide (CEES)).

15. The method of claim 1, wherein the vesicant is nitrogen mustard (NM) and administration of the recombinant modified FGF-1 polypeptide results in suppression of NM-induced up-regulation of a disintegrin and metalloprotease 17 (ADAM17).

16. The method of claim 1, wherein the recombinant FGF-1 polypeptide comprises an amino acid sequence that has at least 95% sequence identity to the recombinant modified FGF-1 polypeptide of SEQ ID NO: 2.

17. The method of claim 1, wherein the recombinant FGF-1 polypeptide comprises an amino acid sequence according to SEQ ID NO: 2.

18. The method of claim 1, wherein administration of the recombinant modified FGF-1 polypeptide results in reduction in corneal edema.

19. The method of claim 1, wherein the recombinant modified FGF-1 polypeptide is administered over a period of up to two weeks or until complete regeneration of the corneal epithelium.

* * * * *